(12) United States Patent
Qian

(10) Patent No.: US 11,465,975 B2
(45) Date of Patent: Oct. 11, 2022

(54) CERTAIN CHEMICAL ENTITIES, COMPOSITIONS, AND METHODS

(71) Applicant: NeuPharma, Inc., Foster City, CA (US)

(72) Inventor: Xiangping Qian, Foster City, CA (US)

(73) Assignee: NEUPHARMA, INC, San Mateo, CA (US)

( * ) Notice: Subject to any disclaimer, the term of this patent is extended or adjusted under 35 U.S.C. 154(b) by 142 days.

(21) Appl. No.: 16/967,696

(22) PCT Filed: Feb. 7, 2019

(86) PCT No.: PCT/US2019/017117
§ 371 (c)(1),
(2) Date: Aug. 5, 2020

(87) PCT Pub. No.: WO2019/157225
PCT Pub. Date: Aug. 15, 2019

(65) Prior Publication Data
US 2021/0032209 A1 Feb. 4, 2021

Related U.S. Application Data

(60) Provisional application No. 62/628,194, filed on Feb. 8, 2018.

(51) Int. Cl.
| | |
|---|---|
| A61K 31/505 | (2006.01) |
| C07D 239/84 | (2006.01) |
| G01N 33/574 | (2006.01) |
| A61P 35/00 | (2006.01) |
| A61K 45/06 | (2006.01) |

(52) U.S. Cl.
CPC ......... *C07D 239/84* (2013.01); *G01N 33/574* (2013.01); *A61K 45/06* (2013.01); *C07B 2200/13* (2013.01); *G01N 2333/485* (2013.01)

(58) Field of Classification Search
CPC .............................. A61K 31/505; A61P 35/00
USPC .................................................... 514/252.17
See application file for complete search history.

(56) References Cited

U.S. PATENT DOCUMENTS

| | | | |
|---|---|---|---|
| 5,033,252 A | 7/1991 | Carter | |
| 5,052,558 A | 10/1991 | Carter | |
| 5,323,907 A | 6/1994 | Kalvelage | |
| 5,846,514 A | 12/1998 | Foster et al. | |
| 6,334,997 B1 | 1/2002 | Foster et al. | |
| 8,946,235 B2 | 2/2015 | Butterworth et al. | |
| 2014/0255428 A1 | 9/2014 | Li et al. | |
| 2017/0050936 A1 | 2/2017 | Qian et al. | |

FOREIGN PATENT DOCUMENTS

| | | |
|---|---|---|
| WO | WO-9722596 A1 | 6/1997 |
| WO | WO-9730035 A1 | 8/1997 |
| WO | WO-9732856 A1 | 9/1997 |
| WO | WO-9813354 A1 | 4/1998 |
| WO | WO-9902166 A1 | 1/1999 |
| WO | WO-0040529 A1 | 7/2000 |
| WO | WO-0041669 A2 | 7/2000 |
| WO | WO-0047212 A1 | 8/2000 |
| WO | WO-0192224 A1 | 12/2001 |
| WO | WO-0204434 A1 | 1/2002 |
| WO | WO-0208213 A1 | 1/2002 |
| WO | WO-2015027222 A2 | 2/2015 |

OTHER PUBLICATIONS

Evans. Synthesis of radiolabeled compounds. J Radioanal Chem 64(1-2):9-32 (1981).
Kabalka et al. The Synthesis of Radiolabeled Compounds via Organometallic Intermediates. Tetrahedron 45(21):6601-6621 (1989).
Lombardo et al. Discovery of N-(2-chloro-6-methyl-phenyl)-2-(6-(4-(2-hydroxyethyl)-piperazin-1-yl)-2-methylpyrimidin-4-ylamino)thiazole-5-carboxamide (BMS-354825), a dual Src/Abl kinase inhibitor with potent antitumor activity in preclinical assays. J Med Chem. Dec. 30, 2004;47(27):6658-61.
PCT/US2019/017117 International Preliminary Report on Patentability dated Aug. 11, 2020.
PCT/US2019/017117 International Search Report and Written Opinion dated Apr. 22, 2019.
Stem, et al. Overview of monoclonal antibodies in cancer therapy: present and promise. Crit Rev Oncol Hematol. Apr. 2005;54(1):11-29.
The United States Department of Health and Human Services, Food and Drug Administration, "Guidance for Industry, Q1A(R2) Stability testing of New Drug Substances and Drug Products" Nov. 2003, Revision 2, pp. 1-25.

*Primary Examiner* — Raymond J Henley, III
(74) *Attorney, Agent, or Firm* — Wilson Sonsini Goodrich & Rosati

(57) ABSTRACT

Chemical entities that are kinase inhibitors, their polymorphs, pharmaceutical compositions and methods of treatment of cancer are described herein.

30 Claims, 16 Drawing Sheets

CERTAIN CHEMICAL ENTITIES, COMPOSITIONS, AND METHODS

CROSS-REFERENCE

This application is a U.S. National Phase Application of PCT International Application No. PCT/US2019/017117 filed Feb. 7, 2019, which claims the benefit of U.S. Provisional Application No. 62/628,194, filed on Feb. 8, 2018, each of which is hereby incorporated by reference in its entirety.

BACKGROUND OF THE INVENTION

There are at least 400 enzymes identified as protein kinases. These enzymes catalyze the phosphorylation of target protein substrates. The phosphorylation is usually a transfer reaction of a phosphate group from ATP to the protein substrate. The specific structure in the target substrate to which the phosphate is transferred is a tyrosine, serine or threonine residue. Since these amino acid residues are the target structures for the phosphoryl transfer, these protein kinase enzymes are commonly referred to as tyrosine kinases or serine/threonine kinases.

The phosphorylation reactions, and counteracting phosphatase reactions, at the tyrosine, serine and threonine residues are involved in countless cellular processes that underlie responses to diverse intracellular signals (typically mediated through cellular receptors), regulation of cellular functions, and activation or deactivation of cellular processes. A cascade of protein kinases often participate in intracellular signal transduction and are necessary for the realization of these cellular processes. Because of their ubiquity in these processes, the protein kinases can be found as an integral part of the plasma membrane or as cytoplasmic enzymes or localized in the nucleus, often as components of enzyme complexes. In many instances, these protein kinases are an essential element of enzyme and structural protein complexes that determine where and when a cellular process occurs within a cell.

The identification of effective small compounds which specifically inhibit signal transduction and cellular proliferation by modulating the activity of tyrosine and serine/threonine kinases to regulate and modulate abnormal or inappropriate cell proliferation, differentiation, or metabolism is therefore desirable. In particular, the identification of compounds that specifically inhibit the function of a kinase which is essential for processes leading to cancer would be beneficial.

While such compounds are often initially evaluated for their activity when dissolved in solution, solid state characteristics such as polymorphism are also important. Polymorphic forms of a drug substance, such as a kinase inhibitor, can have different physical properties, including melting point, apparent solubility, dissolution rate, optical and mechanical properties, vapor pressure, and density. These properties can have a direct effect on the ability to process or manufacture a drug substance and the drug product. Moreover, differences in these properties can and often lead to different pharmacokinetics profiles for different polymorphic forms of a drug. Therefore, polymorphism is often an important factor under regulatory review of the 'sameness' of drug products from various manufacturers. For example, polymorphism has been evaluated in many multi-million dollar and even multi-billion dollar drugs, such as warfarin sodium, famotidine, and ranitidine. Polymorphism can affect the quality, safety, and/or efficacy of a drug product, such as a kinase inhibitor. Thus, there still remains a need for polymorphs of kinase inhibitors. The present disclosure addresses this need and provides related advantages as well.

SUMMARY OF THE INVENTION

In one aspect, the disclosure provides a composition comprising a crystalline form of a compound of Formula I:

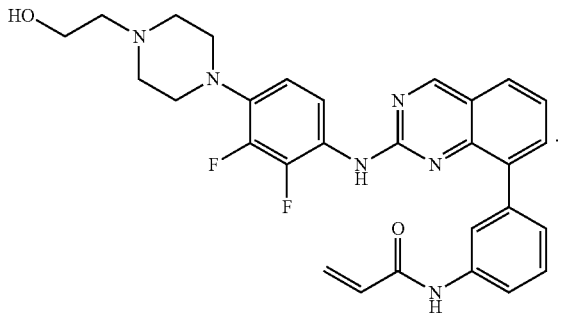

Formula I

In some embodiments, the composition comprises a crystalline form of the compound of Formula I. In some embodiments, the composition can be stored at about 40° C., 75% relative humidity, for a time period of about 30 days or more without significant degradation or change in the crystalline form. In some embodiments, the composition can be stored at about 60° C. for a time period of about 30 days or more without significant degradation or change in the crystalline form.

In some embodiments, the crystalline form is a polymorph Form I of the compound of Formula I. In some embodiments, the polymorph Form I is characterized by an X-ray powder diffraction pattern comprising peaks at 21.4±0.2 degrees, 18.3±0.2 degrees and 22.7±0.2 degrees two theta. In some embodiments, the X-ray powder diffraction pattern further comprises at least one peak selected from 13.5±0.2 degrees, 17.2±0.2 degrees, and 5.0±0.2 degrees two theta. In some embodiments, the X-ray powder diffraction pattern further comprises at least one peak selected from 25.8±0.2 degrees and 23.6±0.2 degrees two theta. In some embodiments, the X-ray powder diffraction pattern comprises peaks at 21.4±0.2 degrees, 18.3±0.2 degrees, 22.7±0.2 degrees, 13.5±0.2 degrees, 17.2±0.2 degrees, 5.0±0.2 degrees, 25.8±0.2 degrees, and 23.6±0.2 degrees two theta.

In some embodiments, the polymorph Form I is characterized by a differential scanning calorimetry (DSC) thermogram comprising an endotherm in the range of about 160-180° C. In some embodiments, the polymorph Form I has a melting point of about 173° C.

In some embodiments, greater than about 90%, 95%, or 99% by weight of the compound of Formula I in the composition is the polymorph Form I. In some embodiments, the polymorph Form I comprises (i) rod like crystals or (ii) rod and column crystals. In some embodiments, the polymorph Form I is dry, non-solvated, non-hydrated, and/or non-hygroscopic.

In some embodiments, the crystalline form is a polymorph Form II of the compound of Formula I. In some embodiments, the polymorph Form II is characterized by an X-ray powder diffraction pattern comprising peaks at 7.5±0.2 degrees, 19.5±0.2 degrees, and 23.5±0.2 degrees two theta. In some embodiments, the polymorph Form II is characterized by a DSC thermogram comprising endotherms in the range of about 120-150° C. and about 175-200° C., for example endotherms at about 124° C. and about 183° C. In some embodiments, the DSC thermogram further comprises exotherm at about 150-160° C., for example at about 153° C.

In some embodiments, the crystalline form is a polymorph Form III of the compound of Formula I. In some embodiments, the polymorph Form III is characterized by an X-ray powder diffraction pattern comprising a peak at 6.5±0.2 degrees two theta. In some embodiments, the X-ray powder diffraction pattern further comprises at least one peak selected from 19.6±0.2 degrees, 22.4±0.2 degrees, 13.0±0.2 degrees and 20.3±0.2 degrees two theta. In some embodiments, the X-ray powder diffraction pattern further comprises at least one peak selected from 14.0±0.2 degrees, 26.2±0.2 degrees, 16.6±0.2 degrees, and 23.3±0.2 degrees two theta. In some embodiments, the X-ray powder diffraction pattern comprises peaks at 6.5±0.2 degrees, 19.6±0.2 degrees, 22.4±0.2 degrees, 13.0±0.2 degrees, 20.3±0.2 degrees, 14.0±0.2 degrees, 26.2±0.2 degrees, 16.6±0.2 degrees, and 23.3±0.2 degrees two theta.

In some embodiments, the polymorph Form III is characterized by a DSC thermogram comprising endotherms in the range of about 116-136° C. and about 184-194° C., for example endotherms at about 120° C. and about 188° C. In some embodiments, the polymorph Form III has a melting point of about 188° C.

In some embodiments, greater than about 90%, 95%, or 99% of the compound of Formula I in the composition is the polymorph Form III. In some embodiments, the polymorph Form III is dry, or the polymorph Form III is non-solvated, or the polymorph Form III is solvated.

In some embodiments, the crystalline form is a polymorph Form IV of the compound of Formula I. In some embodiments, the polymorph Form IV is characterized by an X-ray powder diffraction pattern comprising peaks at 24.5±0.2 degrees and 20.7±0.2 degrees two theta. In some embodiments, the X-ray powder diffraction pattern further comprises at least one peak selected from 19.6±0.2 degrees, 18.0±0.2 degrees, 23.2±0.2 degrees, 7.4±0.2 degrees, 8.0±0.2 degrees, 16.1±0.2 degrees and 17.8±0.2 degrees two theta. In some embodiments, the X-ray powder diffraction pattern comprises peaks at 24.5±0.2 degrees, 20.7±0.2 degrees, 19.6±0.2 degrees, 18.0±0.2 degrees, 23.2±0.2 degrees, 7.4±0.2 degrees, 8.0±0.2 degrees, 16.1±0.2 degrees, and 17.8±0.2 degrees two theta.

In some embodiments, the polymorph Form IV is characterized by a DSC thermogram comprising endotherms in the range of about 115-135° C., about 168-178° C. and about 184-194° C., for example endotherms at about 119° C., about 170° C. and about 187° C. In some embodiments, the DSC thermogram further comprises exotherm at about 137-147° C., for example at about 140° C.

In some embodiments, greater than about 90%, 95%, or 99% of the compound of Formula I in the composition is the polymorph Form IV. In some embodiments, the polymorph Form IV is dry or the polymorph Form IV is solvated.

In some embodiments, the crystalline form is a polymorph Form V of the compound of Formula I. In some embodiments, the polymorph Form V is characterized by an X-ray powder diffraction pattern comprising peaks at 5.7±0.2 degrees, 21.6±0.2 degrees, and 14.6±0.2 degrees two theta. In some embodiments, the X-ray powder diffraction pattern further comprises at least one peak selected from 19.5±0.2 degrees, 20.0±0.2 degrees, 25.1±0.2 degrees, 7.2±0.2 degrees, 21.4±0.2 degrees, and 12.2±0.2 degrees two theta. In some embodiments, the X-ray powder diffraction pattern comprises peaks at 5.7±0.2 degrees, 21.6±0.2 degrees, 14.6±0.2 degrees, 19.5±0.2 degrees, 20.0±0.2 degrees, 25.1±0.2 degrees, 7.2±0.2 degrees, 21.4±0.2 degrees, and 12.2±0.2 degrees two theta.

In some embodiments, the polymorph Form V is characterized by a DSC thermogram comprising endotherms in the range of about 152-162° C. and about 183-193° C., for example endotherms at about 156° C. and about 187° C. In some embodiments, the DSC thermogram further comprises an exotherm at about 159° C.

In some embodiments, greater than about 90%, 95%, or 99% of the compound of Formula I in the composition is the polymorph Form V. In some embodiments, the polymorph Form V is dry or the polymorph Form V is solvated.

In some embodiments, the crystalline form is a polymorph Form VI of the compound of Formula I. In some embodiments, the polymorph Form VI is characterized by an X-ray powder diffraction pattern comprising a peak at 6.6±0.2 degrees two theta. In some embodiments, the X-ray powder diffraction pattern further comprises at least one peak selected from 20.5±0.2 degrees, 22.6±0.2 degrees, and 14.1±0.2 degrees two theta. In some embodiments, the X-ray powder diffraction pattern further comprises peaks at least one peak selected from 26.0±0.2 degrees, 19.7±0.2 degrees, 12.4±0.2 degrees, 17.6±0.2 degrees and 23.3±0.2 degrees two theta. In some embodiments, the X-ray powder diffraction pattern comprises peaks at 6.6±0.2 degrees, 20.5±0.2 degrees, 22.6±0.2 degrees, 14.1±0.2 degrees, 26.0±0.2 degrees, 19.7±0.2 degrees, 12.4±0.2 degrees, 17.6±0.2 degrees, and 23.3±0.2 degrees two theta.

In some embodiments, the polymorph Form VI is characterized by a DSC thermogram comprising endotherms in the range of about 120-140° C. and about 185-195° C., for example endotherms at about 123° C. and at about 188° C. In some embodiments, the polymorph Form VI has a melting point of about 188° C.

In some embodiments, greater than about 90%, 95%, or 99% of the compound of Formula I in the composition is the polymorph Form VI. In some embodiments, the polymorph Form VI is dry, or the polymorph Form VI is non-solvated, or the polymorph Form VI is solvated.

In some embodiments, the crystalline form is a polymorph Form VIII of the compound of Formula I. In some embodiments, the polymorph Form VIII is characterized by an X-ray powder diffraction pattern comprising a peak at 20.7±0.2 degrees two theta. In some embodiments, the X-ray powder diffraction pattern further comprises at least one peak selected from 22.7±0.2 degrees, 6.7±0.2 degrees, 7.4±0.2 degrees, and 14.1±0.2 degrees two theta. In some embodiments, the X-ray powder diffraction pattern further comprises at least one peak selected from 15.7±0.2 degrees, 26.1±0.2 degrees, 19.7±0.2 degrees, and 12.5±0.2 degrees two theta. In some embodiments, the X-ray powder diffraction pattern comprises peaks at 20.7±0.2 degrees, 22.7±0.2 degrees, 6.7±0.2 degrees, 7.4±0.2 degrees, 14.1±0.2 degrees, 15.7±0.2 degrees, 26.1±0.2 degrees, 19.7±0.2 degrees, and 12.5±0.2 degrees two theta.

In some embodiments, the polymorph Form VIII is characterized by a DSC thermogram comprising endotherm in the range of about 182-192° C., for example endotherm at about 187° C. In some embodiments, the DSC thermogram further comprises endotherm at about 110-135° C. for example at about 114° C.

In another aspect the disclosure provides a composition comprising one or more crystalline forms of the compound of Formula I:

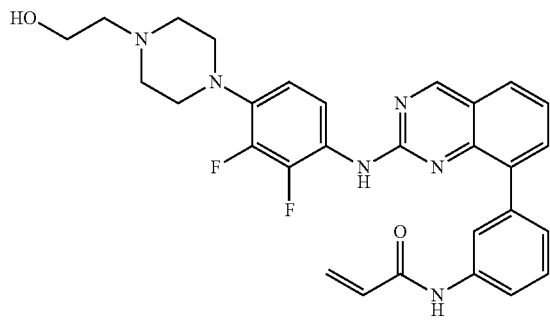

Formula I wherein the one or more crystalline forms are selected from the group consisting of: (i) a crystalline form characterized by an X-ray powder diffraction pattern comprising peaks at 21.4±0.2 degrees, 18.3±0.2 degrees and 22.7±0.2 degrees two theta; (ii) a crystalline form characterized by an X-ray powder diffraction pattern comprising peaks at 7.5±0.2 degrees, 19.5±0.2 degrees and 23.5±0.2 degrees two theta; (iii) a crystalline form characterized by an X-ray powder diffraction pattern comprising peaks at 6.5±0.2 degrees, 19.6±0.2 degrees, 22.4±0.2 degrees, 13.0±0.2 degrees and 20.3±0.2 degrees two theta; (iv) a crystalline form characterized by an X-ray powder diffraction pattern comprising peaks at 24.5±0.2 degrees, 20.7±0.2 degrees, 19.6±0.2 degrees, 18.0±0.2 degrees, 23.2±0.2 degrees, 7.4±0.2 degrees, and 8.0±0.2 degrees two theta; (v) a crystalline form characterized by an X-ray powder diffraction pattern comprising peaks at 5.7±0.2 degrees, 21.6±0.2 degrees, 14.6±0.2 degrees two theta; (vi) a crystalline form characterized by an X-ray powder diffraction pattern comprising peaks at 6.6±0.2 degrees, 20.5±0.2 degrees, 22.6±0.2 degrees, and 14.1±0.2 degrees two theta; and (vii) a crystalline form characterized by an X-ray powder diffraction pattern comprising peaks at 20.7±0.2 degrees, 22.7±0.2 degrees, 6.7±0.2 degrees, 7.4±0.2 degrees, and 14.1±0.2 degrees two theta.

In another aspect the disclosure provides a pharmaceutical composition comprising a pharmaceutically acceptable carrier and the composition disclosed herein.

In another aspect, the disclosure provides a method of treating a cancer in a subject in need thereof, comprising administering to the subject a therapeutically effective amount of the composition disclosed herein.

In another aspect, the disclosure provides a method of treating a disorder mediated by EGFR in a subject in need thereof, comprising administering to the subject a therapeutically effective amount of the composition disclosed herein.

In another aspect, the disclosure provides a method of treating a disorder in a subject in need thereof, the method comprising: (a) determining the presence or absence of an EGFR mutation in a biological sample isolated from the subject; and (b) if an EGFR mutation or double mutation is determined to be present in the subject, administering to the subject a therapeutically effective amount of the composition disclosed herein. In some embodiments, the EGFR mutation is a mutation in codon 790, del E746-A750, del E747-E749/A750P, del E747-S752/P753S, del E747-T751/Sins/A750P, del S7524759, G719S, G719C, L861Q, L858R, T790M, or L858R/T790M. In some embodiments, determining the presence or absence of the EGFR mutation comprises (i) amplifying EGFR nucleic acid from the biological sample and sequencing the amplified nucleic acid or (ii) detecting a mutant EGFR polypeptide in the biological sample using a binding agent to a mutant EGFR polypeptide.

In some embodiments, the disorder treated by the methods disclosed herein is a cancer. In some embodiments, the cancer is colon carcinoma, pancreatic cancer, breast cancer, ovarian cancer, prostate cancer, thyroid cancer, fibrosarcoma, myxosarcoma, liposarcoma, chondrosarcoma, osteogenic sarcoma, chondroma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, non-small cell lung cancer, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, or heavy chain disease. In some embodiments, the cancer is non-small cell lung cancer, colon cancer, thyroid cancer, or ovarian cancer.

In some embodiments, the methods of treatment disclosed herein further comprise administering an additional anti-cancer and/or cytotoxic agent to the subject.

In another aspect, the disclosure provides a method of preparing a crystalline form of a compound of Formula I:

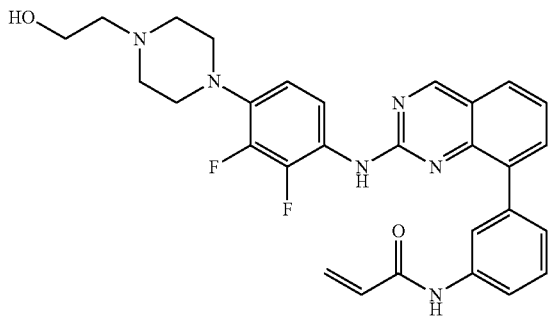

Formula I wherein the method comprises: (i) dissolving the compound of Formula I in a first solvent to obtain a mixture; and (ii) crystallizing the mixture to obtain the crystalline form of the compound of Formula I. In some embodiments, the first solvent comprises ethyl acetate, DCM, ethyl alcohol, or isopropyl alcohol. In some embodiments, the dissolving of the compound of Formula I is performed at a temperature of about 50-90° C., for example at a temperature of about 55-65° C. or about 75-85° C. In some embodiments, the method further comprises adding a second solvent to the mixture before crystallizing. In some embodiments, the second solvent is an alkane, for example heptane. In some embodiments, crystallizing the mixture comprises heating the mixture to a temperature of about 75-85° C. and maintaining the mixture at this temperature for about 30 mins-2 hours, e.g. about 1 hour. In some embodiments, crystalizing further comprises cooling the heated mixture to a temperature of about 50-60° C. and maintaining the mixture at this temperature for about 1-3 hours, e.g. about 2 hours. In some embodiments, the heating followed by the cooling is repeated at least 2 times. In some embodiments, the mixture is further cooled down to about 20-30° C. and is maintained at this temperature for about 1-4 hours, e.g. about 3 hours.

In some embodiments, the method further comprises treating the mixture with a drying agent, decolorizing agent, and/or a silica metal scavenger. In some embodiments, the drying agent is anhydrous $Na_2SO_4$ and/or the decolorizing agent is activated charcoal.

In some embodiments, the method further comprises filtering the mixture treated with the drying agent, decolorizing agent, and/or a silica metal scavenger and concentrating the filtrate. In some embodiments, the concentration is performed under vacuum at a temperature of about 20-30° C. In some embodiments, the method further comprises dissolving the concentrated product in another solvent, for example in DCM. In some embodiments, the mixture is further cooled down to about 20-30° C.

In some embodiments, the method further comprising filtering the mixture after crystallization and/or drying the obtained crystalline form.

In another aspect, the disclosure provides a method of making a second crystalline form of a compound of Formula I:

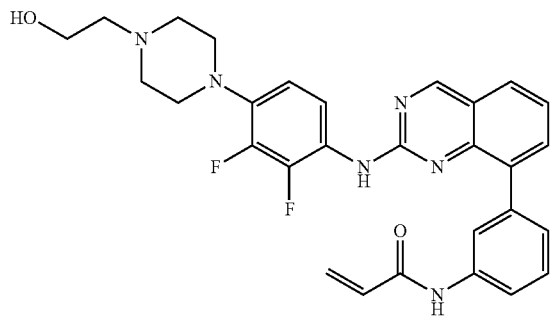

Formula I wherein the method comprises drying a first crystalline form of the compound of Formula I at a temperature of about 70-90° C. In some embodiments, the first form is Form III and the second form is Form V. In some embodiments, the first form is Form VI and the second form is Form VIII.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

DESCRIPTION OF THE DRAWINGS

The novel features of the invention are set forth with particularity in the appended claims. An understanding of the features and advantages of the present invention may be obtained by reference to the following detailed description that sets forth illustrative embodiments, in which the principles of the invention are utilized, and the accompanying drawings of which:

DETAILED DESCRIPTION OF THE INVENTION

Figure 1:
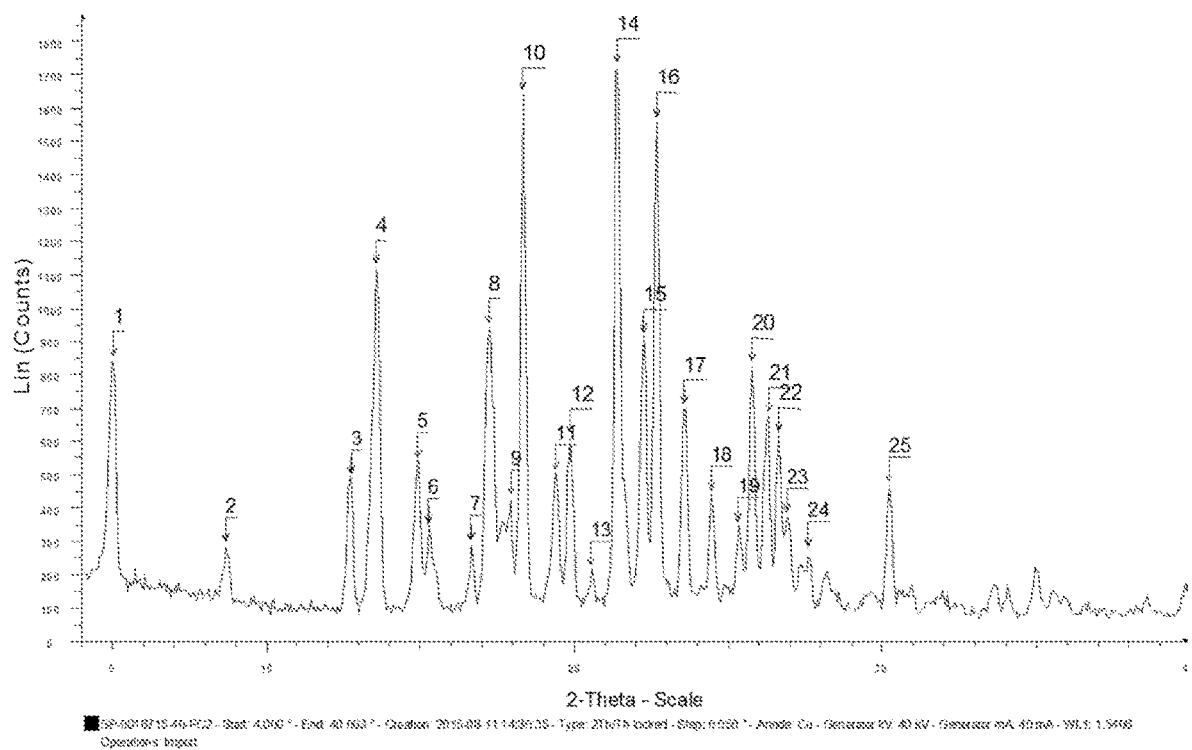
FIG. 1 shows the X-ray powder diffraction (XRPD) for polymorph Form I of the compound of Formula I.

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the appended claims define the scope of the invention and that methods and structures within the scope of these claims and their equivalents be covered thereby.

I. Definitions

As used herein, the following words and phrases are generally intended to have the meanings as set forth below, except to the extent that the context in which they are used indicates otherwise.

As used herein, "active agent" is used to indicate a chemical entity which has biological activity. In certain embodiments, an "active agent" is a compound having pharmaceutical utility. For example an active agent may be an anti-cancer therapeutic.

As used herein, "modulation" refers to a change in activity as a direct or indirect response to the presence of a chemical entity as described herein, relative to the activity of in the absence of the chemical entity. The change may be an increase in activity or a decrease in activity, and may be due to the direct interaction of the compound with the a target or due to the interaction of the compound with one or more other factors that in turn affect the target's activity. For example, the presence of the chemical entity may, for example, increase or decrease the target activity by directly binding to the target, by causing (directly or indirectly) another factor to increase or decrease the target activity, or by (directly or indirectly) increasing or decreasing the amount of target present in the cell or organism.

As used herein, "therapeutically effective amount" of a chemical entity described herein refers to an amount effective, when administered to a human or non-human subject, to provide a therapeutic benefit such as amelioration of symptoms, slowing of disease progression, or prevention of disease.

"Treating" or "treatment" encompasses administration of at least one compound of Formula I, or a pharmaceutically acceptable salt thereof, to a mammalian subject, particularly a human subject, in need of such an administration and includes (i) arresting the development of clinical symptoms of the disease, such as cancer, (ii) bringing about a regression in the clinical symptoms of the disease, such as cancer, and/or (iii) prophylactic treatment for preventing the onset of the disease, such as cancer.

As used herein, a "pharmaceutically acceptable" component is one that is suitable for use with humans and/or animals without undue adverse side effects (such as toxicity, irritation, and allergic response) commensurate with a reasonable benefit/risk ratio.

"Pharmaceutically acceptable salts" include, but are not limited to salts with inorganic acids, such as hydrochlorate, carbonate, phosphate, hydrogenphosphate, diphosphate, hydrobromate, sulfate, sulfinate, nitrate, and like salts; as well as salts with an organic acid, such as malate, malonate, maleate, fumarate, tartrate, succinate, citrate, acetate, lactate, gluconate, methanesulfonate, Tris (hydroxymethyl-aminomethane), p-toluenesulfonate, priopionate, 2-hydroxyethylsulfonate, benzoate, salicylate, stearate, oxalate, pamoate, and alkanoate such as acetate, HOOC—$(CH_2)_n$—COOH where n is 0-4, and like salts. Other salts include sulfate, methasulfonate, bromide, trifluoracetate, picrate, sorbate, benzilate, salicilate, nitrate, phthalate or morpholine. Pharmaceutically acceptable cations include, but are not limited to sodium, potassium, calcium, aluminum, lithium, and ammonium.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

As used herein, "subject" refers to a mammal that has been or will be the object of treatment, observation or experiment. The methods described herein can be useful in both human therapy and veterinary applications. In some embodiments, the subject is a human.

The term "mammal" is intended to have its standard meaning, and encompasses humans, dogs, cats, sheep, and cows, for example.

"Prodrugs" described herein include any compound that becomes a compound of Formula I when administered to a subject, e.g., upon metabolic processing of the prodrug. Similarly, "pharmaceutically acceptable salts" includes "prodrugs" of pharmaceutically acceptable salts. Examples of prodrugs include derivatives of functional groups, such as a carboxylic acid group, in the compounds of Formula I. Exemplary prodrugs of a carboxylic acid group include, but are not limited to, carboxylic acid esters such as alkyl esters, hydroxyalkyl esters, arylalkyl esters, and aryloxyalkyl esters. Other exemplary prodrugs include lower alkyl esters such as ethyl ester, acyloxyalkyl esters such as pivaloyloxymethyl (POM), glycosides, and ascorbic acid derivatives. Other exemplary prodrugs include amides of carboxylic acids. A discussion of prodrugs is provided in T. Higuchi and V. Stella, Pro-drugs as Novel Delivery Systems, Vol. 14 of the A.C.S. Symposium Series, in Edward B. Roche, ed., Bioreversible Carriers in Drug Design, American Pharmaceutical Association and Pergamon Press, 1987, and in Design of Prodrugs, ed. H. Bundgaard, Elsevier, 1985.

The compounds disclosed herein can be used in different enriched isotopic forms, e.g., enriched in the content of $^2H$, $^3H$, $^{13}C$ and/or $^{14}C$. In one particular embodiment, the compound is deuterated at least one position. Such deuterated forms can be made by the procedure described in U.S. Pat. Nos. 5,846,514 and 6,334,997. As described in U.S. Pat. Nos. 5,846,514 and 6,334,997, deuteration can improve the efficacy and increase the duration of action of drugs.

Deuterium substituted compounds can be synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

A "solvate" is formed by the interaction of a solvent and a compound. The term "compound" is intended to include solvates of compounds. Similarly, "pharmaceutically acceptable salts" includes solvates of pharmaceutically acceptable salts. Suitable solvates are pharmaceutically acceptable solvates, such as hydrates, including monohydrates and hemi-hydrates. Also included are solvates formed with the one or more crystallization solvents.

"Crystalline form," "polymorph," "Form," and "form" may be used interchangeably herein, and are meant to include all crystalline and amorphous forms of the compound, including, for example, polymorphs, pseudopolymorphs, salts, solvates, hydrates, unsolvated polymorphs (including anhydrates), conformational polymorphs, and amorphous forms, as well as mixtures thereof, unless a particular crystalline or amorphous form is referred to. Compounds of the present disclosure include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof.

Pharmaceutically acceptable forms of the compounds recited herein include pharmaceutically acceptable salts, chelates, non-covalent complexes, prodrugs, and mixtures thereof.

A "chelate" is formed by the coordination of a compound to a metal ion at two (or more) points. The term "compound" is intended to include chelates of compounds. Similarly, "pharmaceutically acceptable salts" includes chelates of pharmaceutically acceptable salts.

A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding). Such non-covalent complexes are included in the term "compound". Similarly, pharmaceutically acceptable salts include "non-covalent complexes" of pharmaceutically acceptable salts.

When ranges are used herein for physical properties, such as molecular weight, or chemical properties, such as chemical formulae, all combinations and sub combinations of ranges and specific embodiments therein are intended to be included.

The term "about" when referring to a number or a numerical range means that the number or numerical range referred to is an approximation within experimental variability (or within statistical experimental error), and thus the number or numerical range may vary from, for example, between 1% and 15% of the stated number or numerical range.

As used herein, "significant" refers to any detectable change that is statistically significant in a standard parametric test of statistical significance such as Student's T-test, where p<0.05.

As used herein, "cancer" refers to all types of cancer or neoplasm or malignant tumors found in mammals, including carcinomas and sarcomas. Examples of cancer are cancer of the brain, breast, cervix, colon, head & neck, kidney, lung, non-small cell lung, melanoma, mesothelioma, ovary, sarcoma, stomach, uterus and Medulloblastoma.

As used herein, the term EGFR is used to refer the epidermal growth factor receptor (EGFR), a receptor tyrosine kinase of the ErbB family. The terms "EGFR", "Her1", "ErbB1" and the like are used interchangeably to refer to the gene or protein product of the gene.

II. Crystalline Compounds and Methods of Making

The polymorphs made according to the methods of the invention may be characterized by any methodology according to the art. For example, the polymorphs made according to the methods of the invention may be characterized by X-ray powder diffraction (XRPD), differential scanning calorimetry (DSC), thermogravimetric analysis (TGA), hot-stage microscopy, and/or spectroscopy (e.g., Raman, solid state nuclear magnetic resonance (ssNMR), and infrared (IR)).

XRPD: Polymorphs according to the invention may be characterized by XRPD. The relative intensities of XRPD peaks can vary, depending upon the particle size, the sample preparation technique, the sample mounting procedure and the particular instrument employed. Moreover, instrument variation and other factors can affect the 2-θ values. Therefore, the XRPD peak assignments can vary, for example by plus or minus about 0.2 degrees.

Figure 2:
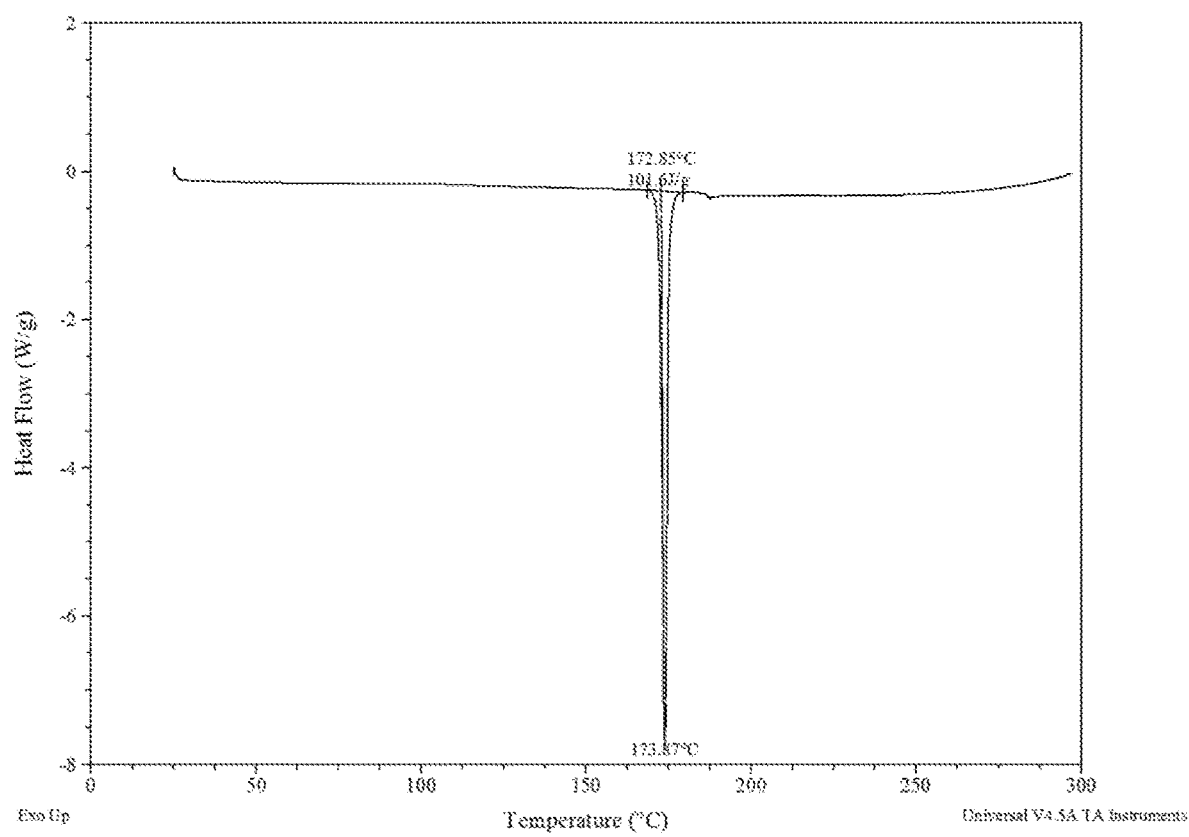
FIG. 2 shows an exemplary differential scanning calorimetry (DSC) thermogram of the polymorph Form I of the compound of Formula I.
Figure 4:
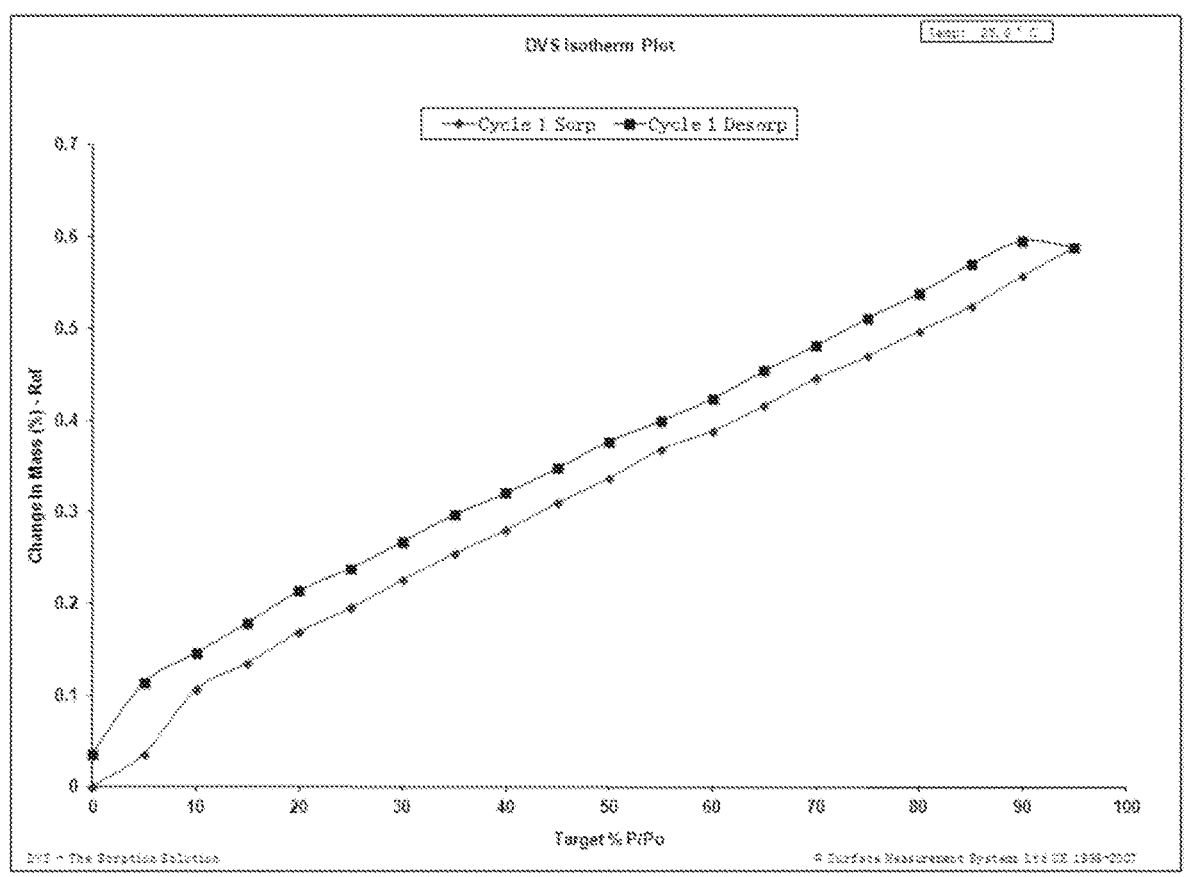
FIG. 4 shows the DVS isothermal sorption and desorption curves for of the polymorph Form I of the compound of Formula I.

DSC: Polymorphs according to the invention can also be identified by its characteristic DSC trace such as shown in FIGS. 2, 4 etc. For DSC, it is known that the temperatures observed will depend upon the rate of temperature change as well as sample preparation technique and the particular instrument employed. Thus, the values reported herein relating to DSC thermograms can vary, for example by plus or minus about 4° C.

TGA: The polymorphic forms of the invention may also give rise to thermal behavior different from that of the amorphous material or another polymorphic form. Thermal behavior may be measured in the laboratory by thermogravimetric analysis (TGA) which may be used to distinguish some polymorphic forms from others. In one aspect, the polymorph may be characterized by thermogravimetric analysis.

The polymorph forms of the invention are useful in the production of medicinal preparations and can be obtained by means of a crystallization process to produce crystalline and semi-crystalline forms or a solidification process to obtain the amorphous form. In various embodiments, the crystallization is carried out by either generating the desired compound (for example compound of Formula I) in a reaction mixture and isolating the desired polymorph from the reaction mixture, or by dissolving raw compound in a solvent, optionally with heat, followed by crystallizing/solidifying the product by cooling (including active cooling) and/or by the addition of an antisolvent for a period of time. The crystallization or solidification may be followed by drying carried out under controlled conditions until the desired water content is reached in the end polymorphic form.

In one aspect, the invention provides methods of making one or more polymorphs of the compound of the Formula I:

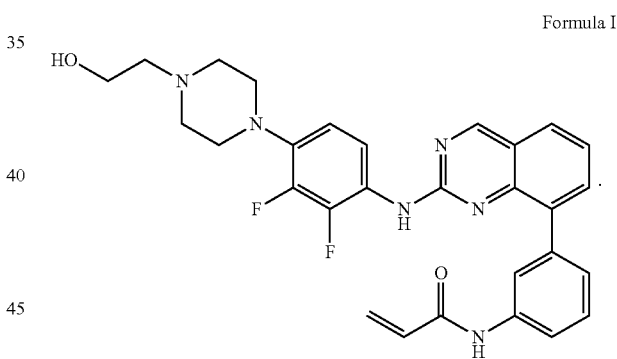

Formula I

In various embodiments, the compound of Formula I is made according to the methods of Scheme A and/or B. Materials used herein are either commercially available or prepared by synthetic methods generally known in the art. These schemes are not limited to the compounds listed or by any particular substituents, which are employed for illustrative purposes. Although various steps of are described and depicted in Scheme A and/or B, the steps in some cases may be performed in a different order than the order shown in Scheme A and/or B. Various modifications to these synthetic reaction schemes may be made and will be suggested to one skilled in the art having referred to the disclosure contained in this Application. Numbering does not necessarily correspond to that of claims or other tables.

Scheme A

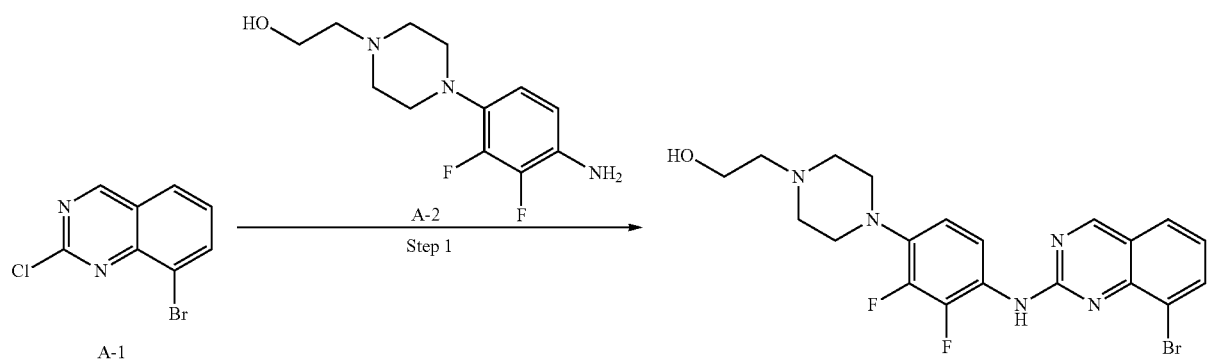

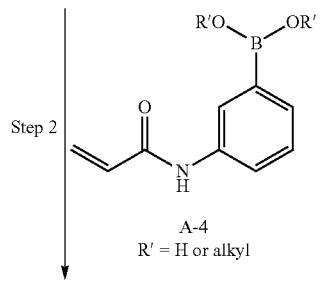

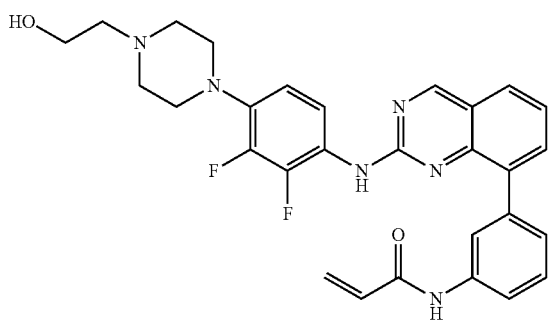

Formula I

In Scheme A, A-1 is reacted with A-2 in the presence of a base. Suitable bases include Cs$_2$CO$_3$, NaH, KH, t-BuOK, LiH, and CaH$_2$. Suitable solvents include, but are not limited to, DMF, DMSO, DMA, and N-methyl piperidone. The reaction are generally carried out at a temperature ranging from 25 to 240° C. Suzuki cross-coupling reaction of A-3 with boronic acid or ester A-4 in the presence of a base, such as Na$_2$CO$_3$, K$_2$CO$_3$, Cs$_2$CO$_3$, and a Pd catalyst, gives compound of Formula I. The reaction is generally carried out at a temperature ranging from 25 to 180° C. in a suitable solvent such as 1,4-dioxane, water, tetrahydrofuran, or a mixture thereof.

In Scheme B, compound A-2 is reacted with compound A-5 in presence of an acid, for example HCl, H$_2$SO$_4$ or TFA. Suitable solvent for the reaction include organic alcohol solvents, for example methanol, ethanol, isopropanol, butanol or mixtures thereof. The reaction is generally carried out at a temperature ranging from 25 to 240° C., for example at 80-100° C.

Scheme B

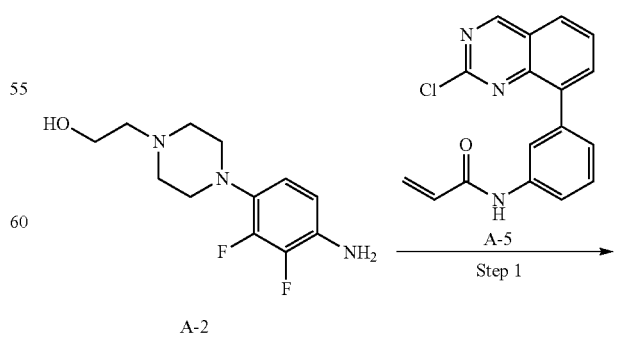

-continued

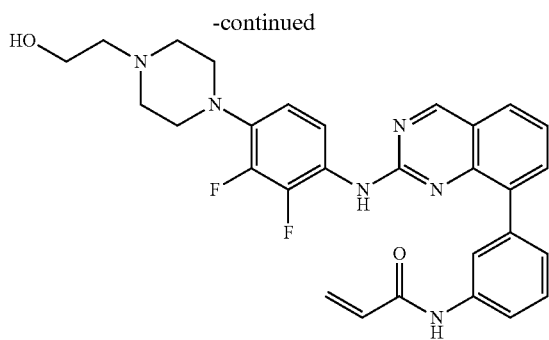

Formula I

The polymorphs according to the invention are not limited by the starting materials used to produce the compound of Formula I.

In one aspect, the invention is directed to methods of making polymorphs of the compound of the Formula I or a pharmaceutically acceptable salt and/or solvate thereof either by isolation of the desired polymorph as the first solid form after synthesis of the compound of Formula I, or alternatively, by isolation of the desired polymorph as a transition from a prior solid form of the compound of Formula I. Transitions from one form to another are within the scope of the invention because they can be an alternative manufacturing method for obtaining the form desired for the production of the medicinal preparations.

Polymorphs of the compound of Formula I, according to the methods of the invention can be selected from Form I, Form II, Form III, Form IV, Form V, Form VI, Form VIII, and mixtures thereof.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples below. However, other equivalent separation or isolation procedures can also be used. Prior to crystallization, the compound of Formula I may be isolated in about 50% chemical purity, 55% chemical purity, 60% chemical purity, 65% chemical purity, 70% chemical purity, 75% chemical purity, 80% chemical purity, 90% chemical purity, 91% chemical purity, 92% purity, 93% chemical purity, 94% chemical purity, 95% chemical purity, 96% chemical purity, 97% chemical purity, 98% chemical purity, 99% chemical purity, about 98% chemical purity, or about 100% chemical purity.

In some embodiments, the crystalline forms disclosed herein are obtained by crystallizing the compound of Formula I with a chemical purity of less than about 98%, less than about 97%, less than about 96%, less than about 95%, less than about 94%, less than about 93%, less than about 92%, less than about 91%, less than about 90%, less than about 89%, less than about 88%, less than about 87%, less than about 86%, less than about 85%, less than about 84%, less than about 83%, less than about 82%, less than about 81%, less than about 80%, less than about 78%, less than about 76%, less than about 74%, less than about 72%, or less than about 70%. In some embodiments, the crystalline forms are obtained by crystallizing a compound of Formula I with a chemical purity in the range of about 70% to about 99%, 80% to about 96%, about 85% to about 96%, about 90% to about 96%, about 80% to 98%, about 85% to about 98%, about 90% to about 98%, about 92% to about 98%, about 94% to 98%, or about 96% to about 98%.

In various embodiments, the various polymorph Forms disclosed herein (e.g. Forms I-VI and Form VIII of the compound of Formula I) are stable at room temperature. In some examples, the various polymorphs can be stored at room temperature for an extended period of time without significant chemical degradation or change in the crystalline form. In some examples, the various polymorphs can be stored at room temperature for a time period of at least about 10 days, 30 days, 60 days, 90 days, or 120 days. In some examples, the various polymorphs can be stored at room temperature for a time period of at most about 120 days. In some examples, the various polymorphs can be stored at room temperature for a time period of 10-14 days, 10-18 days, 10-22 days, 10-26 days, 10-30 days, 10-40 days, 10-50 days, 10-60 days, 10-90 days, 10-120 days, 14-18 days, 14-22 days, 14-26 days, 14-30 days, 14-40 days, 14-50 days, 14-60 days, 14-90 days, 14-120 days, 18-22 days, 18-26 days, 18-30 days, 18-40 days, 18-50 days, 18-60 days, 18-90 days, 18-120 days, 22-26 days, 22-30 days, 22-40 days, 22-50 days, 22-60 days, 22-90 days, 22-120 days, 26-30 days, 26-40 days, 26-50 days, 26-60 days, 26-90 days, 26-120 days, 30-40 days, 30-50 days, 30-60 days, 30-90 days, 30-120 days, 40-50 days, 40-60 days, 40-90 days, 40-120 days, 50-60 days, 50-90 days, 50-120 days, 60-90 days, 60-120 days, or 90-120 days. In some examples, the various polymorphs can be stored at room temperature for a time period of at least 10 days, 14 days, 18 days, 22 days, 26 days, 30 days, 40 days, 50 days, 60 days, 90 days, or 120 days.

In various embodiments, the various polymorph Forms disclosed herein (e.g. Forms I-VI and Form VIII of the compound of Formula I) are stable at temperatures above the room temperature and/or at high relative humidity (RH). In some examples, the various polymorph Forms disclosed herein (e.g. Forms I-VI and Form VIII of the compound of Formula I) can be stored at about 40° C. at about 75% RH for an extended period of time without significant chemical degradation or change in the crystalline form. In some examples, the various polymorph Forms disclosed herein (e.g. Forms I-VI and Form VIII of the compound of Formula I) can be stored at 40° C. and at about 75% RH for a time period of at least about 10 days, 30 days, 60 days, 90 days, or 120 days. In some examples, the various polymorph Forms disclosed herein (e.g. Forms I-VI and Form VIII of the compound of Formula I) can be stored at 40° C. and at about 75% RH for a time period of at most about 120 days. In some examples, the various polymorph Forms disclosed herein (e.g. Forms I-VI and Form VIII of the compound of Formula I) can be stored at 40° C. and at about 75% RH for a time period of 10-14 days, 10-18 days, 10-22 days, 10-26 days, 10-30 days, 10-40 days, 10-50 days, 10-60 days, 10-90 days, 10-120 days, 14-18 days, 14-22 days, 14-26 days, 14-30 days, 14-40 days, 14-50 days, 14-60 days, 14-90 days, 14-120 days, 18-22 days, 18-26 days, 18-30 days, 18-40 days, 18-50 days, 18-60 days, 18-90 days, 18-120 days, 22-26 days, 22-30 days, 22-40 days, 22-50 days, 22-60 days, 22-90 days, 22-120 days, 26-30 days, 26-40 days, 26-50 days, 26-60 days, 26-90 days, 26-120 days, 30-40 days, 30-50 days, 30-60 days, 30-90 days, 30-120 days, 40-50 days, 40-60 days, 40-90 days, 40-120 days, 50-60 days, 50-90 days, 50-120 days, 60-90 days, 60-120 days, or 90-120 days. In some examples, the various polymorph Forms disclosed herein (e.g. Forms I-VI and Form VIII of the compound of Formula I) can be stored at 40° C. at about 75% RH for a time period of at least 10 days, 14 days, 18 days, 22 days, 26 days, 30 days, 40 days, 50 days, 60 days, 90 days, or 120 days.

In some examples, the various polymorph Forms disclosed herein (e.g. Forms I-VI and Form VIII of the compound of Formula I) can be stored at about 60° C. for an extended period of time without significant chemical degradation or change in the crystalline form. In some examples, various polymorph Forms disclosed herein (e.g. Forms I-VI and Form VIII of the compound of Formula I) can be stored at 60° C. for a time period of at least about 10 days, 30 days, 60 days, 90 days, or 120 days. In some examples, the various polymorph Forms disclosed herein (e.g. Forms I-VI and Form VIII of the compound of Formula I) can be stored at 60° C. for a time period of at most about 120 days. In some examples, the various polymorph Forms disclosed herein (e.g. Forms I-VI and Form VIII of the compound of Formula I) can be stored at 60° C. for a time period of 10-14 days, 10-18 days, 10-22 days, 10-26 days, 10-30 days, 10-40 days, 10-50 days, 10-60 days, 10-90 days, 10-120 days, 14-18 days, 14-22 days, 14-26 days, 14-30 days, 14-40 days, 14-50 days, 14-60 days, 14-90 days, 14-120 days, 18-22 days, 18-26 days, 18-30 days, 18-40 days, 18-50 days, 18-60 days, 18-90 days, 18-120 days, 22-26 days, 22-30 days, 22-40 days, 22-50 days, 22-60 days, 22-90 days, 22-120 days, 26-30 days, 26-40 days, 26-50 days, 26-60 days, 26-90 days, 26-120 days, 30-40 days, 30-50 days, 30-60 days, 30-90 days, 30-120 days, 40-50 days, 40-60 days, 40-90 days, 40-120 days, 50-60 days, 50-90 days, 50-120 days, 60-90 days, 60-120 days, or 90-120 days. In some examples, the various polymorph Forms disclosed herein (e.g. Forms I-VI and Form VIII of the compound of Formula I) can be stored at 60° C. for a time period of at least 10 days, 14 days, 18 days, 22 days, 26 days, 30 days, 40 days, 50 days, 60 days, 90 days, or 120 days.

In some examples, the various polymorph Forms disclosed herein (e.g. Forms I-VI and Form VIII of the compound of Formula I) can be stored at about 70° C., 80° C., 90° C., or 100° C. for an extended period of time without significant chemical degradation or change in the crystalline form. In some examples, the various polymorph Forms disclosed herein can be stored at about 70° C., 80° C., 90° C., or 100° C. for a time period of at least about 10 days, 30 days, 60 days, 90 days, or 120 days. In some examples, the various polymorph Forms disclosed herein can be stored at about 70° C., 80° C., 90° C., or 100° C. for a time period of at most about 120 days. In some examples, the various polymorph Forms disclosed herein can be stored at about 70° C., 80° C., 90° C., or 100° C. for a time period of 10-14 days, 10-18 days, 10-22 days, 10-26 days, 10-30 days, 10-40 days, 10-50 days, 10-60 days, 10-90 days, 10-120 days, 14-18 days, 14-22 days, 14-26 days, 14-30 days, 14-40 days, 14-50 days, 14-60 days, 14-90 days, 14-120 days, 18-22 days, 18-26 days, 18-30 days, 18-40 days, 18-50 days, 18-60 days, 18-90 days, 18-120 days, 22-26 days, 22-30 days, 22-40 days, 22-50 days, 22-60 days, 22-90 days, 22-120 days, 26-30 days, 26-40 days, 26-50 days, 26-60 days, 26-90 days, 26-120 days, 30-40 days, 30-50 days, 30-60 days, 30-90 days, 30-120 days, 40-50 days, 40-60 days, 40-90 days, 40-120 days, 50-60 days, 50-90 days, 50-120 days, 60-90 days, 60-120 days, or 90-120 days. In some examples, the various polymorph Forms disclosed herein can be stored at about 70° C., 80° C., 90° C., or 100° C. for a time period of at least 10 days, 14 days, 18 days, 22 days, 26 days, 30 days, 40 days, 50 days, 60 days, 90 days, or 120 days.

Polymorph Form I of the Compound of Formula I:

FIG. 1 shows the XRPD for the polymorph Form I of the compound of Formula I.

FIG. 2 shows an exemplary DSC thermogram of the polymorph Form I of the compound of Formula I.

Figure 3:
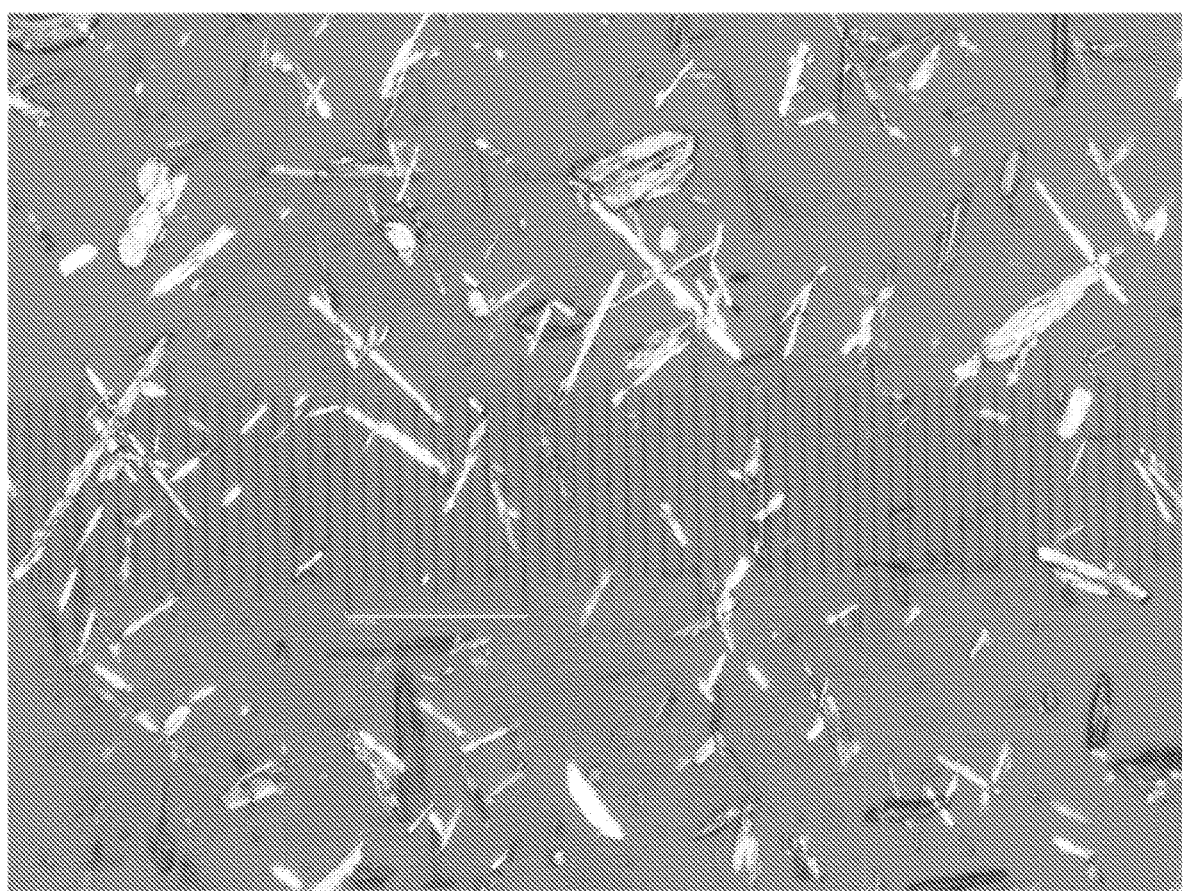
FIG. 3 shows microphotograph of the polymorph Form I of the compound of Formula I.

FIG. 3 shows microphotograph of the polymorph Form I of the compound of Formula I.

FIG. 4 shows the DVS isothermal sorption and desorption curves for the polymorph Form I of the compound of Formula I.

In one embodiment, the desired polymorph is Form I of the compound of Formula I, and the isolating step involves recrystallization of crude reaction product from a mono-solvent system. In various embodiments, the desired polymorph is Form I of the compound of Formula I, and the isolating step involves recrystallization of crude product from a binary, tertiary, or greater solvent system, collectively understood as a multi-solvent system. In various embodiments, the desired polymorph is Form I of the compound of Formula I, and the isolating step involves crystallization from a mono- or multi-solvent system, where the crystallization involves dissolving the compound of Formula I in the mono- or multi-solvent system at a temperature above ambient temperature. In some examples, the dissolving of the compound of Formula I in the mono- or multi-solvent system is performed at a temperature of about 40-90° C., 45-90° C., 50-90° C., 55-90° C., 60-90° C., 65-90° C., 70-90° C., 75-90° C., 40-85° C., 45-85° C., 50-85° C., 55-85° C., 60-85° C., 65-85° C., 70-85° C., 75-85° C., 80-85° C., 40-80° C., 45-80° C., 50-80° C., 55-80° C., 60-80° C., 65-80° C., 70-80° C., 75-80° C., 40-75° C., 45-75° C., 50-75° C., 55-75° C., 60-75° C., 65-75° C., 70-75° C., 40-70° C., 45-70° C., 50-70° C., 55-70° C., 60-70° C., 65-70° C., 40-65° C., 45-65° C., 50-65° C., 55-65° C., 60-65° C., 40-60° C., 45-60° C., 50-60° C., 55-60° C., 40-55° C., 45-55° C., 50-55° C., 40-50° C., or 45-50° C. In some examples, the recrystallization solvent comprises ethyl acetate and the dissolving of the compound of Formula I in the solvent is performed at a temperature of about 55-65° C. Any suitable amount of solvent can be used for dissolving the compound of Formula I. In some embodiments, the amount of solvent (e.g. ethyl acetate) used to dissolve the compound is from about 300-100 mL per gram of the compound of Formula I. For example, in some embodiments, the amount of solvent used for dissolving the compound of Formula I is 100 mL per gram of the compound of Formula I. In some examples, the recrystallization solvent comprises ethyl acetate, the dissolving of the compound of Formula I in the solvent system is performed at a temperature of about 55-65° C., and the amount of solvent used for dissolving is about 100 mL/g of the compound of Formula I.

In various embodiments, the crystallization further comprises filtration of the solution containing the dissolved compound of Formula I. Filtration may be performed by any suitable means, for example via a silica gel pad. The silica gel pad may further be washed with the recrystallization solvent one or multiple times (for example once, twice, thrice or more). The filtrate obtained from the filtration may optionally be concentrated. In some embodiments the concentration is performed under vacuum at a temperature of about 10-60° C., for example at a temperature of about 10-50° C., 10-40° C., 10-30° C., 10-20° C., 20-60° C., 20-50° C., 20-40° C., 20-30° C., 30-60° C., 30-50° C., 30-40° C., 30-60° C., 30-50° C., 30-40° C., 20-30° C. and 10-20° C. In some embodiments, concentration is performed under vacuum at a temperature of about 30-40° C. The concentration of Formula I in the filtrate after concentration can be between 10-30 gram of the compound of Formula I per liter of solvent, for example about 10 g/L, 12 g/L, 14 g/L, 16 g/L, 18 g/L, 20 g/L, 22 g/L, 24 g/L, 26 g/L, 28 g/L, or 30 g/mL. In some embodiments, the solvent is ethyl acetate and the concentration of the compound of Formula I after filtration and concentration is about 12.5 g/L.

In various embodiments, the crystallization further involves actively heating the solution containing the dissolved compound of Formula I, for example to a temperature of about 40-100° C., 40-90° C., 40-80° C., 40-70° C., 40-60° C., 40-50° C., 50-100° C., 50-90° C., 50-80° C., 50-70° C., 50-60° C., 60-100° C., 60-90° C., 60-80° C., 60-70° C., 70-100° C., 70-90° C., 70-80° C., 80-100° C., or 80-90° C. In some embodiments, the solution containing the dissolved compound of Formula I, is heated to a temperature of about 75-85° C. In various embodiments, the solution containing the dissolved compound of Formula I is maintained at the heated temperature for a period of time, for example for about 30 min, about 1 h, about 2 h, about 3 h, about 4 h, about 5 h, about 6 h, about 7 h, about 8 h, about 9 h, about 10 h, about 11 h, about 12 h, about 13 h, about 14 h, about 15 h, about 16 h, about 17 h, about 18 h, about 19 h, about 20 h, about 21 h, about 22 h, about 23 h, about 24 h or more.

In various embodiments, the crystallization further involves actively cooling the heated solution containing the dissolved compound of Formula I, for example to a temperature of about 10-70° C., 10-60° C., 10-50° C., 10-40° C., 10-30° C., 10-20° C., 20-70° C., 20-60° C., 20-50° C., 20-40° C., 20-30° C., 30-70° C., 30-60° C., 30-50° C., 30-40° C., 40-70° C., 40-60° C., 40-50° C., 50-70° C., 50-60° C., or 60-70° C. In some embodiments, the crystallization further involves actively cooling the heated solution containing the dissolved compound of Formula I to a temperature of about 50-60° C. In various embodiments, the solution containing the dissolved compound of Formula I is further maintained at this lower temperature for a time period, for example for about 30 min, about 1 h, about 2 h, about 3 h, about 4 h, about 5 h, about 6 h, about 7 h, about 8 h, about 9 h, about 10 h, about 11 h, about 12 h, about 13 h, about 14 h, about 15 h, about 16 h, about 17 h, about 18 h, about 19 h, about 20 h, about 21 h, about 22 h, about 23 h, about 24 h or more. In some embodiments, the crystallization further involves actively cooling the heated solution containing the dissolved compound of Formula I to a temperature of about 50-60° C. and maintaining the solution at this temperature for about 2 hours.

In various embodiments, the steps of active heating followed by active cooling are repeated multiple times, for example at least 2, at least 3, at least 4, at least 5, at least 6, at least 7, at least 8, at least 9, or at least 10 times. In some embodiments, the steps of active heating followed by active cooling are repeated 2, 3, 4, 5, 6, 7, 8, 9, or 10 times. In some embodiments, the heating followed by cooling steps are repeated 2 times.

In various embodiments, the solution of compound of Formula I obtained after the active heating and/or active cooling is further cooled to a temperature of about 0-40° C., 0-30° C., 0-20° C., 0-10° C., 10-40° C., 10-30° C., 10-20° C., 20-40° C., 20-30° C., 20-10° C., or 30° C.-40° C. In some embodiments, the solution containing the dissolved compound of Formula I is cooled to a temperature of about 20-30° C. In various embodiments, the solution containing the dissolved compound of Formula I is maintained at this lower temperature for a time period, for example for about 30 min, about 1 h, about 2 h, about 3 h, about 4 h, about 5 h, about 6 h, about 7 h, about 8 h, about 9 h, about 10 h, about 11 h, about 12 h, about 13 h, about 14 h, about 15 h, about 16 h, about 17 h, about 18 h, about 19 h, about 20 h, about 21 h, about 22 h, about 23 h, about 24 h or more. In some embodiments, the solution containing the dissolved compound of Formula I is cooled to a temperature of about 20-30° C. and maintained at this temperature for about 3 hours.

In various embodiments, the crystallization further involves filtering the solution containing the obtained crystals of the compound of Formula I. In some embodiments, the crystallization optionally involves washing the obtained crystals by a solvent, for example by the recrystallization solvent one or more times. In some embodiments, the crystallization optionally involves drying the obtained crystals, for example under vacuum at a temperature of about 30-40° C.

In some embodiments, the Form I is non-micronized. In some embodiments a majority of particles in the non-micronized polymorph Form I, for example greater than 60%, 70%, 80%, 90%, or 95% of particles in the polymorph I are smaller than about 5 μm in diameter, about 10 μm in diameter, about 15 μm in diameter, about 20 μm in diameter, about 25 μm in diameter, about 30 μm in diameter, about 35 μm in diameter, about 40 μm in diameter, about 45 μm in diameter, about 50 μm in diameter, about 55 μm in diameter, about 60 μm in diameter, about 65 μm in diameter, about 70 μm in diameter, about 75 μm in diameter, about 80 μm in diameter, about 85 μm in diameter, about 95 μm in diameter, about 100 μm in diameter, about 110 μm in diameter, about 120 μm in diameter, about 130 μm in diameter, about 140 μm in diameter, about 150 μm in diameter, about 160 μm in diameter, about 170 μm in diameter, about 180 μm in diameter, about 190 μm in diameter, about 200 μm in diameter, about 210 μm in diameter, about 220 μm in diameter, about 230 μm in diameter, about 240 μm in diameter, about 250 μm in diameter, about 260 μm in diameter, about 270 μm in diameter, about 280 μm in diameter, about 290 μm in diameter, or about 300 μm in diameter. In some examples 60%, 70%, 80%, 90%, or 95% of the particles in non-micronized Form I have a diameter less than about 100 μm.

In some embodiments, the Form I is micronized. In some embodiments a majority of particles in the micronized polymorph Form I, for example greater than 60%, 70%, 80%, 90%, or 95% of particles in the polymorph Form I are smaller than about 5 μm in diameter, about 10 μm in diameter, about 15 μm in diameter, about 20 μm in diameter, about 25 μm in diameter, about 30 μm in diameter, about 35 μm in diameter, about 40 μm in diameter, about 45 μm in diameter, about 50 μm in diameter, about 55 μm in diameter, about 60 μm in diameter, about 65 μm in diameter, about 70 μm in diameter, about 75 μm in diameter, about 80 μm in diameter, about 85 μm in diameter, about 95 μm in diameter, about 100 μm in diameter, about 110 μm in diameter, about 120 μm in diameter, about 130 μm in diameter, about 140 μm in diameter, about 150 μm in diameter, about 160 μm in diameter, about 170 μm in diameter, about 180 μm in diameter, about 190 μm in diameter, about 200 μm in diameter, about 210 μm in diameter, about 220 μm in diameter, about 230 μm in diameter, about 240 μm in diameter, about 250 μm in diameter, about 260 μm in diameter, about 270 μm in diameter, about 280 μm in diameter, about 290 μm in diameter, or about 300 μm in diameter. In some examples 60%, 70%, 80%, 90%, or 95% of the particles in micronized Form I have a diameter less than about 5 μm. In some examples 60%, 70%, 80%, 90%, or 95% of the particles in micronized Form I have a diameter less than 10 µm. In some examples 60%, 70%, 80%, 90%, or 95% of the particles in micronized Form I have a diameter less than 20 µm.

In some embodiments, the chemical purity of the polymorph Form I is greater than 60%, 70%, 80%, 90%, 95%, or 99%. In some embodiments, the chemical purity of the polymorph Form I is greater than about 90%. In some embodiments, the chemical purity of the polymorph Form I is greater than about 95%. In some embodiments, the chemical purity of the polymorph Form I greater than about 99%. The chemical purity of polymorph Form I may be measured by any available analytical technique, for example by HPLC analysis.

In various embodiments, the polymorph Form I is dry. In various embodiments, the polymorph Form I is non-solvated. In various embodiments, the polymorph Form I is non-hydrated.

In various embodiments, the polymorph Form I is non-hygroscopic. In some examples, the polymorph Form I gains between 0.01-10% weight at a RH of 70-90%. In some examples, the Form I gains between 0.01-10% weight, for example between 0.01-0.1%, 0.01-1%, 01-2%, 0.01-3%, 0.01-4%, 0.01-5%, 0.1-1%, 0.1-2%, 0.1-3%, 0.1-4%, 0.1-5%, 1-2%, 1-3%, 1-4%, 1-5%, 2-3%, 2-4%, 2-5%, 3-4%, 3-5%, or 4-5% weight at a RH of 80%.

In various embodiments, the polymorph Form I is characterized by an endotherm at about 160-180° C., 162-180° C., 164-180° C., 166-180° C., 168-180° C., 170-180° C., 172-180° C., 174-180° C., 160-178° C., 162-178° C., 164-178° C., 166-178° C., 168-178° C., 170-178° C., 172-178° C., 174-178° C., 160-176° C., 162-176° C., 164-176° C., 166-176° C., 168-176° C., 170-176° C., 172-176° C., 174-176° C., 160-174° C., 162-174° C., 164-174° C., 166-174° C., 168-174° C., 170-174° C., 172-174° C., 160-172° C., 162-172° C., 164-172° C., 166-172° C., 168-172° C., 170-172° C., 160-170° C., 162-170° C., 164-170° C., 166-170° C., 168-170° C., 160-168° C., 162-168° C., 164-168° C., 166-168° C., 160-166° C., 162-166° C., 164-166° C., 160-164° C., 162-164° C., 160-162° C. in the DSC trace. In various embodiments, the polymorph Form I is characterized by an endotherm at about 165-175° C. in the DSC trace, for example about 165° C., 166° C., 167° C., 168° C., 169° C., 170° C., 171° C., 172° C., 173° C., 174° C. or 175° C. In some embodiments, the melting point of the polymorph Form I is about 173° C.

In various embodiments, the polymorph Form I decomposes above a temperature of about 200° C., about 250° C., about 300° C., about 350° C., about 400° C., about 450° C., about 500° C., about 550° C. or above 600° C. In some examples, the polymorph Form I decomposes above a temperature of about 250° C.

In various embodiments, the polymorph Form I is stable at room temperature. In some examples, the polymorph Form I can be stored at room temperature for extended period of time without significant chemical degradation or change in the crystalline form. In some examples, the polymorph Form I can be stored at room temperature for a time period of at least about 10 days, 30 days, 60 days, 90 days, or 120 days. In some examples, the polymorph Form I can be stored at room temperature for a time period of at most about 120 days. In some examples, the polymorph Form I can be stored at room temperature for a time period of 10-14 days, 10-18 days, 10-22 days, 10-26 days, 10-30 days, 10-40 days, 10-50 days, 10-60 days, 10-90 days, 10-120 days, 14-18 days, 14-22 days, 14-26 days, 14-30 days, 14-40 days, 14-50 days, 14-60 days, 14-90 days, 14-120 days, 18-22 days, 18-26 days, 18-30 days, 18-40 days, 18-50 days, 18-60 days, 18-90 days, 18-120 days, 22-26 days, 22-30 days, 22-40 days, 22-50 days, 22-60 days, 22-90 days, 22-120 days, 26-30 days, 26-40 days, 26-50 days, 26-60 days, 26-90 days, 26-120 days, 30-40 days, 30-50 days, 30-60 days, 30-90 days, 30-120 days, 40-50 days, 40-60 days, 40-90 days, 40-120 days, 50-60 days, 50-90 days, 50-120 days, 60-90 days, 60-120 days, or 90-120 days. In some examples, the polymorph Form I can be stored at room temperature for a time period of at least 10 days, 14 days, 18 days, 22 days, 26 days, 30 days, 40 days, 50 days, 60 days, 90 days, or 120 days.

In various embodiments, the polymorph Form I is stable at temperatures above the room temperature and/or at high RH. In some examples, the polymorph Form I can be stored at about 40° C. at about 75% RH for an extended period of time without significant chemical degradation or change in the crystalline form. In some examples, the polymorph Form I can be stored at 40° C. and at about 75% RH for a time period of at least about 10 days, 30 days, 60 days, 90 days, or 120 days. In some examples, the polymorph Form I can be stored at 40° C. and at about 75% RH for a time period of at most about 120 days. In some examples, the polymorph Form I can be stored at 40° C. and at about 75% RH for a time period of 10-14 days, 10-18 days, 10-22 days, 10-26 days, 10-30 days, 10-40 days, 10-50 days, 10-60 days, 10-90 days, 10-120 days, 14-18 days, 14-22 days, 14-26 days, 14-30 days, 14-40 days, 14-50 days, 14-60 days, 14-90 days, 14-120 days, 18-22 days, 18-26 days, 18-30 days, 18-40 days, 18-50 days, 18-60 days, 18-90 days, 18-120 days, 22-26 days, 22-30 days, 22-40 days, 22-50 days, 22-60 days, 22-90 days, 22-120 days, 26-30 days, 26-40 days, 26-50 days, 26-60 days, 26-90 days, 26-120 days, 30-40 days, 30-50 days, 30-60 days, 30-90 days, 30-120 days, 40-50 days, 40-60 days, 40-90 days, 40-120 days, 50-60 days, 50-90 days, 50-120 days, 60-90 days, 60-120 days, or 90-120 days. In some examples, the polymorph Form I can be stored at 40° C. at about 75% RH for a time period of at least 10 days, 14 days, 18 days, 22 days, 26 days, 30 days, 40 days, 50 days, 60 days, 90 days, or 120 days.

In some examples, the polymorph Form I can be stored at about 60° C. for an extended period of time without significant chemical degradation or change in the crystalline form. In some examples, the polymorph Form I can be stored at 60° C. for a time period of at least about 10 days, 30 days, 60 days, 90 days, or 120 days. In some examples, the polymorph Form I can be stored at 60° C. for a time period of at most about 120 days. In some examples, the polymorph Form I can be stored at 60° C. for a time period of 10-14 days, 10-18 days, 10-22 days, 10-26 days, 10-30 days, 10-40 days, 10-50 days, 10-60 days, 10-90 days, 10-120 days, 14-18 days, 14-22 days, 14-26 days, 14-30 days, 14-40 days, 14-50 days, 14-60 days, 14-90 days, 14-120 days, 18-22 days, 18-26 days, 18-30 days, 18-40 days, 18-50 days, 18-60 days, 18-90 days, 18-120 days, 22-26 days, 22-30 days, 22-40 days, 22-50 days, 22-60 days, 22-90 days, 22-120 days, 26-30 days, 26-40 days, 26-50 days, 26-60 days, 26-90 days, 26-120 days, 30-40 days, 30-50 days, 30-60 days, 30-90 days, 30-120 days, 40-50 days, 40-60 days, 40-90 days, 40-120 days, 50-60 days, 50-90 days, 50-120 days, 60-90 days, 60-120 days, or 90-120 days. In some examples, the polymorph Form I can be stored at 60° C. for a time period of at least 10 days, 14 days, 18 days, 22 days, 26 days, 30 days, 40 days, 50 days, 60 days, 90 days, or 120 days.

In some examples, the polymorph Form I can be stored at about 100° C. for an extended period of time without significant chemical degradation or change in the crystalline form. In some examples, the polymorph Form I can be stored at 100° C. for a time period of at least about 10 days, 30 days, 60 days, 90 days, or 120 days. In some examples, the polymorph Form I can be stored at 100° C. for a time period of at most about 120 days. In some examples, the polymorph Form I can be stored at 100° C. for a time period of 10-14 days, 10-18 days, 10-22 days, 10-26 days, 10-30 days, 10-40 days, 10-50 days, 10-60 days, 10-90 days, 10-120 days, 14-18 days, 14-22 days, 14-26 days, 14-30 days, 14-40 days, 14-50 days, 14-60 days, 14-90 days, 14-120 days, 18-22 days, 18-26 days, 18-30 days, 18-40 days, 18-50 days, 18-60 days, 18-90 days, 18-120 days, 22-26 days, 22-30 days, 22-40 days, 22-50 days, 22-60 days, 22-90 days, 22-120 days, 26-30 days, 26-40 days, 26-50 days, 26-60 days, 26-90 days, 26-120 days, 30-40 days, 30-50 days, 30-60 days, 30-90 days, 30-120 days, 40-50 days, 40-60 days, 40-90 days, 40-120 days, 50-60 days, 50-90 days, 50-120 days, 60-90 days, 60-120 days, or 90-120 days. In some examples, the polymorph Form I can be stored at 100° C. for a time period of at least 10 days, 14 days, 18 days, 22 days, 26 days, 30 days, 40 days, 50 days, 60 days, 90 days, or 120 days.

Polymorph Form II of the Compound of Formula I

Figure 5:
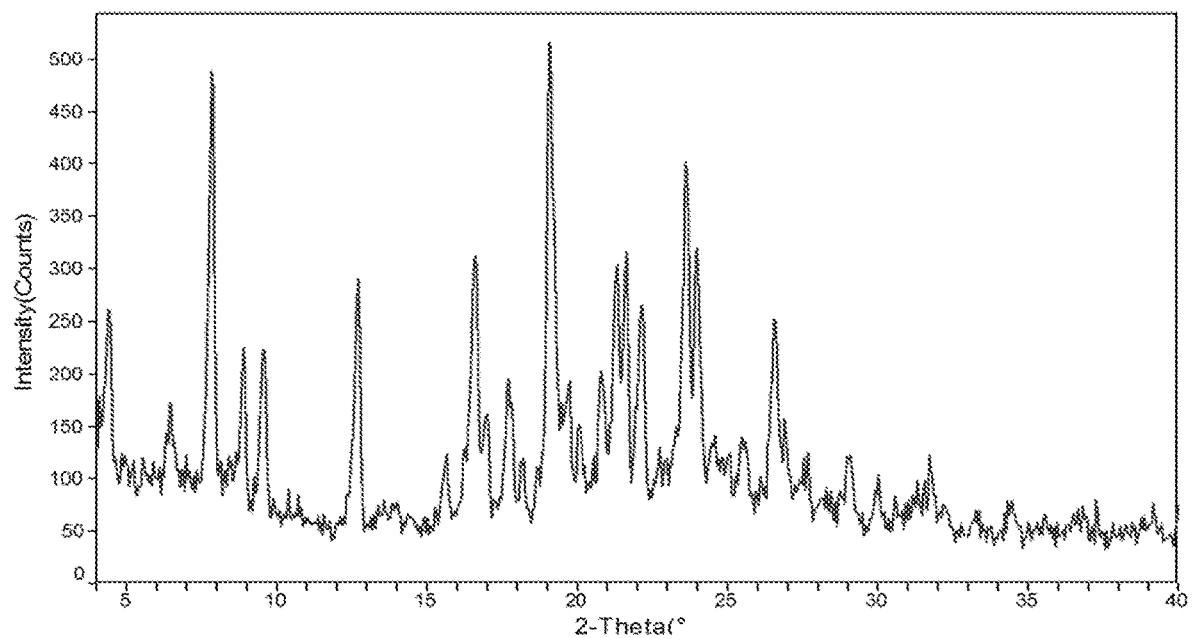
FIG. 5 shows the XRPD for polymorph Form II of the compound of Formula I.

FIG. 5 shows the X-ray powder diffraction (XRPD) for Polymorph Form II.

Figure 6:
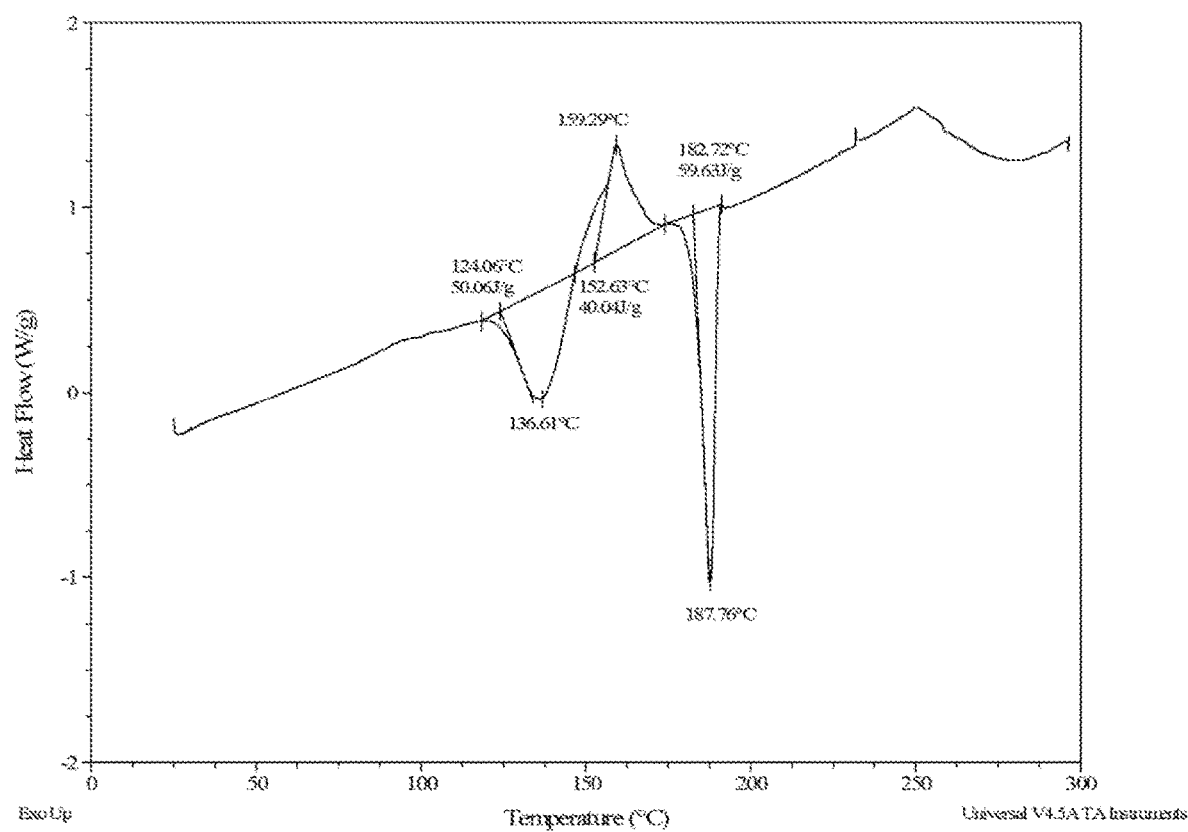
FIG. 6 shows an exemplary DSC thermogram of the polymorph Form II of the compound of Formula I.

FIG. 6 shows an exemplary DSC thermogram of Form II.

In one embodiment, the desired polymorph is Form II of the compound of Formula I, and the isolating step involves recrystallization of crude reaction product from a mono-solvent system. In various embodiments, the desired polymorph is Form II of the compound of Formula I, and the isolating step involves recrystallization of crude product from a binary, tertiary, or greater solvent system, collectively understood as a multi-solvent system. In various embodiments, the desired polymorph is Form II of the compound of Formula I, and the isolating step involves crystallization from a mono- or multi-solvent system, where the crystallization involves dissolving the compound of Formula I in the mono- or multi-solvent system at a temperature above ambient temperature.

In some embodiments, the chemical purity of the polymorph Form II is greater than 60%, 70%, 80%, 90%, 95%, or 99%. In some embodiments, the chemical purity of the polymorph Form II is greater than about 90%. In some embodiments, the chemical purity of the polymorph Form II is greater than about 95%. In some embodiments, the chemical purity of the polymorph Form II greater than about 99%. The chemical purity of polymorph Form II may be measured by any available analytical technique, for example by HPLC analysis.

In various embodiments, the polymorph Form II is characterized by an endotherm in the range of about 120-150° C., for example at about 120-145° C., 120-140° C., 120-135° C., 120-130° C., 125-145° C., 125-140° C., 125-135° C., 125-130° C., 130-150° C., 130-145° C., 130-140° C., 130-135° C., 135-150° C., 135-145° C., 135-140° C., 140-150° C., 140-145° C., or 145-150° C. in the DSC trace. In some examples, the polymorph Form II is characterized by an endotherm at about 124° C. in the DSC trace.

In various embodiments, the polymorph Form II is further characterized by an endotherm in the range of about 175-200° C., for example at about 175-195° C., 175-190° C., 175-185° C., 175-180° C., 180-200° C., 180-195° C., 180-190° C., 180-185° C., 185-200° C., 185-195° C., 185-190° C., 190-195° C., or 195-200° C. in the DSC trace. In some examples, the polymorph Form II is further characterized by an endotherm at about 183° C. in the DSC trace.

Polymorph Form III of the Compound of Formula I

Figure 7:
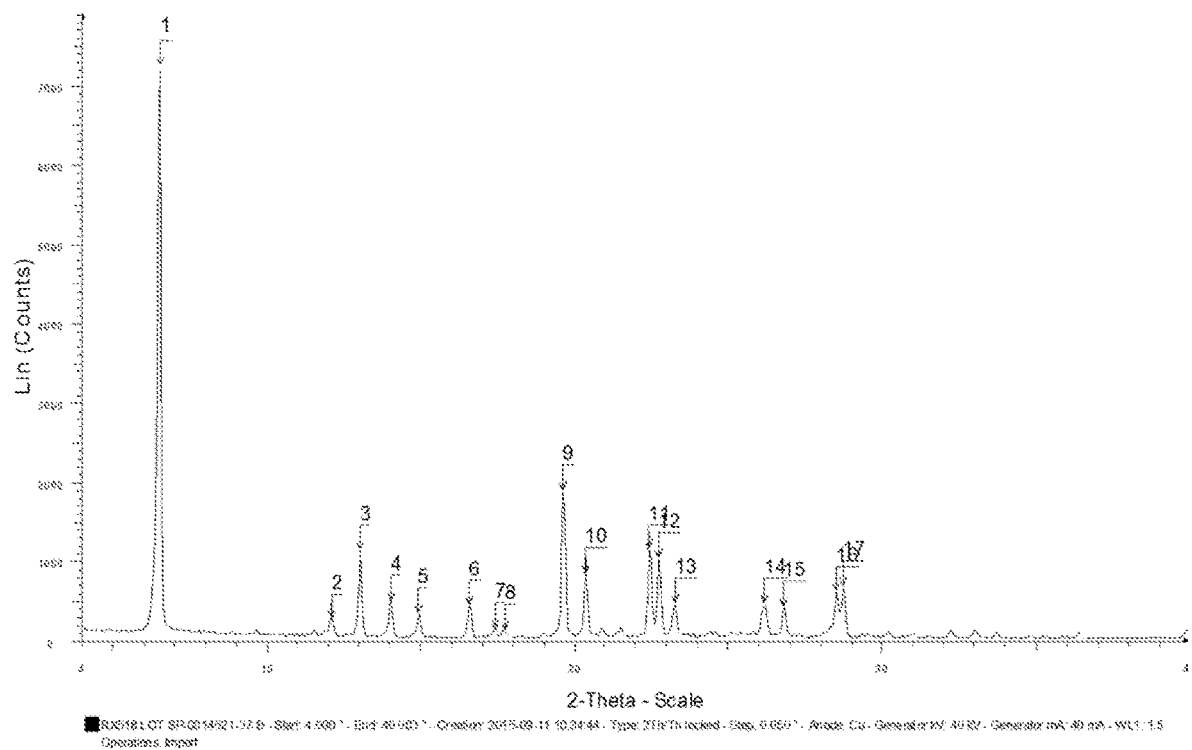
FIG. 7 shows the XRPD for polymorph Form III of the compound of Formula I.

FIG. 7 shows the XRPD for Polymorph Form III.

Figure 8:
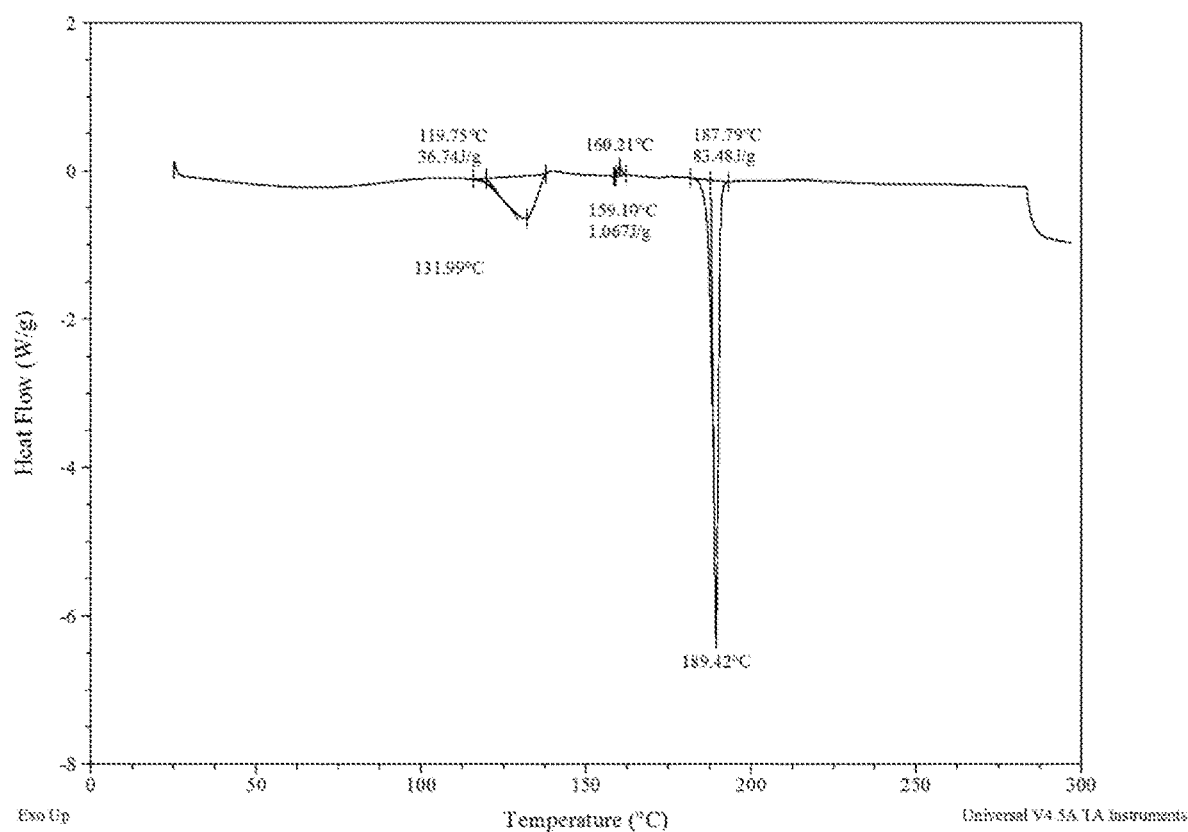
FIG. 8 shows an exemplary DSC thermogram of the polymorph Form III of the compound of Formula I.

FIG. 8 shows an exemplary DSC thermogram of Form III.

In various embodiments, the desired polymorph is Form III of the compound of Formula I, and the isolating step involves recrystallization of crude reaction product from a mono-solvent system. In various embodiments, the desired polymorph is Form III of the compound of Formula I, and the isolating step involves recrystallization of crude product from a binary, tertiary, or greater solvent system, where binary, tertiary, or greater solvent systems are collectively understood as multi-solvent systems. In various embodiments, the desired polymorph is Form III, and the isolating step involves crystallization from a mono- or multi-solvent system, where the crystallization involves dissolving the compound of Formula I in the mono- or multi-solvent system at a temperature above ambient temperature. In some examples, the dissolving of the compound of Formula I in the mono- or multi-solvent system is performed at a temperature of about 40-90° C., 50-90° C., 60-90° C., 70-90° C., 80-90° C., 40-80° C., 50-80° C., 60-80° C., 70-80° C., 40-70° C., 50-70° C., 60-70° C., 40-60° C., 50-60° C., or 40-50° C. In some examples, the dissolving of the compound of Formula I in the mono- or multi-solvent system is performed at a temperature of about 75-85° C. In some examples, the recrystallization solvent comprises alcohol for example ethanol, and the dissolving of the compound of Formula I in the solvent is performed at a temperature of about 75-85° C. In various embodiments, the recrystallization method further involves addition of a second solvent. In some embodiments, the second solvent is an alkane. In some examples, the second solvent is heptane, for example heptane or n-heptane. In some embodiments, the n-heptane is added dropwise to the solution of Formula I in n-heptane at a temperature of 75-85° C.

In various embodiments, the crystallization further involves actively heating the solution containing the dissolved compound of Formula I, for example to a temperature of about 40-100° C., 40-90° C., 40-80° C., 40-70° C., 40-60° C., 40-50° C., 50-100° C., 50-90° C., 50-80° C., 50-70° C., 50-60° C., 60-100° C., 60-90° C., 60-80° C., 60-70° C., 70-100° C., 70-90° C., 70-80° C., 80-100° C., or 80-90° C. In some embodiments, the solution containing the dissolved compound of Formula I, is heated to a temperature of about 75-85° C. In various embodiments, the solution containing the dissolved compound of Formula I is further maintained at the heated temperature (above ambient) for some period time, for example for about 30 min, about 1 h, about 2 h, about 3 h, about 4 h, about 5 h, about 6 h, about 7 h, about 8 h, about 9 h, about 10 h, about 11 h, about 12 h, about 13 h, about 14 h, about 15 h, about 16 h, about 17 h, about 18 h, about 19 h, about 20 h, about 21 h, about 22 h, about 23 h, about 24 h or more. In some embodiments, the solution containing the dissolved compound of Formula I is maintained at the heated temperature for about 1 hour.

In various embodiments, the crystallization further involves actively cooling the solution containing the dissolved compound of Formula I, for example to a temperature of about 40-70° C., 50-70° C., 60-70° C., 50-70° C., 50-60° C., or 60-70° C. In some embodiments, the crystallization involves actively cooling the solution containing the dissolved compound of Formula I in ethanol and n-heptane to a temperature of about 50-60° C. In various embodiments, the solution containing the dissolved compound of Formula I is further maintained at this lower temperature for some period time, for example for about 30 min, about 1 h, about 2 h, about 3 h, about 4 h, about 5 h, about 6 h, about 7 h, about 8 h, about 9 h, about 10 h, about 11 h, about 12 h, about 13 h, about 14 h, about 15 h, about 16 h, about 17 h, about 18 h, about 19 h, about 20 h, about 21 h, about 22 h, about 23 h, about 24 h or more. In some examples, the solution containing the dissolved compound of Formula I is maintained at this lower temperature for a time period of about 2 hours.

In various embodiments, the steps of active heating followed by active cooling are repeated more than one times, for example at least 2, at least 3, at least 4, at least 5, at least 6, at least 7, at least 8, at least 9, at least 10 times. In some embodiments, the steps of active heating followed by active cooling are repeated 2, 3, 4, 5, 6, 7, 8, 9, or 10 times. In some embodiments, the heating followed by cooling steps are repeated 2 times.

In various embodiments, the solution of compound of Formula I obtained after the active heating and or active cooling is further cooled to a temperature of about 0-40° C., 0-30° C., 0-20° C., 0-10° C., 10-40° C., 10-30° C., 10-20° C., 20-40° C., 20-30° C., 20-10° C., or 30° C.-40° C. In some embodiments, the solution containing the dissolved compound of Formula I is cooled to a temperature of about 20-30° C. In various embodiments, the solution containing the dissolved compound of Formula I is further maintained at this lower temperature for some period time, for example for about 30 min, about 1 h, about 2 h, about 3 h, about 4 h, about 5 h, about 6 h, about 7 h, about 8 h, about 9 h, about 10 h, about 11 h, about 12 h, about 13 h, about 14 h, about 15 h, about 16 h, about 17 h, about 18 h, about 19 h, about 20 h, about 21 h, about 22 h, about 23 h, about 24 h or more. In some embodiments, the solution containing the dissolved compound of Formula I is cooled to a temperature of about 20-30° C. and maintained at this temperature for about 3 hours.

In various embodiments, the crystallization further involves filtering the solution containing the obtained crystals of the compound of Formula I. In some embodiments, the crystallization optionally involves washing the obtained crystals by a solvent, for example by the recrystallization solvent one or more times. In some embodiments, the crystallization optionally involves drying the obtained crystals, for example under vacuum at a temperature of about 30-40° C.

In some embodiments, the Form III is non-micronized. In some embodiments a majority of particles in the non-micronized polymorph Form III, for example greater than 60%, 70%, 80%, 90%, or 95% of particles in the polymorph Form III are smaller than about 5 μm in diameter, about 10 μm in diameter, about 15 μm in diameter, about 20 μm in diameter, about 25 μm in diameter, about 30 μm in diameter, about 35 μm in diameter, about 40 μm in diameter, about 45 μm in diameter, about 50 μm in diameter, about 55 μm in diameter, about 60 μm in diameter, about 65 μm in diameter, about 70 μm in diameter, about 75 μm in diameter, about 80 μm in diameter, about 85 μm in diameter, about 95 μm in diameter, about 100 μm in diameter, about 110 μm in diameter, about 120 μm in diameter, about 130 μm in diameter, about 140 μm in diameter, about 150 μm in diameter, about 160 μm in diameter, about 170 μm in diameter, about 180 μm in diameter, about 190 μm in diameter, about 200 μm in diameter, about 210 μm in diameter, about 220 μm in diameter, about 230 μm in diameter, about 240 μm in diameter, about 250 μm in diameter, about 260 μm in diameter, about 270 μm in diameter, about 280 μm in diameter, about 290 μm in diameter, or about 300 μm in diameter. In some examples 60%, 70%, 80%, 90%, or 95% of the particles in non-micronized Form III have a diameter less than about 100 μm.

In some embodiments, the Form III is micronized. In some embodiments a majority of particles in the micronized polymorph Form III, for example greater than 60%, 70%, 80%, 90%, or 95% of particles in the polymorph Form III are smaller than about 5 μm in diameter, about 10 μm in diameter, about 15 μm in diameter, about 20 μm in diameter, about 25 μm in diameter, about 30 μm in diameter, about 35 μm in diameter, about 40 μm in diameter, about 45 μm in diameter, about 50 μm in diameter, about 55 μm in diameter, about 60 μm in diameter, about 65 μm in diameter, about 70 μm in diameter, about 75 μm in diameter, about 80 μm in diameter, about 85 μm in diameter, about 95 μm in diameter, about 100 μm in diameter, about 110 μm in diameter, about 120 μm in diameter, about 130 μm in diameter, about 140 μm in diameter, about 150 μm in diameter, about 160 μm in diameter, about 170 μm in diameter, about 180 μm in diameter, about 190 μm in diameter, about 200 μm in diameter, about 210 μm in diameter, about 220 μm in diameter, about 230 μm in diameter, about 240 μm in diameter, about 250 μm in diameter, about 260 μm in diameter, about 270 μm in diameter, about 280 μm in diameter, about 290 μm in diameter, or about 300 μm in diameter. In some examples 60%, 70%, 80%, 90%, or 95% of the particles in micronized Form III have a diameter less than about 5 μm. In some examples 60%, 70%, 80%, 90%, or 95% of the particles in micronized Form III have a diameter less than about 10 μm. In some examples 60%, 70%, 80%, 90%, or 95% of the particles in micronized Form III have a diameter less than about 20 μm.

In some embodiments, the chemical purity of the polymorph Form III is greater than 60%, 70%, 80%, 90%, 95%, or 99%. In some embodiments, the chemical purity of the polymorph Form III is greater than about 90%. In some embodiments, the chemical purity of the polymorph Form III is greater than about 95%. In some embodiments, the chemical purity of the polymorph Form III greater than about 99%. The chemical purity of polymorph Form III may be measured by any available analytical technique, for example by HPLC analysis.

In various embodiments, the polymorph Form III is dry. In various embodiments, the polymorph Form III is non-solvated. In some embodiments, the polymorph Form III is solvated.

In various embodiments, the polymorph Form III is characterized by an endotherm at about 180-200° C., for example at about 180-198° C., 180-196° C., 180-194° C., 180-192° C., 180-190° C., 180-188° C., 180-186° C., 180-184° C., 180-182° C., 182-198° C., 182-196° C., 182-194° C., 182-192° C., 182-190° C., 182-188° C., 182-186° C., 182-184° C., 184-198° C., 184-196° C., 184-194° C., 184-192° C., 184-190° C., 184-188° C., 184-186° C., 186-198° C., 186-196° C., 186-194° C., 186-192° C., 186-190° C., 186-188° C., 188-198° C., 188-196° C., 188-194° C., 188-192° C., 188-190° C., 188-198° C., 190-198° C., 190-196° C., 190-194° C., 190-192° C., 192-198° C., 192-196° C., 192-194° C., 194-198° C., 194-196° C., or 196-198° C. in the DSC trace. In various embodiments, the polymorph Form III is characterized by an endotherm at about 187-191° C. in the DSC trace. In some embodiments, the DSC thermogram of the polymorph Form III further comprises an endotherm, corresponding to the solvent, at around 116-136° C., for example at about 116-118° C., 116-120° C., 116-122° C., 116-124° C., 116-126° C., 116-128° C., 116-130° C., 116-132° C., 116° C.-134° C., 116° C.-136° C., 118° C.-120° C., 118° C.-122° C., 118° C.-124° C., 118° C.-126°

C., 118° C.-128° C., 118° C.-130° C., 118° C.-132° C., 118° C.-134° C., 118° C.-136° C., 120° C.-122° C., 120° C.-124° C., 120° C.-126° C., 120° C.-128° C., 120° C.-130° C., 120° C.-132° C., 120° C.-134° C., 120° C.-136° C., 122° C.-124° C., 122° C.-126° C., 122° C.-128° C., 122° C.-130° C., 122° C.-132° C., 122° C.-134° C., 122° C.-136° C., 124° C.-126° C., 124° C.-128° C., 124° C.-130° C., 124° C.-132° C., 124° C.-134° C., 124° C.-136° C., 126° C.-128° C., 126° C.-130° C., 126° C.-132° C., 126° C.-134° C., 126° C.-136° C., 128° C.-130° C., 128° C.-132° C., 128° C.-134° C., 128° C.-136° C., 130° C.-132° C., 130° C.-134° C., 130° C.-136° C., 132° C.-134° C., 132° C.-136° C., or 134° C.-136° C. In some embodiments, the DSC thermogram of the polymorph Form III further comprises an endotherm, corresponding to the solvent, at about 120° C. In some embodiments, the solvent is ethanol.

In some embodiments the melting point of the polymorph Form III is about 185-191° C., for example about 185° C., 186° C., 187° C., 188° C., 189° C., 190° C., or 191° C. In some embodiments, the melting point of the polymorph Form III is about 188° C.

Polymorph Form IV of the Compound of Formula I

Figure 9:
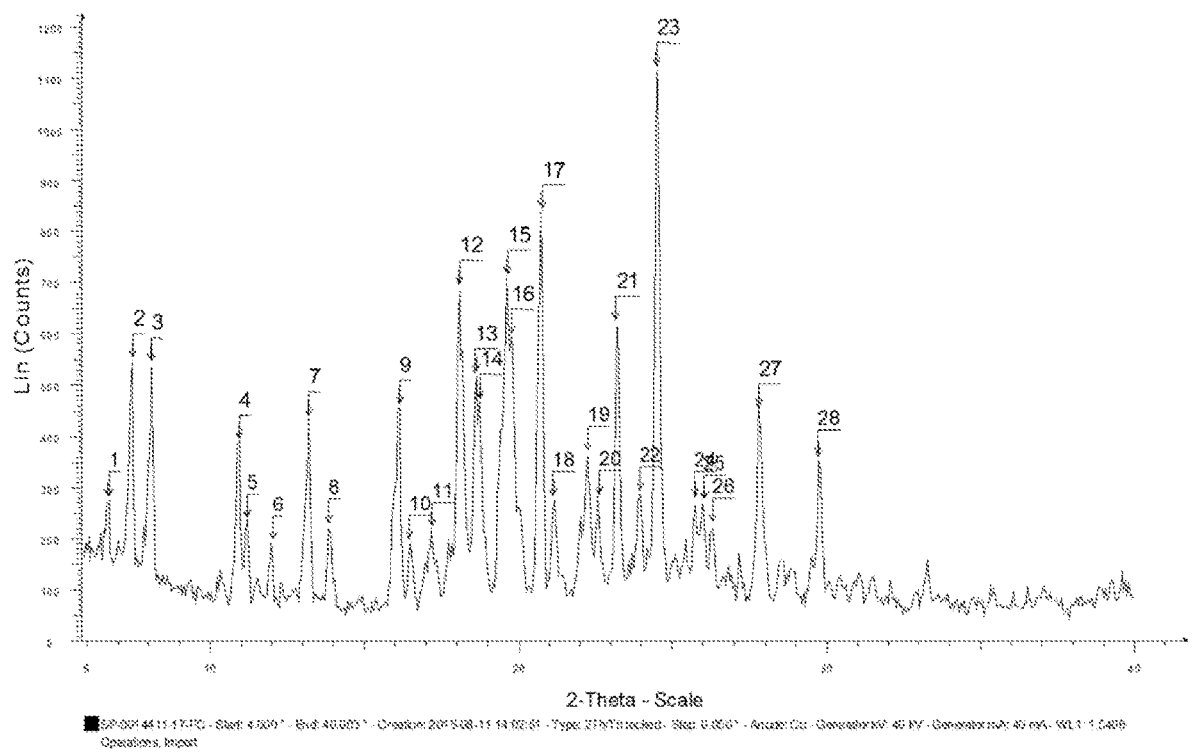
FIG. 9 shows the XRPD for polymorph Form IV of the compound of Formula I.

FIG. 9 shows the XRPD for the polymorph Form IV of the compound of Formula I.

Figure 10:
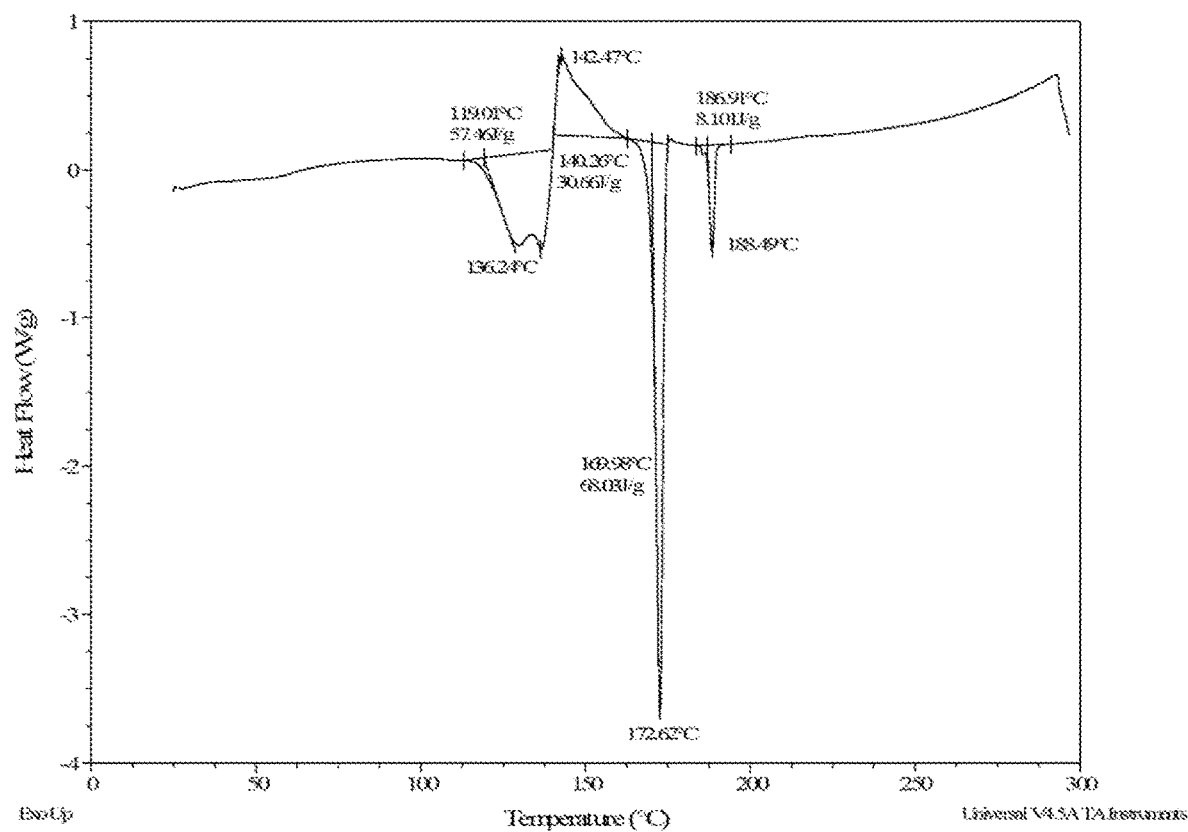
FIG. 10 shows an exemplary DSC thermogram of the polymorph Form IV of the compound of Formula I.

FIG. 10 shows an exemplary DSC thermogram of Form IV of the compound of Formula I.

In one embodiment, the desired polymorph is Form IV of the compound of Formula I, and the isolating step involves recrystallization of crude reaction product from a mono-solvent system. In various embodiments, the desired polymorph is Form IV of the compound of Formula I, and the isolating step involves recrystallization of crude product from a binary, tertiary, or greater solvent system, collectively understood as a multi-solvent system. In various embodiments, the desired polymorph is Form IV of the compound of Formula I, and the isolating step involves crystallization from a mono- or multi-solvent system, where the crystallization involves dissolving the compound of Formula I in the mono- or multi-solvent system at a temperature above ambient temperature. In some examples, the dissolving of the compound of Formula I in the mono- or multi-solvent system is performed at a temperature of about 40-90° C., 45-90° C., 50-90° C., 55-90° C., 60-90° C., 65-90° C., 70-90° C., 75-90° C., 40-85° C., 45-85° C., 50-85° C., 55-85° C., 60-85° C., 65-85° C., 70-85° C., 75-85° C., 80-85° C., 40-80° C., 45-80° C., 50-80° C., 55-80° C., 60-80° C., 65-80° C., 70-80° C., 75-80° C., 40-75° C., 45-75° C., 50-75° C., 55-75° C., 60-75° C., 65-75° C., 70-75° C., 40-70° C., 45-70° C., 50-70° C., 55-70° C., 60-70° C., 65-70° C., 40-65° C., 45-65° C., 50-65° C., 55-65° C., 60-65° C., 40-60° C., 45-60° C., 50-60° C., 55-60° C., 40-55° C., 45-55° C., 50-55° C., 40-50° C., or 45-50° C. In some examples, the recrystallization solvent is ethyl acetate and the dissolving of the compound of Formula I in the solvent system is performed at a temperature of about 75-85° C. Any suitable amount of solvent can be used for dissolving the compound of Formula I. In some embodiments, the amount of solvent used to dissolve the compound is from about 100-10 mL per gram of the compound of Formula I, for example from about 50-30 mL per gram of the compound of Formula I. In some embodiments, the amount of solvent used for dissolving the compound of Formula I is about 40 mL per gram of the compound of Formula I. In some examples, the recrystallization solvent is ethyl acetate and the dissolving of the compound of Formula I in the solvent system is performed at a temperature of about 75-85° C. and the amount of solvent used for dissolving is about 40 mL/g of the compound of Formula I.

In some embodiments, the resulting solution of the compound of Formula I is treated with a drying agent (e.g. anhydrous $Na_2SO_4$), adsorption agent (e.g. activated carbon) and/or a silica metal scavenger. In some embodiments, the solution of the compound of Formula I is treated with anhydrous $Na_2SO_4$, activated carbon and/or a silica metal scavenger and stirred for about 15 mins-5 hour, for example for about 15 mins, 30 mins, 1 hour, 2 hours, 3 hours, 4 hours, or about 5 hours. In various embodiments, the resulting mixture is filtered and washed with a solvent, for example with ethyl acetate. In some embodiments, the filtration and washing is performed at an elevated temperature for example at about 40-90° C., example at about 75-85° C. In various embodiments, the filtrate is concentrated. In some embodiments the concentration is performed under vacuum at a temperature of about 10-60° C., for example at a temperature of about 10-50° C., 10-40° C., 10-30° C., 10-20° C., 20-60° C., 20-50° C., 20-40° C., 20-30° C., 30-60° C., 30-50° C., 30-40° C., 30-60° C., 30-50° C., 30-40° C., 20-30° C. and 10-20° C. In some embodiments, concentration is performed under vacuum at a temperature of about 30-40° C.

In various embodiments, the concentrated mixture of the compound of Formula I is further dissolved in a different solvent. In some embodiments, this solvent is an organic solvent, for example an halo alkane (for e.g. chloromethane, dichloromethane (DCM), chloroform, or tetrachloromethane). In some embodiments, this solvent is DCM. The amount of solvent used for dissolving the compound of Formula I is about 100 mL-1 mL per gram of the compound of Formula I, for example about 100-10 g/mL, 100-20 g/mL, 100-30 g/mL, 100-40 g/mL, 100-50 g/mL, 100-60 g/mL, 100-70 g/mL, 100-80 g/mL, 100-90 g/mL, 90-1 g/mL, 90-10 g/mL, 90-20 g/mL, 90-30 g/mL, 90-40 g/mL, 90-50 g/mL, 90-60 g/mL, 90-70 g/mL, 90-80 g/mL, 80-1 g/mL, 80-10 g/mL, 80-20 g/mL, 80-30 g/mL, 80-40 g/mL, 80-50 g/mL, 80-60 g/mL, 80-70 g/mL, 70-1 g/mL, 70-10 g/mL, 70-20 g/mL, 70-30 g/mL, 70-40 g/mL, 70-50 g/mL, 70-60 g/mL, 60-1 g/mL, 60-10 g/mL, 60-20 g/mL, 60-30 g/mL, 60-40 g/mL, 60-50 g/mL, 50-1 g/mL, 50-10 g/mL, 50-20 g/mL, 50-30 g/mL, 50-40 g/mL, 40-1 g/mL, 40-10 g/mL, 40-20 g/mL, 40-30 g/mL, 30-1 g/mL, 30-10 g/mL, 30-20 g/mL, 20-1 g/mL, or 20-10 g/mL. In some embodiments, the amount of solvent used to dissolve the concentrated Formula I is about 10 mL/g.

In various embodiments, the recrystallization method further involves addition of a second solvent. In some embodiments, the second solvent is an organic alkane. In some examples, the second solvent is heptane, for example n-heptane. In some embodiments, the n-heptane is added dropwise to the solution of Formula I in DCM at a temperature of 25-55° C., for example at a temperature of about 30-55° C., 35-55° C., 40-55° C., 45-55° C., 50-55° C., 25-50° C., 30-50° C., 35-50° C., 40-50° C., 45-50° C., 25-45° C., 30-45° C., 35-45° C., 40-45° C., 25-40° C., 30-40° C., 35-40° C., 25-35° C., 30-35° C., or 25-30° C. In various embodiments, the ratio of the amount of the first solvent (e.g. DCM) to the amount of the second solvent (e.g. n-heptane) is from about 5:1 to about 1:5, for example about 5:1, 4.5:1, 4:1, 3.5:1, 3:1, 2.5:1, 2:1, 1.5:1, 1:1, 1:1.5, 1:2, 1:2.5, 1:3, 1:3.5, 1:4, 1:4.5, or about 1:5. In some embodiments, the n-heptane is added to the solution of Formula I in DCM at a temperature of about 35-45° C. and the ratio of the amount of DCM to the amount of n-heptane is about 2:1.

In various embodiments, the solution of compound of Formula I in DCM/n-heptane is further cooled to a temperature of about 0-40° C., 0-30° C., 0-20° C., 0-10° C., 10-40° C., 10-30° C., 10-20° C., 20-40° C., 20-30° C., 20-10° C., or 30° C.-40° C. In some embodiments, the solution containing the dissolved compound of Formula I is cooled to a temperature of about 20-30° C. In various embodiments, the solution containing the dissolved compound of Formula I is further maintained at this lower temperature for some period time, for example for about 30 min, about 1 h, about 2 h, about 3 h, about 4 h, about 5 h, about 6 h, about 7 h, about 8 h, about 9 h, about 10 h, about 11 h, about 12 h, about 13 h, about 14 h, about 15 h, about 16 h, about 17 h, about 18 h, about 19 h, about 20 h, about 21 h, about 22 h, about 23 h, or about 24 h or more.

In various embodiments, the crystallization further involves filtering the solution containing the obtained crystals of the compound of Formula I. In some embodiments, the crystallization optionally involves washing the obtained crystals by a solvent, for example by the recrystallization solvent (e.g. DCM/n-heptane) one or more times. In some embodiments, the crystallization optionally involves drying the obtained crystals for example under vacuum at a temperature of about 30-40° C.

In some embodiments, the chemical purity of the polymorph Form VI is greater than 60%, 70%, 80%, 90%, 95%, 99%, 99.6% or 99.9%. In some embodiments, the chemical purity of the polymorph Form VI is greater than about 90%. In some embodiments, the chemical purity of the polymorph Form VI is greater than about 95%. In some embodiments, the chemical purity of the polymorph Form VI is greater than about 99%. The chemical purity of polymorph Form VI may be measured by any available analytical technique, for example by HPLC analysis.

In various embodiments, the polymorph Form IV is characterized by an endotherm at about 116-146° C., for example at about 116-144° C., 116-142° C., 116-140° C., 116-138° C., 116-136° C., 115-135° C., 116-134° C., 116-132° C., 116-130° C., 116-128° C., 126-144° C., 126-142° C., 126-140° C., 126-138° C., 126-136° C., 126-134° C., 126-132° C., 126-130° C., 126-128° C., 128-146° C., 128-144° C., 128-142° C., 128-140° C., 128-138° C., 128-136° C., 128-134° C., 128-132° C., 128-130° C., 130-146° C., 130-144° C., 130-142° C., 130-140° C., 130-138° C., 130-136° C., 130-134° C., 130-132° C., 132-146° C., 132-144° C., 132-142° C., 132-140° C., 132-138° C., 132-136° C., 132-134° C. 134-146° C., 134-144° C., 134-142° C., 134-140° C., 134-138° C., 134-136° C., 136-146° C., 136-144° C., 136-142° C., 136-140° C., 136-138° C., 138-146° C., 138-144° C., 138-142° C., 138-140° C., 140-146° C., 140-144° C., 140-142° C., 142-146° C., or 142-144° C. in the DSC trace. In various embodiments, the DSC thermogram of polymorph Form IV further comprises an endotherm at about 163-183° C. in the DSC trace, for example at about 163-181° C., 163-179° C., 163-177° C., 163-175° C., 163-173° C., 163-171° C., 163-169° C., 163-167° C., 163-165° C., 165-183° C., 165-181° C., 165-179° C., 165-177° C., 165-175° C., 165-173° C., 165-171° C., 165-169° C., 165-167° C., 167-183° C., 167-181° C., 167-179° C., 167-177° C., 167-175° C., 167-173° C., 167-171° C., 167-169° C., 168-178° C., 169-183° C., 169-181° C., 169-179° C., 169-177° C., 169-175° C., 169-173° C., 169-171° C., 171-183° C., 171-181° C., 171-179° C., 171-177° C., 171-175° C., 171-173° C., 173-183° C., 173-181° C., 173-179° C., 173-177° C., 173-175° C., 175-183° C., 175-181° C., 175-179° C., 175-177° C., 177-183° C., 177-181° C., 177-179° C., 179-183° C., 179-181° C., or 181-183° C. In some embodiments, the DSC thermogram of the polymorph Form IV further comprises an endotherm at around 179-199° C., for example at about 179-197° C., 179-195° C., 179-193° C., 179-191° C., 179-189° C., 179-187° C., 179-185° C., 179-183° C., 179° C.-181° C., 181-199° C., 181-197° C., 181° C., 181-193° C., 181-191° C., 181-189° C., 181-187° C., 181-185° C., 181-183° C., 183-193° C., 183-191° C., 183-189° C., 183-187° C., 183-185° C., 184-194° C., 185-193° C., 185-191° C., 185-189° C., 185-187° C., 187-193° C., 187-191° C., 187-189° C., 189-193° C., 189-191° C., or 191-193° C. In some embodiments, the DSC thermogram of the polymorph Form IV further comprises endotherms at bout 118-120° C., and 169-171° C., and 186-188° C.

In some embodiments, the DSC thermogram of the polymorph Form IV further comprises an exotherm at about 132-152° C., for example at about 132-150° C., 132-148° C., 132-146° C., 132-144° C., 132-142° C., 132-140° C., 132-138° C., 132-136° C., 132-134° C., 134-152° C., 134-150° C., 134-148° C., 134-146° C., 134-144° C., 134-142° C., 134-140° C., 134-138° C., 134-136° C., 136-150° C., 136-148° C., 136-146° C., 136-144° C., 136-142° C., 136-140° C., 136-138° C., 138-150° C., 138-148° C., 138-146° C., 138-144° C., 138-142° C., 138-140° C., 140-150° C., 140-148° C., 140-146° C., 140-144° C., 140-142° C., 142-150° C., 142-148° C., 142-146° C., 142-144° C., 144-150° C., 144-148° C., 144-146° C., 146-150° C., 146-148° C., or 148-150° C.

Polymorph Form V of the Compound of Formula I

Figure 11:
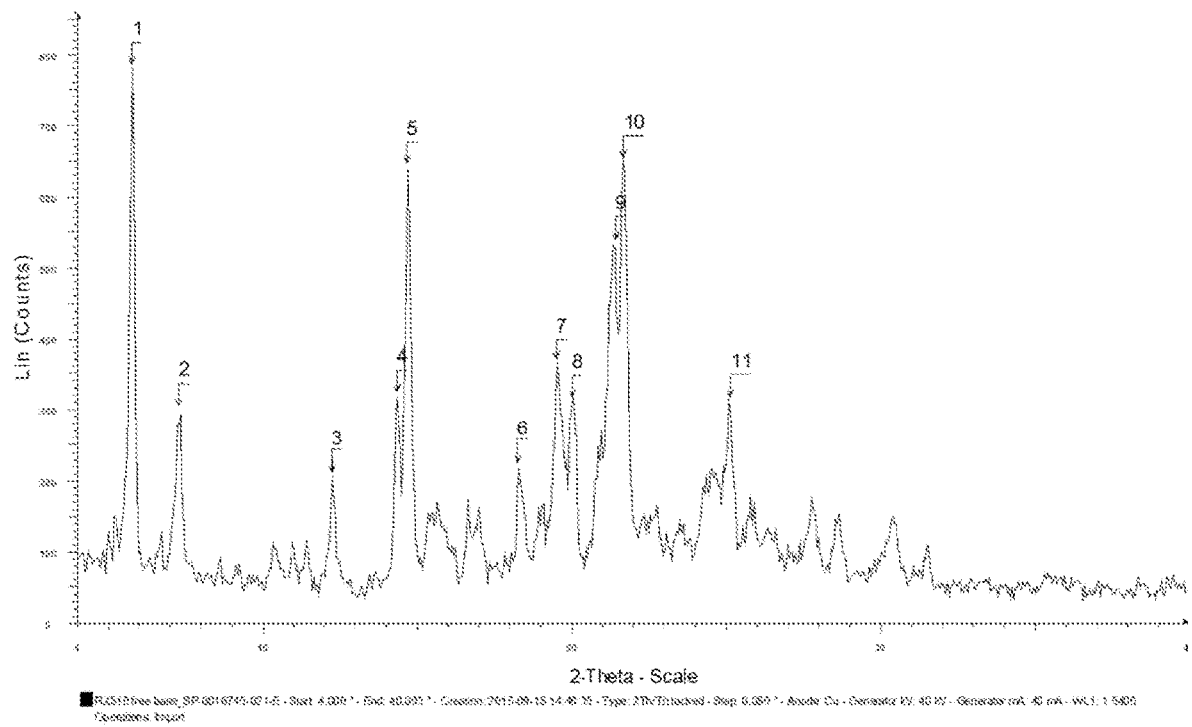
FIG. 11 shows the XRPD for polymorph Form V of the compound of Formula I.

FIG. 11 shows the XRPD for the polymorph Form V of the compound of Formula I.

Figure 12:
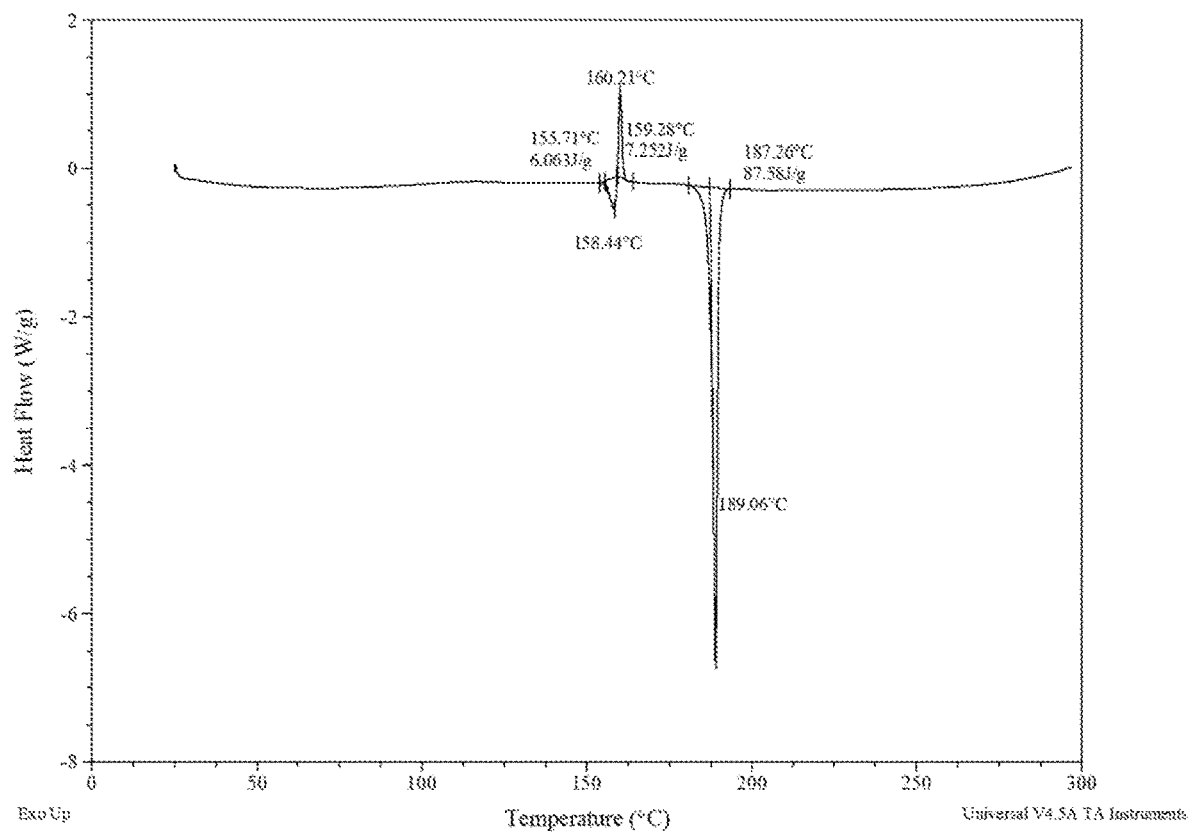
FIG. 12 shows an exemplary DSC thermogram of the polymorph Form V of the compound of Formula I.

FIG. 12 shows an exemplary DSC thermogram of Form V of the compound of Formula I.

In one embodiment, the desired polymorph is Form V of the compound of Formula I, and the isolating step involves drying the polymorph Form III of the compound of Formula I. In some embodiments, the drying is performed at a temperature above the ambient temperature, for example in an oven. In some embodiments, the drying is performed at a temperature of about 100° C., about 95° C., about 90° C., about 85° C., about 80° C., about 75° C., about 70° C., about 65° C., about 60° C., about 55° C., about 50° C., about 45° C. or about 40° C. In various embodiments, the drying is performed for a time period of about 1 hour to about 5 days, for example for about 1 h, 2 h, 4 h, 6 h, 8 h, 10 h, 12 h, 14 h, 16 h, 18 h, 20 h, 22 h, 24 h, 1.5 days, 2 days, 2.5 days, 3 days, 3.5 days, 4 days, 4.5 days or about 5 days.

In some embodiments, Form III of the compound of Formula I is dried in an oven at a temperature of about 80° C. for a time period of 40-72 hours, for example for about 2 days and the resulting product is polymorph Form V of the compound of Formula I.

In some embodiments, the chemical purity of the polymorph Form V is greater than 60%, 70%, 80%, 90%, 95%, 99%, 99.6% or 99.9%. In some embodiments, the chemical purity of the polymorph Form V is greater than about 90%. In some embodiments, the chemical purity of the polymorph Form V is greater than about 95%. In some embodiments, the chemical purity of the polymorph Form V is greater than about 99%. The chemical purity of polymorph Form V may be measured by any available analytical technique, for example by HPLC analysis.

In various embodiments, the polymorph Form V of the compound of Formula I is dry. In various embodiments, the polymorph Form V of the compound of Formula I is non-solvated. In various embodiments, the polymorph Form V of the compound of Formula I is non-hydrated. In various embodiments, the polymorph Form V of the compound of Formula I is non-hygroscopic.

In various embodiments, the polymorph Form V of the compound of Formula I is characterized by an endotherm at about 149-169° C., for example at about 149-167° C., 149-165° C., 149-163° C., 149-161° C., 149-159° C., 149-157° C., 149-155° C., 149-153° C., 149-151° C., 151-169° C., 151-167° C., 151-165° C., 151-163° C., 151-161° C., 151-159° C., 151-157° C., 151-155° C., 151-153° C., 152-162° C., 153-169° C., 153-167° C., 153-165° C., 153-163° C., 153-161° C., 153-159° C., 153-157° C., 153-155° C., 155-169° C., 155-167° C., 155-165° C., 155-163° C., 155-161° C., 155-159° C., 155-157° C., 157-169° C., 157-167° C., 157-165° C., 157-163° C., 157-161° C., 157-159° C., 159-169° C., 159-167° C., 159-165° C., 159-163° C., 159-161° C., 161-169° C., 161-167° C., 161-165° C., 161-163° C., 163-169° C., 163-167° C., 163-165° C., 165-169° C., 165-167° C. or 167-169° C. in the DSC trace. In various embodiments, the DSC thermogram of polymorph Form V further comprises an endotherm at about 180-200° C. in the DSC trace, for example at about 180-198° C., 180-196° C., 180-194° C., 180-192° C., 180-190° C., 180-188° C., 180-186° C., 180-184° C., 180-182° C., 182-200° C., 182-198° C., 182-196° C., 182-194° C., 182-192° C., 182-190° C., 182-188° C., 182-186° C., 182-184° C., 183-193° C., 184-200° C., 184-198° C., 184-196° C., 184-194° C., 184-192° C., 184-190° C., 184-188° C., 184-186° C., 186-200° C., 186-198° C., 186-196° C., 186-194° C., 186-192° C., 186-190° C., 186-188° C., 188-200° C., 188-198° C., 188-196° C., 188-194° C., 188-192° C., 188-190° C., 190-200° C., 190-198° C., 190-196° C., 190-194° C., 190-192° C., 192-200° C., 192-198° C., 192-196° C., 192-194° C., 194-200° C., 194-198° C., 194-196° C., 196-200° C., 196-198° C., or 198-200° C.

In some embodiments, the DSC thermogram of the polymorph Form V further comprises an exotherm at about 151-171° C., for example at about 151-169° C., 151-167° C., 151-165° C., 151-163° C., 151-161° C., 151-159° C., 151-157° C., 151-155° C., 151-153° C., 153-171° C., 153-169° C., 153-167° C., 153-165° C., 153-163° C., 153-161° C., 153-159° C., 153-157° C., 153-155° C., 155-171° C., 155-169° C., 155-167° C., 155-165° C., 155-163° C., 155-161° C., 155-159° C., 155-157° C., 157-171° C., 157-169° C., 157-167° C., 157-165° C., 157-163° C., 157-161° C., 157-159° C., 159-171° C., 159-169° C., 159-167° C., 159-165° C., 159-163° C., 159-161° C., 161-171° C., 161-169° C., 161-167° C., 161-165° C., 161-163° C., 163-171° C., 163-169° C., 163-167° C., 163-165° C., 165-171° C., 165-169° C., 165-167° C., 167-171° C., 167-169° C., or 169-171° C.

Polymorph Form VI of the Compound of Formula I

Figure 13:
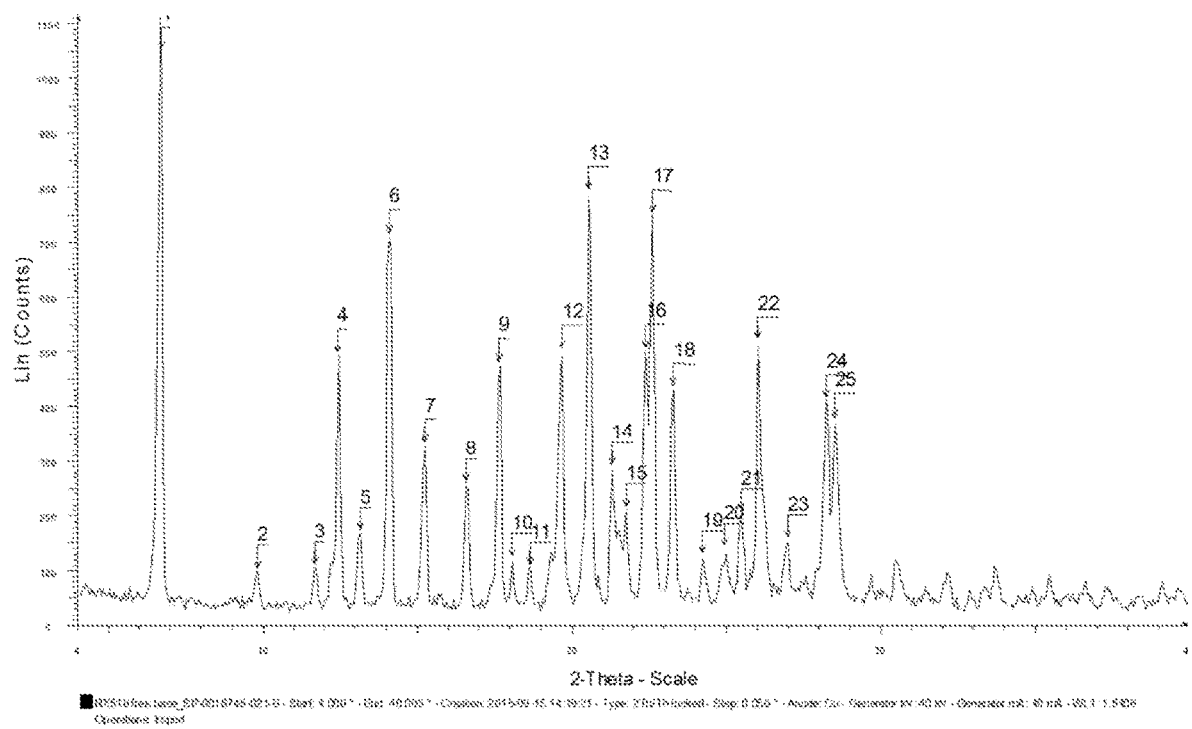
FIG. 13 shows the XRPD for polymorph Form VI of the compound of Formula I.

FIG. 13 shows the XRPD for the polymorph Form VI of the compound of Formula I.

Figure 14:
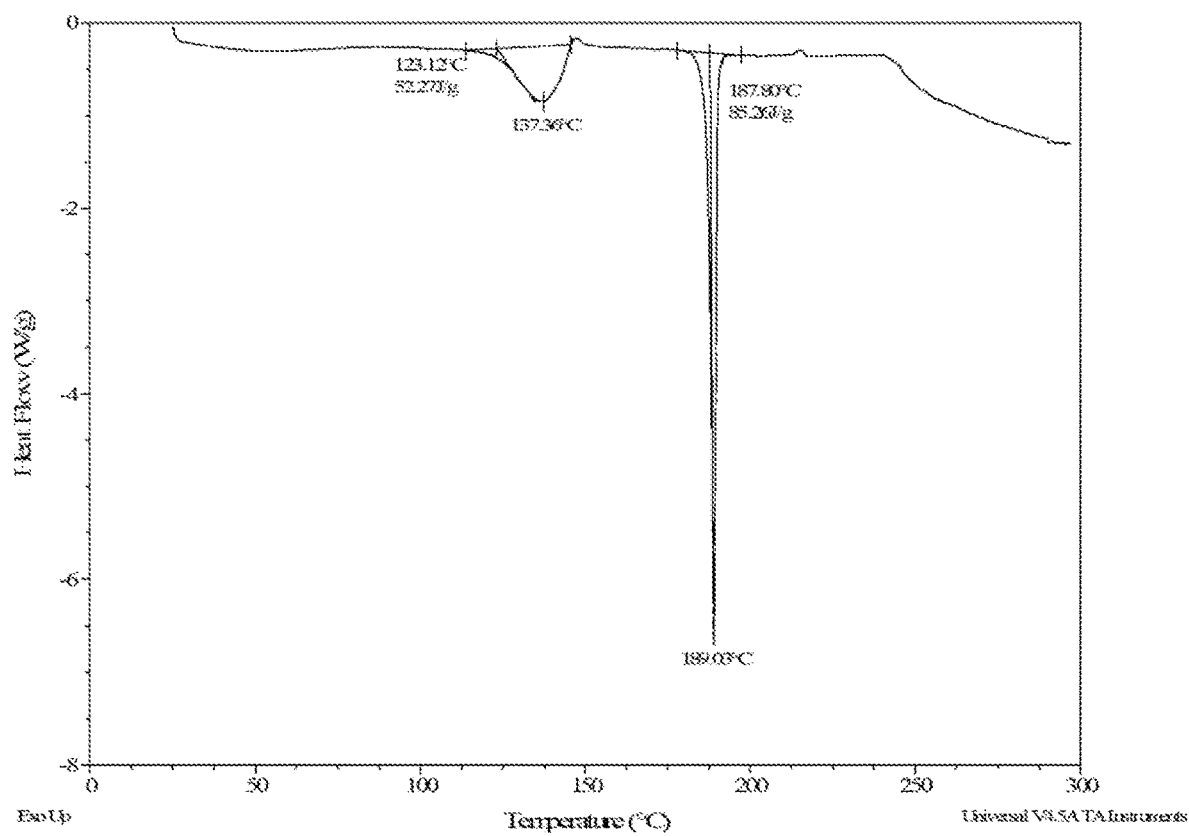
FIG. 14 shows an exemplary DSC thermogram of the polymorph Form VI of the compound of Formula I.
Figure 15:
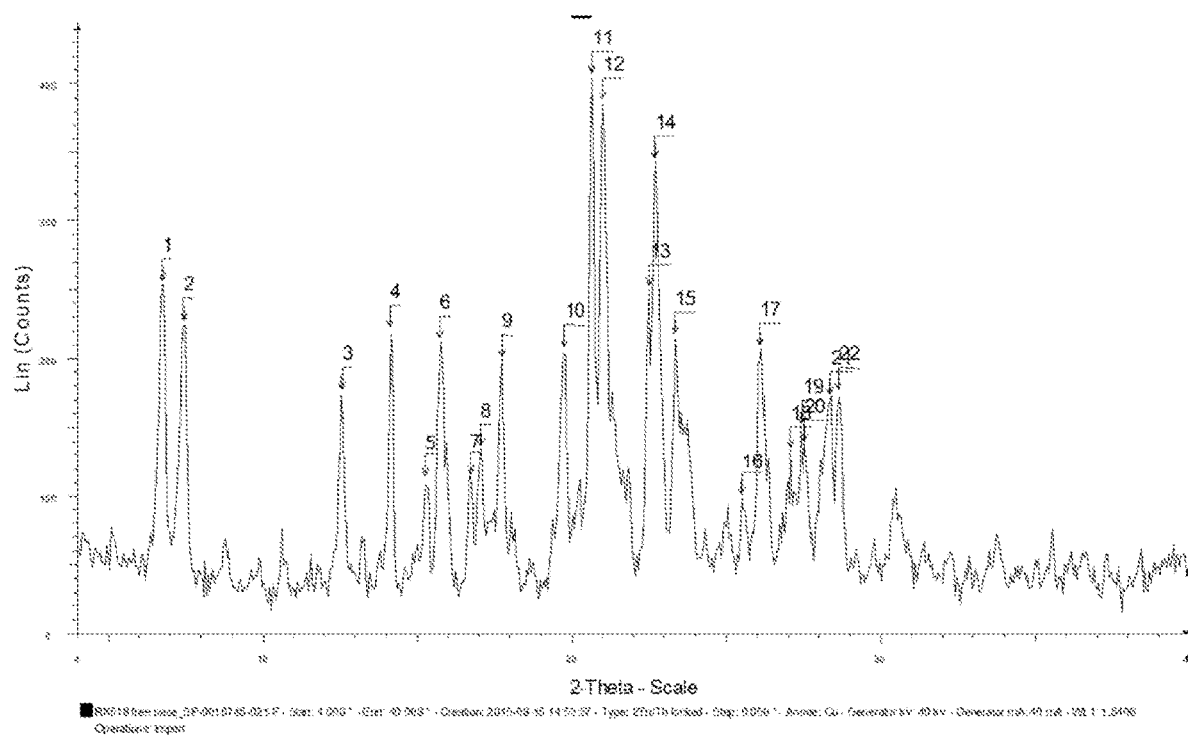
FIG. 15 shows the XRPD for polymorph Form VIII of the compound of Formula I.
Figure 16:
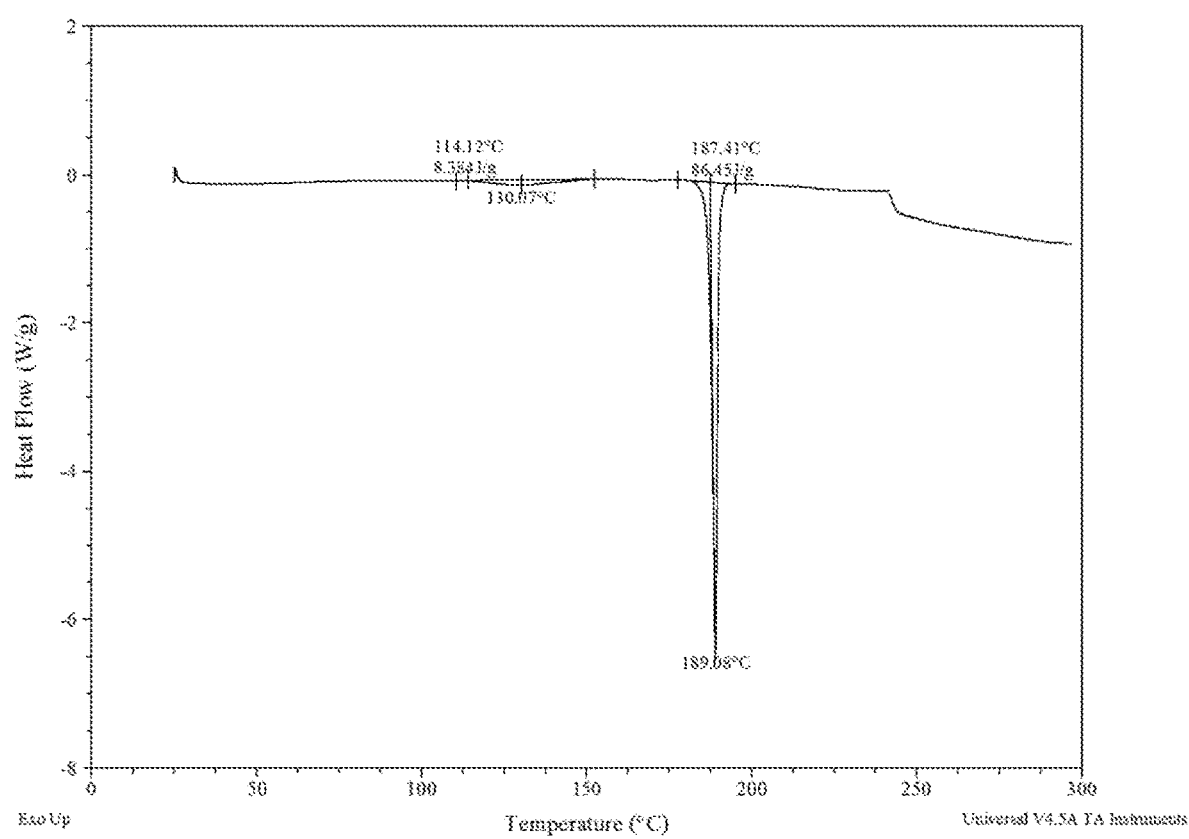
FIG. 16 shows an exemplary DSC thermogram of the polymorph Form VIII of the compound of Formula I.

FIG. 14 shows an exemplary DSC thermogram of the polymorph Form VI of the compound of Formula I.

In various embodiments, the desired polymorph is Form VI of the compound of Formula I, and the isolating step involves recrystallization of crude reaction product from a mono-solvent system. In various embodiments, the desired polymorph is Form VI of the compound of Formula I, and the isolating step involves recrystallization of crude product from a binary, tertiary, or greater solvent system, where binary, tertiary, or greater solvent systems are collectively understood as multi-solvent systems. In various embodiments, the desired polymorph is Form VI of the compound of Formula I, and the isolating step involves crystallization from a mono- or multi-solvent system, where the crystallization involves dissolving the compound of Formula I in the mono- or multi-solvent system at a temperature above ambient temperature. In some examples, the dissolving of the compound of Formula I in the mono- or multi-solvent system is performed at a temperature of about 40-90° C., 50-90° C., 60-90° C., 70-90° C., 80-90° C., 40-80° C., 50-80° C., 60-80° C., 70-80° C., 40-70° C., 50-70° C., 60-70° C., 40-60° C., 50-60° C., or 40-50° C. In some examples, the dissolving of the compound of Formula I in the mono- or multi-solvent system is performed at a temperature of about 75-85° C. In some examples, the recrystallization solvent is an organic alcohol, for example isopropanol and the dissolving of the compound of Formula I is performed at a temperature of about 75-85° C. In various embodiments, the recrystallization method further involves addition of a second solvent to the solution of Formula I. In some embodiments, the second solvent is an organic alkane, for example heptane and n-heptane. In some embodiments, the second solvent is n-heptane and it is added dropwise to the solution of Formula I in isopropanol at a temperature of 75-85° C.

In various embodiments, the crystallization process further comprises cooling the resulting mixture to a temperature of about 35-75° C., for example to a temperature of about 35-70° C., 40-70° C., 45-70° C., 50-70° C., 55-70° C., 60-70° C., 65-70° C., 35-65° C., 40-65° C., 45-65° C., 50-65° C., 55-65° C., 60-65° C., 35-60° C., 40-60° C., 45-60° C., 50-60° C., 55-60° C. 35-55° C., 40-55° C., 45-55° C., 50-55° C., 35-50° C., 40-50° C., 45-50° C., 35-45° C., 40-45° C., or 35-40° C. In various embodiments, the mixture is maintained at this temperature for about 1 hour, 2 hour, 4 hour, 6 hour, 8 hour, 10 hour, 12 hour, 14 hour, 16 hour, 18 hour, 20 hour, 22 hour, 24 hours, 26 hours, 28 hours, 30 hours, or 32 hours.

In various embodiments, the crystallization further involves actively heating the solution containing the dissolved compound of Formula I, for example to a temperature of about 40-100° C., 40-90° C., 40-80° C., 40-70° C., 40-60° C., 40-50° C., 50-100° C., 50-90° C., 50-80° C., 50-70° C., 50-60° C., 60-100° C., 60-90° C., 60-80° C., 60-70° C., 70-100° C., 70-90° C., 70-80° C., 80-100° C., or 80-90° C. In some embodiments, the solution containing the dissolved compound of Formula I, is heated to a temperature of about 75-85° C. In various embodiments, the solution containing the dissolved compound of Formula I is further maintained at the heated temperature (above ambient) for some period time, for example for about 30 min, about 1 h, about 2 h, about 3 h, about 4 h, about 5 h, about 6 h, about 7 h, about 8 h, about 9 h, about 10 h, about 11 h, about 12 h, about 13 h, about 14 h, about 15 h, about 16 h, about 17 h, about 18 h, about 19 h, about 20 h, about 21 h, about 22 h, about 23 h, about 24 h or more. In some embodiments, the solution containing the dissolved compound of Formula I is maintained at the heated temperature for about 30 minutes.

In various embodiments, the crystallization further involves actively cooling the solution containing the dissolved compound of Formula I, for example to a temperature of about 40-70° C., 50-70° C., 60-70° C., 50-70° C., 50-60° C., or 60-70° C. In some embodiments, the crystallization involves actively cooling the solution containing the dissolved compound of Formula I to a temperature of about 45-55° C. In various embodiments, the solution containing the dissolved compound of Formula I is further maintained at this lower temperature for some period time, for example for about 30 min, about 1 h, about 2 h, about 3 h, about 4 h, about 5 h, about 6 h, about 7 h, about 8 h, about 9 h, about 10 h, about 11 h, about 12 h, about 13 h, about 14 h, about 15 h, about 16 h, about 17 h, about 18 h, about 19 h, about 20 h, about 21 h, about 22 h, about 23 h, about 24 h or more. In some examples, the solution containing the dissolved compound of Formula I is maintained at this lower temperature for a time period of about 30 minutes.

In various embodiments, the solution of compound of Formula I obtained after the active heating and/or active cooling is further cooled to a temperature of about 0-40° C., 0-30° C., 0-20° C., 0-10° C., 10-40° C., 10-30° C., 10-20° C., 20-40° C., 20-30° C., 20-10° C., or 30° C.-40° C. In some embodiments, the solution containing the dissolved compound of Formula I is cooled to a temperature of about 20-30° C. In various embodiments, the solution containing the dissolved compound of Formula I is further maintained at this lower temperature for some period time, for example for about 30 min, about 1 h, about 2 h, about 3 h, about 4 h, about 5 h, about 6 h, about 7 h, about 8 h, about 9 h, about 10 h, about 11 h, about 12 h, about 13 h, about 14 h, about 15 h, about 16 h, about 17 h, about 18 h, about 19 h, about 20 h, about 21 h, about 22 h, about 23 h, about 24 h or more. In some embodiments, the solution containing the dissolved compound of Formula I is cooled to a temperature of about 20-30° C. and maintained at this temperature for about 3 hours.

In various embodiments, the crystallization further involves filtering the solution containing the obtained crystals of the compound of Formula I. In some embodiments, the crystallization optionally involves washing the obtained crystals with a solvent, for example by the recrystallization solvent (isopropanol/n-heptane) one or more times. In some embodiments, the crystallization optionally involves drying the obtained crystals, for example under vacuum at a temperature of about 50-100° C., for example about 75-80° C. In various embodiments, the drying is performed for a time period of about 30 mins-2 days, for example for about 30 min, about 1 h, about 2 h, about 3 h, about 4 h, about 5 h, about 6 h, about 7 h, about 8 h, about 9 h, about 10 h, about 11 h, about 12 h, about 13 h, about 14 h, about 15 h, about 16 h, about 17 h, about 18 h, about 19 h, about 20 h, about 21 h, about 22 h, about 23 h, or about 24 h.

In some embodiments, the polymorph Form VI of the compound of Formula I is non-micronized. In some embodiments a majority of particles in the non-micronized polymorph Form VI, for example greater than 60%, 70%, 80%, 90%, or 95% of particles in the polymorph Form VI are smaller than about 5 μm in diameter, about 10 μm in diameter, about 15 μm in diameter, about 20 μm in diameter, about 25 μm in diameter, about 30 μm in diameter, about 35 μm in diameter, about 40 μm in diameter, about 45 μm in diameter, about 50 μm in diameter, about 55 μm in diameter, about 60 μm in diameter, about 65 μm in diameter, about 70 μm in diameter, about 75 μm in diameter, about 80 μm in diameter, about 85 μm in diameter, about 95 μm in diameter, about 100 μm in diameter, about 110 μm in diameter, about 120 μm in diameter, about 130 μm in diameter, about 140 μm in diameter, about 150 μm in diameter, about 160 μm in diameter, about 170 μm in diameter, about 180 μm in diameter, about 190 μm in diameter, about 200 μm in diameter, about 210 μm in diameter, about 220 μm in diameter, about 230 μm in diameter, about 240 μm in diameter, about 250 μm in diameter, about 260 μm in diameter, about 270 μm in diameter, about 280 μm in diameter, about 290 μm in diameter, or about 300 μm in diameter. In some examples 60%, 70%, 80%, 90%, or 95% of the particles in non-micronized Form VI have a diameter less than about 100 μm.

In some embodiments, the Form VI is micronized. In some embodiments a majority of particles in the micronized polymorph Form VI, for example greater than 60%, 70%, 80%, 90%, or 95% of particles in the polymorph Form VI are smaller than about 5 μm in diameter, about 10 μm in diameter, about 15 μm in diameter, about 20 μm in diameter, about 25 μm in diameter, about 30 μm in diameter, about 35 μm in diameter, about 40 μm in diameter, about 45 μm in diameter, about 50 μm in diameter, about 55 μm in diameter, about 60 μm in diameter, about 65 μm in diameter, about 70 μm in diameter, about 75 μm in diameter, about 80 μm in diameter, about 85 μm in diameter, about 95 μm in diameter, about 100 μm in diameter, about 110 μm in diameter, about 120 μm in diameter, about 130 μm in diameter, about 140 μm in diameter, about 150 μm in diameter, about 160 μm in diameter, about 170 μm in diameter, about 180 μm in diameter, about 190 μm in diameter, about 200 μm in diameter, about 210 μm in diameter, about 220 μm in diameter, about 230 μm in diameter, about 240 μm in diameter, about 250 μm in diameter, about 260 μm in diameter, about 270 μm in diameter, about 280 μm in diameter, about 290 μm in diameter, or about 300 μm in diameter. In some examples 60%, 70%, 80%, 90%, or 95% of the particles in micronized Form VI have a diameter less than about 5 μm. In some examples 60%, 70%, 80%, 90%, or 95% of the particles in micronized Form VI have a diameter less than about 10 μm. In some examples 60%, 70%, 80%, 90%, or 95% of the particles in micronized Form VI have a diameter less than about 20 μm.

In some embodiments, the chemical purity of the polymorph Form VI is greater than 60%, 70%, 80%, 90%, 95%, or 99%. In some embodiments, the chemical purity of the polymorph Form VI is greater than about 90%. In some embodiments, the chemical purity of the polymorph Form VI is greater than about 95%. In some embodiments, the chemical purity of the polymorph Form VI greater than about 99%. The chemical purity of polymorph VI may be measured by any available analytical technique, for example by HPLC analysis.

In various embodiments, the polymorph Form VI of the compound of Formula I is dry. In various embodiments, the polymorph Form VI of the compound of Formula I is non-solvated. In some embodiments, the polymorph Form VI of the compound of Formula I is solvated.

In various embodiments, the polymorph Form VI of the compound of Formula I is characterized by an endotherm at about 120-147° C., for example at about 120-145° C., 120-143° C., 120-141° C., 120-140° C., 120-139° C., 120-135° C., 120-133° C., 120-131° C., 120-129° C., 127-145° C., 127-143° C., 127-141° C., 127-139° C., 127-135° C., 127-133° C., 127-131° C., 127-129° C., 129-147° C., 129-145° C., 129-143° C., 129-141° C., 129-139° C., 129-135° C., 129-133° C., 129-131° C., 131-147° C., 131-145° C., 131-143° C., 131-141° C., 131-139° C., 131-135° C., 131-133° C., 133-147° C., 133-145° C., 133-143° C., 133-141° C., 133-139° C., 133-135° C., 135-147° C., 135-145° C., 135-143° C., 135-141° C., 135-139° C., 135-137° C., 137-147° C., 137-145° C., 137-143° C., 137-141° C., 137-139° C., 139-147° C., 139-145° C., 139-143° C., 139-141° C., 141-147° C., 141-145° C., 141-143° C., 143-147° C., 143-145° C., or 145-147° C. in the DSC trace. In various embodiments, the polymorph Form VI of the compound of Formula I is characterized by an endotherm at about 179-199° C. in the DSC trace, for example at about 179-197° C., 179-195° C., 179-193° C., 179-191° C., 179-189° C., 179-187° C., 179-185° C., 179-183° C., 179° C.-181° C., 181-197° C., 181-195° C., 181-193° C., 181-191° C., 181-189° C., 181-187° C., 181-185° C., 181-183° C., 183-197° C., 183-195° C., 183-193° C., 183-191° C., 183-189° C., 183-

187° C., 183-185° C., 185-197° C., 185-195° C., 185-193° C., 185-191° C., 185-189° C., 185-187° C., 187-197° C., 187-195° C., 187-193° C., 187-191° C., 187-189° C., 189-197° C., 189-195° C., 189-193° C., 189-191° C., 191-197° C., 191-195° C., 191-193° C., 193-197° C., 193-195° C., or 195-197° C.

In some embodiments the melting point of the polymorph Form VI of the compound of Formula I is about 185-191° C., for example about 185° C., 186° C., 187° C., 188° C., 189° C., 190° C., or 191° C. In some embodiments, the melting point of the polymorph Form VI of the compound of Formula I is about 188° C.

In various embodiments, the polymorph Form VI of the compound of Formula I is stable at room temperature. In some examples, the polymorph Form VI can be stored at room temperature for extended period of time without significant chemical degradation or change in the crystalline form. In some examples, the polymorph Form VI can be stored at room temperature for a time period of at least about 10 days, 30 days, 60 days, 90 days, or 120 days. In some examples, the polymorph Form VI can be stored at room temperature for a time period of at most about 120 days. In some examples, the polymorph Form VI can be stored at room temperature for a time period of 10-14 days, 10-18 days, 10-22 days, 10-26 days, 10-30 days, 10-40 days, 10-50 days, 10-60 days, 10-90 days, 10-120 days, 14-18 days, 14-22 days, 14-26 days, 14-30 days, 14-40 days, 14-50 days, 14-60 days, 14-90 days, 14-120 days, 18-22 days, 18-26 days, 18-30 days, 18-40 days, 18-50 days, 18-60 days, 18-90 days, 18-120 days, 22-26 days, 22-30 days, 22-40 days, 22-50 days, 22-60 days, 22-90 days, 22-120 days, 26-30 days, 26-40 days, 26-50 days, 26-60 days, 26-90 days, 26-120 days, 30-40 days, 30-50 days, 30-60 days, 30-90 days, 30-120 days, 40-50 days, 40-60 days, 40-90 days, 40-120 days, 50-60 days, 50-90 days, 50-120 days, 60-90 days, 60-120 days, or 90-120 days. In some examples, the polymorph Form VI can be stored at room temperature for a time period of at least 10 days, 14 days, 18 days, 22 days, 26 days, 30 days, 40 days, 50 days, 60 days, 90 days, or 120 days.

In various embodiments, the polymorph Form VI of the compound of Formula I is stable at temperatures above the room temperature and/or at high RH. In some examples, the polymorph Form VI can be stored at about 40° C. at about 75% RH for an extended period of time without significant chemical degradation or change in the crystalline form. In some examples, the polymorph Form VI can be stored at 40° C. and at about 75% RH for a time period of at least about 10 days, 30 days, 60 days, 90 days, or 120 days. In some examples, the polymorph Form VI can be stored at 40° C. and at about 75% RH for a time period of at most about 120 days. In some examples, the polymorph Form VI can be stored at 40° C. and at about 75% RH for a time period of 10-14 days, 10-18 days, 10-22 days, 10-26 days, 10-30 days, 10-40 days, 10-50 days, 10-60 days, 10-90 days, 10-120 days, 14-18 days, 14-22 days, 14-26 days, 14-30 days, 14-40 days, 14-50 days, 14-60 days, 14-90 days, 14-120 days, 18-22 days, 18-26 days, 18-30 days, 18-40 days, 18-50 days, 18-60 days, 18-90 days, 18-120 days, 22-26 days, 22-30 days, 22-40 days, 22-50 days, 22-60 days, 22-90 days, 22-120 days, 26-30 days, 26-40 days, 26-50 days, 26-60 days, 26-90 days, 26-120 days, 30-40 days, 30-50 days, 30-60 days, 30-90 days, 30-120 days, 40-50 days, 40-60 days, 40-90 days, 40-120 days, 50-60 days, 50-90 days, 50-120 days, 60-90 days, 60-120 days, or 90-120 days. In some examples, the polymorph Form VI can be stored at 40° C. at about 75% RH for a time period of at least 10 days, 14 days, 18 days, 22 days, 26 days, 30 days, 40 days, 50 days, 60 days, 90 days, or 120 days.

In some examples, the polymorph Form VI of the compound of Formula I can be stored at about 60° C. for an extended period of time without significant chemical degradation or change in the crystalline form. In some examples, the polymorph Form VI can be stored at 60° C. for a time period of at least about 10 days, 30 days, 60 days, 90 days, or 120 days. In some examples, the polymorph Form VI can be stored at 60° C. for a time period of at most about 120 days. In some examples, the polymorph Form VI can be stored at 60° C. for a time period of 10-14 days, 10-18 days, 10-22 days, 10-26 days, 10-30 days, 10-40 days, 10-50 days, 10-60 days, 10-90 days, 10-120 days, 14-18 days, 14-22 days, 14-26 days, 14-30 days, 14-40 days, 14-50 days, 14-60 days, 14-90 days, 14-120 days, 18-22 days, 18-26 days, 18-30 days, 18-40 days, 18-50 days, 18-60 days, 18-90 days, 18-120 days, 22-26 days, 22-30 days, 22-40 days, 22-50 days, 22-60 days, 22-90 days, 22-120 days, 26-30 days, 26-40 days, 26-50 days, 26-60 days, 26-90 days, 26-120 days, 30-40 days, 30-50 days, 30-60 days, 30-90 days, 30-120 days, 40-50 days, 40-60 days, 40-90 days, 40-120 days, 50-60 days, 50-90 days, 50-120 days, 60-90 days, 60-120 days, or 90-120 days. In some examples, the polymorph Form VI can be stored at 60° C. for a time period of at least 10 days, 14 days, 18 days, 22 days, 26 days, 30 days, 40 days, 50 days, 60 days, 90 days, or 120 days.

In some examples, the polymorph Form VI of the compound of Formula I can be stored at about 100° C. for an extended period of time without significant chemical degradation or change in the crystalline form. In some examples, the polymorph Form VI of the compound of Formula I can be stored at 100° C. for a time period of at least about 10 days, 30 days, 60 days, 90 days, or 120 days. In some examples, the polymorph Form VI of the compound of Formula I can be stored at 100° C. for a time period of at most about 120 days. In some examples, the polymorph Form VI of the compound of Formula I can be stored at 100° C. for a time period of 10-14 days, 10-18 days, 10-22 days, 10-26 days, 10-30 days, 10-40 days, 10-50 days, 10-60 days, 10-90 days, 10-120 days, 14-18 days, 14-22 days, 14-26 days, 14-30 days, 14-40 days, 14-50 days, 14-60 days, 14-90 days, 14-120 days, 18-22 days, 18-26 days, 18-30 days, 18-40 days, 18-50 days, 18-60 days, 18-90 days, 18-120 days, 22-26 days, 22-30 days, 22-40 days, 22-50 days, 22-60 days, 22-90 days, 22-120 days, 26-30 days, 26-40 days, 26-50 days, 26-60 days, 26-90 days, 26-120 days, 30-40 days, 30-50 days, 30-60 days, 30-90 days, 30-120 days, 40-50 days, 40-60 days, 40-90 days, 40-120 days, 50-60 days, 50-90 days, 50-120 days, 60-90 days, 60-120 days, or 90-120 days. In some examples, the polymorph Form VI of the compound of Formula I can be stored at 100° C. for a time period of at least 10 days, 14 days, 18 days, 22 days, 26 days, 30 days, 40 days, 50 days, 60 days, 90 days, or 120 days.

Polymorph Form VIII of the Compound of Formula I

In one embodiment, the desired polymorph is Form VIII of the compound of Formula I, and the isolating step involves drying the polymorph Form VI of the compound of Formula I. In some embodiments, the drying is performed in an oven at a temperature above the ambient temperature. In some embodiments, the drying is performed at a temperature of about 100° C., about 95° C., about 90° C., about 85° C., about 80° C., about 75° C., about 70° C., about 65° C., about 60° C., about 55° C., about 50° C., about 45° C. or about 40° C. In various embodiments, the drying is performed for a time period of about 1 hour to about 5 days, for example for about 1 hour, 2 hour, 4 hour, 6 hour, 8 hour, 10 hour, 12 hour, 14 hour, 16 hour, 18 hour, 20 hour, 22 hour, 24 hour, 1.5 days, 2 days, 2.5 days, 3 days, 3.5 days, 4 days, 4.5 days or about 5 days.

In some embodiments, Form VI is dried in an oven at a temperature of about 80° C. for a time period of about 2 days and the resulting product is polymorph Form VIII.

In some embodiments, the chemical purity of the polymorph Form VIII is greater than 60%, 70%, 80%, 90%, 95%, or 99%. In some embodiments, the chemical purity of the polymorph Form VIII is greater than about 90%. In some embodiments, the chemical purity of the polymorph Form VIII is greater than about 95%. In some embodiments, the chemical purity of the polymorph Form VIII greater than about 99%. The chemical purity of polymorph VIII may be measured by any available analytical technique, for example by HPLC analysis.

In various embodiments, the polymorph Form VIII is dry. In various embodiments, the polymorph Form VIII is non-solvated. In some embodiments, the polymorph Form VIII is solvated.

In various embodiments, the polymorph Form VIII is characterized by an endotherm at about 179-199° C., for example at about 179-197° C., 179-195° C., 179-193° C., 179-191° C., 179-189° C., 179-187° C., 179-185° C., 179-183° C., 179-181° C., 181-199° C., 181-197° C., 181-195° C., 181-193° C., 181-191° C., 181-189° C., 181-187° C., 181-185° C., 181-183° C., 182-192° C., 183-199° C., 183-197° C., 183-195° C., 183-193° C., 183-191° C., 183-189° C., 183-187° C., 183-185° C., 185-199° C., 185-197° C., 185-195° C., 185-193° C., 185-191° C., 185-189° C., 185-187° C., 187-199° C., 187-197° C., 187-195° C., 187-193° C., 187-191° C., 187-189° C., 189-199° C., 189-197° C., 189-195° C., 189-193° C., 189-191° C., 191-199° C., 191-197° C., 191-195° C., 191-193° C., 193-199° C., 193-197° C., 193-195° C., 195-199° C., 195-197° C., or 195-199° C. In some embodiments, the polymorph Form VIII is characterized by a endotherm at about 187° C.

In some embodiments, the DSC thermogram further comprises endotherm at about 114° C. In some embodiments, the DSC thermogram further comprises endotherm at about 110-135° C. for example at about 110-133, 110-131, 110-129, 110-127, 110-125, 110-123, 110-121, 110-119, 110-117, 110-115, 110-113, 113-135, 113-133, 113-131, 113-129, 113-127, 112-125, 113-123, 113-121, 113-119, 113-117, 113-115, 115-135, 115-133, 115-131, 115-129, 115-127, 115-125, 115-123, 115-121, 115-119, 115-117, 117-135, 117-133, 117-131, 117-129, 117-127, 117-125, 117-135, 117-131, 117-129, 117-127, 117-125, 117-123, 117-121, 117-119, 119-135, 119-133, 119-131, 119-129, 119-127, 119-125, 119-123, 119-121, 121-135, 121-133, 121-131, 121-129, 121-127, 121-125, 121-123, 123-135, 123-133, 123-131, 123-129, 123-127, 123-125, 125-135, 125-133, 125-131, 125-129, 125-127, 127-135, 127-133, 127-131, 127-129, 129-135, 129-133, 129-131, 131-135, 131-133, or 133-135° C. In some embodiments, the DSC thermogram further comprises endotherm at about 114° C.

III. Methods of Treatments

In some embodiments, the various polymorphs of the compound of Formula I bind to a kinase including, but not limited to, Abl, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3alpha, Gsk3beta, HCK, Her2/Erbb2, Her4/Erbb4, IGF1R, IKK beta, Irak4, Itk, Jak1, Jak2, Jak3, Jnk1, Jnk2, Jnk3, KDR, Kit, Lck, Lyn, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, ROCK1, ROCK2, Ron, Src, Stk6, Syk, TEC, Tie2, TrkA, TrkB, Yes, and Zap70, including any mutated versions thereof. For example, the polymorphs of the compound of Formula I bind to a kinase selected from the group consisting of EGFR, HER2, HER4, KDR, ALK, ARKS, BLK, BTK, FMS, ITK, JAK1, JAK2, JAK3, PLK1, PLK2, PLK3, PLK4, FAK, and SNARK. In some embodiments, the polymorphs of the compound of Formula I bind to a kinase selected from the group consisting of EGFR mutants such as EGFR del E746-A750, EGFR del E747-E749/A750P, EGFR del E747-S752/P753S, EGFR del E747-T751/Sins/A750P, EGFR del S752-1759, EGFR G719S, EGFR G719C, EGFR L861Q, EGFR L858R, EGFR T790M, EGFR L858R/T790M. For example, the polymorphs of the compound of Formula I bind to a kinase which is EGFR L858R, EGFR T790M or EGFR L858R/T790M mutant. In some embodiments, the polymorphs of the compound of Formula I bind to a kinase including, but not limited to, Abl, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3alpha, Gsk3beta, HCK, Her2/Erbb2, Her4/Erbb4, IGF1R, IKK beta, Irak4, Itk, Jak1, Jak2, Jak3, Jnk1, Jnk2, Jnk3, KDR, Kit, Lck, Lyn, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, ROCK1, ROCK2, Ron, Src, Stk6, Syk, TEC, Tie2, TrkA, TrkB, Yes, and Zap70, including any mutated versions thereof, with a Kd which is lower than 50 μM, 25 μM, 10 μM, 5 μM, or 1 μM as measured in an in vitro assay. For example, the polymorphs of the compound of Formula I bind to a kinase selected from the group consisting of EGFR, EGFR L858R, EGFR T790M, EGFR del E746-A750, or EGFR L858R/T790M mutant, Her2, Her4, Fak, FGFR1, FGFR2, FGFR3, FGFR4, Btk, Met, Pim1, Pim2, Pim3, Pyk2, KDR, Src and Ret, and any mutated versions thereof with a Kd which is lower than 50 μM, 25 μM, 10 μM, 5 or 1 μM as measured in an in vitro assay. In some embodiments, the polymorphs of the compound of Formula I bind to a kinase selected from the group consisting of Btk, KDR, EGFR, EGFR L858R, EGFR T790M or EGFR L858R/T790M mutant with a Kd which is lower than 50 μM, 10 μM, 5 μM, or 1 μM as measured in an in vitro assay. For example, the polymorphs of the compound of Formula I bind to a kinase which is EGFR, EGFR L858R, EGFR T790M, EGFR del E746-A750, EGFR L858R/T790M mutant with a Kd which is lower than 50 μM, 25 μM, 5 μM, or 1 μM as measured in an in vitro assay.

In some embodiments, the polymorphs of the compound of Formula I inhibit a kinase including, but not limited to, Abl, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3alpha, Gsk3beta, HCK, Her2/Erbb2, Her4/Erbb4, IGF1R, IKK beta, Irak4, Itk, Jak1, Jak2, Jak3, Jnk1, Jnk2, Jnk3, KDR, Kit, Lck, Lyn, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, ROCK1, ROCK2, Ron, Src, Stk6, Syk, TEC, Tie2, TrkA, TrkB, Yes, and Zap70, including any mutated versions thereof. For example, the polymorphs of the compound of Formula I inhibit a kinase selected from the group consisting of EGFR, Btk, Fak, FGFR1, FGFR2, FGFR3, FGFR4, Jnk1, Jnk2, Jnk3, Lck, Lyn, Met, Pim1, Pim2, Pim3, Pyk2, KDR, Src and Ret, and any mutated versions thereof. In some embodiments, the polymorphs of the compound of Formula I inhibit a kinase selected from the group consisting of EGFR, EGFR L858R, EGFR del E746-A750, EGFR T790M or EGFR L858R/T790M mutant. For example, the polymorphs of the compound of Formula I inhibit a kinase which is EGFR or EGFR L858R/T790M mutant. In some embodiments, the polymorphs of the compound of Formula I inhibit a kinase including, but not limited to, Abl, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3alpha, Gsk3beta, HCK, Her2/Erbb2, Her4/Erbb4, IGF1R, IKK beta, Irak4, Itk, Jak1, Jak2, Jak3, Jnk1, Jnk2, Jnk3, KDR, Kit, Lck, Lyn, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, ROCK1, ROCK2, Ron, Src, Stk6, Syk, TEC, Tie2, TrkA, TrkB, Yes, and Zap70, including any mutated versions thereof with an $IC_{50}$ in an in vitro assay of 10 µM, 5 µM, 2 µM, 1 µM, 500 nM, 200 nM, 100 nM or less as ascertained in an in vitro kinase assay. For example, the polymorphs of the compound of Formula I inhibit a kinase selected from the group consisting of EGFR, HER2, HER3, HER4, KDR, ALK, ARKS, BLK, BTK, FGFR1, FGFR2, FGFR3, FMS, ITK, JAK1, JAK2, JAK3, PLK1, PLK2, PLK3, PLK4, FAK, and SNARK, Src and Ret, and any mutated versions thereof with an $IC_{50}$ in an in vitro assay of 10 µM, 5 µM, 2 µM, 1 µM, 500 nM, 200 nM, 100 nM or less as ascertained in an in vitro kinase assay. In some embodiments, the polymorphs of the compound of Formula I inhibit a kinase selected from the group consisting of EGFR, EGFR L858R, EGFR del E746-A750, EGFR T790M or EGFR L858R/T790M mutant with an $IC_{50}$ in an in vitro assay of 10 µM, 5 µM, 2 µM, 1 µM, 500 nM, 200 nM, 100 nM or less as ascertained in an in vitro kinase assay. For example, the polymorphs of the compound of Formula I inhibit a kinase which is EGFR or EGFR L858R/T790M mutant with an $IC_{50}$ in an in vitro assay of 10 µM, 5 µM, 2 µM, 1 µM, 500 nM, 200 nM, 100 nM or less as ascertained in an in vitro kinase assay.

In some embodiments, the polymorphs of the compound of Formula I inhibit the activity of one or more kinases selected from the group consisting of EGFR, EGFR L858R, EGFR T790M or EGFR L858R/T790M with an $IC_{50}$ in an in vitro assay of 1 µM, 500 nM, 200 nM, 100 nM, 50 nM, 25 nM or less as ascertained in an in vitro kinase assay.

In some embodiments, the polymorphs of the compound of Formula I selectively inhibit the activity of one or more kinases selected from the group consisting of Abl, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3alpha, Gsk3beta, HCK, Her2/Erbb2, Her4/Erbb4, IGF1R, IKK beta, Irak4, Itk, Jak1, Jak2, Jak3, Jnk1, Jnk2, Jnk3, KDR, Kit, Lck, Lyn, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, ROCK1, ROCK2, Ron, Src, Stk6, Syk, TEC, Tie2, TrkA, TrkB, Yes, and Zap70, including any mutated versions thereof. For example, the polymorphs of the compound of Formula I selectively inhibit the activity of one or more kinases selected from the group consisting of EGFR, EGFR L858R, EGFR T790M, EGFR del E746-A750 or EGFR L858R/T790M, HER2, HER3, HER4, KDR, ALK, ARKS, BLK, BTK, FGFR1, FGFR2, FGFR3, FMS, ITK, JAK1, JAK2, JAK3, PLK1, PLK2, PLK3, PLK4, FAK, and SNARK, Src and Ret, In some embodiments, the polymorphs of the compound of Formula I selectively inhibit the activity of one or more kinases selected from the group consisting of EGFR, EGFR L858R, EGFR T790M, EGFR del E746-A750 or EGFR L858R/T790M mutant.

In some embodiments, the polymorphs of the compound of Formula I selectively inhibits the activity of, EGFR L858R, EGFR T790M, EGFR del E746-A750, or EGFR L858R/T790M mutant relative to one or more kinases selected from the group consisting of ABL1, AKT1 (PKB alpha), AURKB (Aurora B), BLK, BTK, CDK1/cyclin B, CHEK1 (CHK1), CSF1R (FMS), CSNK1G2 (CK1 gamma 2), EGFR (ErbB1), FGFR1, FGFR2, FGFR3, FGR, FLT3, FRAP1 (mTOR), FYN, IGF1R, IKBKB (IKK beta), INSR, JAK1, JAK2, JAK3, KDR, KIT, LCK, LYN A, MAP2K1 (MEK1), MAP4K5 (KHS1), MAPK1 (ERK2), MAPK14 (p38 alpha), MAPKAPK2, MET (cMet), PDGFRB (PDGFR beta), PIK3CA/PIK3R1 (p110 alpha/p85 alpha)PRKCB2 (PKC beta II), PTK2B (FAK2), PTK6 (Brk), RAF1 (cRAF) Y340D Y341D, RET, RPS6KB1 (p70S6K), SRC, SRMS (Srm), and YES1. In some embodiments, the polymorphs of the compound of Formula I selectively inhibit the activity of one or more kinases selected from the group consisting of EGFR L858R, EGFR T790M EGFR del E746-A750, or EGFR L858R/T790M with an $IC_{50}$ which is ½, $1/3^{rd}$, $1/4^{th}$, $1/5^{th}$, $1/7^{th}$, $1/10^{th}$, $1/15^{th}$, $1/20^{th}$, $1/25^{th}$, $1/30^{th}$, $1/30^{th}$, $1/40^{th}$, $1/50^{th}$, $1/100^{th}$, $1/150^{th}$, $1/150^{th}$, $1/200^{th}$, $1/300^{th}$, $1/400^{th}$, $1/500^{th}$, $1/1000^{th}$, $1/1000^{th}$, $1/2000^{th}$ or less than the $IC_{50}$ for a kinase selected from the group consisting of ABL1, AKT1 (PKB alpha), AURKB (Aurora B), BLK, BTK, CDK1/cyclin B, CHEK1 (CHK1), CSNK1G2 (CK1 gamma 2), EGFR (ErbB1), FGFR1, FGFR2, FGFR3, FGR, FLT3, FRAP1 (mTOR), FYN, IGF1R, IKBKB (IKK beta), INSR, JAK1, JAK2, JAK3, KDR, KIT, LCK, LYN A, MAP2K1 (MEK1), MAP4K5 (KHS1), MAPK1 (ERK2), MAPK14 (p38 alpha), MAPKAPK2, MET (cMet), PDGFRB (PDGFR beta), PIK3CA/PIK3R1 (p110 alpha/p85 alpha)PRKCB2 (PKC beta II), PTK2B (FAK2), PTK6 (Brk), RAF1 (cRAF) Y340D Y341D, RET, RPS6KB1 (p70S6K), SRC, SRMS (Srm), and YES1.

In some embodiments, one or more polymorphs of the compound of Formula I are capable of inhibiting cellular proliferation. For example, in some embodiments, one or more polymorphs of the compounds of Formula I inhibit proliferation of tumor cells or tumor cell lines. For example, such cell lines express a kinase which is EGFR L858R, EGFR T790M, EGFR del E746-A750, or EGFR L858R/T790M mutant. In some embodiments, the one or more polymorphs of the compounds of Formula I inhibit A549, A431, HCC827 or H1975 cell proliferation in vitro or in an in vivo model such as a xenograft mouse model. In some embodiments, in vitro cultured HCC827 or H1975 cell proliferation may be inhibited with an $IC_{50}$ of less than 100 µM, 75 µM, 50 µM, 25 µM, 15 µM, 10 µM, 5 µM, 3 µM, 2 µM, 1 µM or less by one or more polymorphs of the compound of Formula I.

IV. Compositions and Formulations

The disclosure provides compositions, including pharmaceutical compositions, comprising one or more polymorphs of the present invention.

In various embodiments, the ratio of desired polymorph such as Form I to all other polymorphs in a composition is greater than about 1:1, 2:1, 3:1, 4:1, 5:1, 6:1, 7:1, 8:1, 9:1, or more w/w.

In various embodiments, the ratio of desired polymorph Form II to all other polymorphs is greater than about 1:1, 2:1, 3:1, 4:1, 5:1, 6:1, 7:1, 8:1, 9:1, or more w/w.

In various embodiments, the ratio of desired polymorph Form III to all other polymorphs is greater than about 1:1, 2:1, 3:1, 4:1, 5:1, 6:1, 7:1, 8:1, 9:1, or more w/w.

In various embodiments, the ratio of desired polymorph Form IV to all other polymorphs is greater than about 1:1, 2:1, 3:1, 4:1, 5:1, 6:1, 7:1, 8:1, 9:1, or more w/w.

In various embodiments, the ratio of desired polymorph Form V to all other polymorphs is greater than about 1:1, 2:1, 3:1, 4:1, 5:1, 6:1, 7:1, 8:1, 9:1, or more w/w.

In various embodiments, the ratio of desired polymorph Form VI to all other polymorphs is greater than about 1:1, 2:1, 3:1, 4:1, 5:1, 6:1, 7:1, 8:1, 9:1, or more w/w.

In various embodiments, the ratio of desired polymorph Form VII to all other polymorphs is greater than about 1:1, 2:1, 3:1, 4:1, 5:1, 6:1, 7:1, 8:1, 9:1, or more w/w.

In various embodiments, the ratio of desired polymorph Form VIII to all other polymorphs is greater than about 1:1, 2:1, 3:1, 4:1, 5:1, 6:1, 7:1, 8:1, 9:1, or more w/w.

In some embodiments, the one or more polymorphs of the compound of Formula I are formulated into pharmaceutical compositions. In specific embodiments, pharmaceutical compositions are formulated in a conventional manner using one or more physiologically acceptable carriers comprising excipients and auxiliaries which facilitate processing of the active compounds/polymorphs into preparations which can be used pharmaceutically. Proper formulation is dependent upon the route of administration chosen. Any pharmaceutically acceptable techniques, carriers, and excipients are used as suitable to formulate the pharmaceutical compositions described herein: *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and* Drug Delivery Systems, Seventh Ed. (Lippincott Williams & Wilkins 1999).

Provided herein are pharmaceutical compositions comprising one or more polymorphs of the compound of Formula I and a pharmaceutically acceptable diluent(s), excipient(s), or carrier(s). In certain embodiments, the one or more polymorphs of the compound of Formula I are administered as pharmaceutical compositions in which the one or more polymorphs, are mixed with other active ingredients, as in combination therapy. Encompassed herein are all combinations of actives set forth in the combination therapies section below and throughout this disclosure. In specific embodiments, the pharmaceutical compositions include one or more polymorphs of the compound of Formula I.

A pharmaceutical composition, as used herein, refers to a mixture of one or more polymorphs of the compound of Formula I with other chemical components, such as carriers, stabilizers, diluents, dispersing agents, suspending agents, thickening agents, and/or excipients. In certain embodiments, the pharmaceutical composition facilitates administration of the polymorphs to an organism. In some embodiments, in practicing the methods of treatment or use provided herein, therapeutically effective amounts of one or more polymorphs of the compound of Formula I are administered in a pharmaceutical composition to a mammal having a disease or condition to be treated. In specific embodiments, the mammal is a human. In certain embodiments, therapeutically effective amounts vary depending on the severity of the disease, the age and relative health of the subject and other factors. The one or more polymorphs of the compound of Formula I described herein are used singly or in combination with one or more therapeutic agents as components of mixtures.

In one embodiment, one or more polymorphs of the compound of Formula I are formulated in an aqueous solution. In specific embodiments, the aqueous solution is selected from, by way of example only, a physiologically compatible buffer, such as Hank's solution, Ringer's solution, or physiological saline buffer. In other embodiments, one or more polymorphs of the compound of Formula I are formulated for transmucosal administration. In specific embodiments, transmucosal formulations include penetrants that are appropriate to the barrier to be permeated. In still other embodiments wherein the one or more polymorphs described herein are formulated for other parenteral injections, appropriate formulations include aqueous or nonaqueous solutions. In specific embodiments, such solutions include physiologically compatible buffers and/or excipients.

In another embodiment, the polymorphs described herein are formulated for oral administration. The polymorphs of the compound of Formula I are formulated by combining the polymorphs with, e.g., pharmaceutically acceptable carriers or excipients. In various embodiments, the polymorphs described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the polymorphs described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the polymorphs described herein is formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the polymorphs described herein are formulated for buccal or sublingual administration. Formulations suitable for buccal or sublingual administration include, by way of example only, tablets, lozenges, or gels. In still other embodiments, the polymorphs described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical composition of a polymorph of the compound of Formula I is formulated in a form suitable for parenteral injection as sterile suspension, solution or emulsion in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active polymorphs in water-soluble form. In additional embodiments, suspensions of the active polymorphs are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the polymorphs to allow for the preparation of highly concentrated solutions. Alternatively, in other embodiments, the active ingredient is in powder form for constitution with a suitable vehicle, e.g., sterile pyrogen-free water, before use.

In still other embodiments, the one or more polymorphs of the compound of Formula I are administered topically. The one or more polymorphs described herein are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the one or more polymorphs of the compound of Formula I are formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of the one or more polymorphs of the compound of Formula I is accomplished by means of iontophoretic patches and the like. In certain embodiments, transdermal patches provide controlled delivery of the one or more polymorphs of the compound of Formula I. In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In other embodiments, the one or more polymorphs of the compound of Formula I are formulated for administration by inhalation. Various forms suitable for administration by inhalation include, but are not limited to, aerosols, mists or powders. Pharmaceutical compositions of the polymorphs of the compound of Formula I are conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatin for use in an inhaler or insufflator are formulated containing a powder mix of the compound and a suitable powder base such as lactose or starch.

In still other embodiments, the one or more polymorphs of the compound of Formula I are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active polymorphs into preparations which can be used pharmaceutically. Proper formulation is dependent upon the route of administration chosen. Any pharmaceutically acceptable techniques, carriers, and excipients are optionally used as suitable. Pharmaceutical compositions comprising the one or more polymorphs of the compound of Formula I are manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one polymorph of the compound of Formula I described herein as an active ingredient. The active ingredient is in free-acid or free-base form, or in a pharmaceutically acceptable salt form. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions, comprising the one or more polymorphs of the compound of Formula I described herein include formulating the polymorphs with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, a pharmaceutical composition comprising at least one polymorph of the compound of Formula I illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, useful aqueous suspension contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Useful pharmaceutical compositions also, optionally, include solubilizing agents to aid in the solubility of a polymorph of the compound of Formula I. The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, useful pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, useful compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other useful pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other useful compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other useful compositions include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers useful herein. In certain embodiments, organic solvents such as N-methylpyrrolidone are also employed. In additional embodiments, the polymorphs described herein are delivered using a sustained-release system, such as semipermeable matrices of solid hydrophobic polymers containing the therapeutic agent. Various sustained-release materials are useful herein. In some embodiments, sustained-release capsules release the polymorphs for a few weeks up to over 100 days. Depending on the chemical nature and the biological stability of the therapeutic reagent, additional strategies for protein stabilization are employed.

In certain embodiments, the formulations described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

V. Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a polymorph as described herein is administered in a local rather than systemic manner, for example, via injection of the polymorph directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the polymorph as described herein is provided in the form of a rapid release formulation, in the form of an extended release formulation, or in the form of an intermediate release formulation. In yet other embodiments, the polymorph described herein is administered topically.

VI. Kits/Articles of Manufacture

For use in the therapeutic applications described herein, kits and articles of manufacture are also provided. In some embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from a variety of materials such as glass or plastic.

The articles of manufacture provided herein contain packaging materials. Packaging materials for use in packaging pharmaceutical products Include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) includes one or more polymorphs described herein, optionally in a composition or in combination with another agent as disclosed herein. The container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

For example, a kit typically includes one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical composition is presented in a pack or dispenser device which contains one or more unit dosage forms containing a compound provided herein. The pack for example contains metal or plastic foil, such as a blister pack. Or, the pack or dispenser device is accompanied by instructions for administration. Or, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a polymorph provided herein formulated in a compatible pharmaceutical carrier are prepared, placed in an appropriate container, and labeled for treatment of an indicated condition.

VII. Methods of Use

The polymorphs described herein are useful in the treatment, or in the preparation of a medicament for the treatment of various disorders. For example, the polymorphs of the compound of Formula I are useful as inhibitors of protein kinases. In some embodiments, the polymorphs described herein are inhibitors of one or more kinases. For example, the polymorphs of the compound of Formula I are inhibitors of EGFR and of mutants of such kinase, including the EGFR del E746-A750, EGFR del E747-E749/A750P, EGFR del E747-S752/P753S, EGFR del E747-T751/Sins/A750P, EGFR del S752-1759, EGFR G719S, EGFR G719C, EGFR L861Q, EGFR L858R, EGFR T790M or EGFR L858R/T790M mutant. Thus, without wishing to be bound by any particular theory, the polymorphs of the compound of Formula I are particularly useful for treating or lessening the severity of a disease, condition, or disorder where activation of one or more kinases, such as EGFR, which is implicated in the disease, condition, or disorder. When activation of EGFR kinase is implicated in a particular disease, condition, or disorder, the disease, condition, or disorder may also be referred to as "EGFR-mediated disease" or disease symptom. Accordingly, in another aspect, the present invention provides a method for treating or lessening the severity of a disease, condition, or disorder where activation of EGFR and/or other kinases is implicated in the disease state.

The inhibition of kinases may be assayed in vitro, in vivo or in a cell line. In vitro assays include assays that determine inhibition of either the phosphorylation activity or ATPase activity of activated kinase. Alternate in vitro assays quantitate the ability of the inhibitor to bind to kinase. Inhibitor binding may be measured by radiolabelling the inhibitor prior to binding, isolating the inhibitor, complex and determining the amount of radiolabel bound. Alternatively, inhibitor binding may be determined by running a competition experiment where new inhibitors are incubated with kinase bound to known radioligands. At 1 micro-molar concentration, one or more polymorphs of the present invention exhibits at least about 50%, 60%, 70, 80%, 90% or even higher inhibition of kinases including EGFR, EGFR L858R, EGFR del E746-A750, EGFR T790M or EGFR L858R/T790M.

The polymorphs of the compound of Formula I described herein may be prepared in substantially pure form, typically by standard chromatographic methods, prior to formulation in a pharmaceutically acceptable form.

The polymorphs of the compound of Formula I described herein may be used in treating a variety of cancers. Cancers that can be prevented and/or treated by the chemical entities, compositions, and methods described herein include, but are not limited to, human sarcomas and carcinomas, e.g. carcinomas, e.g., colon carcinoma, pancreatic cancer, breast cancer, ovarian cancer, prostate cancer, thyroid cancer, fibrosarcoma, myxosarcoma, liposarcoma, chondrosarcoma, osteogenic sarcoma, chondroma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease.

In some embodiments, the polymorphs of the compound of Formula I described herein are used for the treatment of cancers of the:
  i. digestive system including, without limitation, the esophagus, stomach, small intestine, colon (including colorectal), liver & intrahepatic bile duct, gallbladder & other biliary, pancreas, and other digestive organs;
  ii. respiratory system, including without limitation, larynx, lung & bronchus, and other respiratory organs;
  iii. skin;
  iv. thyroid;
  v. breast;
  vi. genital system, including without limitation, uterine cervix, ovary, and prostate;
  vii. urinary system, including without limitation, urinary bladder and kidney and renal pelvis; and
  viii. oral cavity & pharynx, including without limitation, tongue, mouth, pharynx, and other oral cavity.

In some embodiments, the polymorphs of the compound of Formula I described herein are used for the treatment of colon cancer, liver cancer, lung cancer, melanoma, thyroid cancer, breast cancer, ovarian cancer, and oral cancer.

The polymorphs of the compound of Formula I may also be used in conjunction with other well known therapeutic agents that are selected for their particular usefulness against the condition that is being treated. For example, the polymorphs of the compound of Formula I may be useful in combination at least one additional anti-cancer and/or cytotoxic agents. Further, the polymorphs of the compound of Formula I may also be useful in combination with other inhibitors of parts of the signaling pathway that links cell surface growth factor receptors to nuclear signals initiating cellular proliferation.

Such known anti-cancer and/or cytotoxic agents that may be used in combination with the chemical entities described herein include:

(i) antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumor antibiotics (for example anthracyclines like adriamycin, bleomycin, doxorubicin, daunomycin, epirubicin, idarubicin, mitomycinC, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5a-reductase such as finasteride;

(iii) anti-invasion agents [for example c-Src kinase family inhibitors like 4-(6-chloro-2,3methylenedioxyanilino)-7-[2-(4-methylpiperazin-1-yl)ethoxy]-5-tetrahydropyran-4yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4ylamino}thiazole-5-carboxamide (dasatinib, BMS-354825; J. Med. Chem., 2004, 47, 66586661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB 1 antibody cetuximab [Erbitux, C225] and any growth factor or growth factor receptor antibodies disclosed by Stem et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (RI15777) and lonafarnib (SCH66336)), inhibitors of cell signalling through MEK and/or AKT kinases, c-kit inhibitors, abl kinase inhibitors, P13 kinase inhibitors, Plt3 kinase inhibitors, CSF-IR kinase inhibitors, IGF receptor (insulin like growth factor) kinase inhibitors; aurora kinase inhibitors (for example AZD1152, PH739358, VX-680, MLN8054, R763, MP235, MP529, VX-528 and AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib(ZD6474), vatalanib (PTK787), sunitinib (SU11248), axitinib (AG-013736), pazopanib (GW 786034) and 4.{4-fluoro-2-methylindol-5-yloxy)-6-methoxy-7-(3pyrrolidin-1-ylpropoxy) quinazoline (AZD2171; Example 240 within WO 00/47212), compounds such as those disclosed in International Patent Applications WO 97/22596, WO 97/30035, WO 97/32856 and WO 98/13354 and compounds that work by other mechanisms (for example linomide, inhibitors of integrin av~3 function and angiostatin));

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan; (viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase subject tolerance to chemotherapy or radiotherapy such as multi-drug resistance gene therapy; and (x) immunotherapy approaches, including for example ex-vivo and in-vivo approaches to increase the immunogenicity of subject's tumor cells, such as transfection with cytokines such as interleukin 2, interleukin 4 or granulocyte-macrophage colony stimulating factor, approaches to decrease T-cell energy, approaches using transfected immune cells such as cytokine-transfected dendritic cells, approaches using cytokine-transfected tumor cell lines and approaches using anti-idiotypic antibodies.

In certain embodiments, the one or more polymorph of the compound of Formula I is administered in combination with one or more agents chosen from paclitaxel, bortezomib, dacarbazine, gemcitabine, trastuzumab, bevacizumab, capecitabine, docetaxel, erlotinib, aromatase inhibitors, such as AROMASIN™ (exemestane), and estrogen receptor inhibitors, such as FASLODEX™ (fulvestrant).

When a polymorph of the compound of Formula I is administered into a human subject, the daily dosage will normally be determined by the prescribing physician with the dosage generally varying according to the age, weight, and response of the individual subject, as well as the severity of the subject's symptoms.

In one exemplary application, a suitable amount of at least one polymorph of the compound of Formula I is administered to a mammal undergoing treatment for cancer, for example, breast cancer. Administration typically occurs in an amount of between about 0.01 mg/kg of body weight to about 100 mg/kg of body weight per day (administered in single or divided doses), such as at least about 0.1 mg/kg of body weight per day. A particular therapeutic dosage can include, e.g., from about 0.01 mg to about 1000 mg of the polymorph of the compound of Formula I, such as including, e.g., from about 1 mg to about 1000 mg. The quantity of the at least one polymorph of the compound of Formula I in a unit dose of preparation may be varied or adjusted from about 0.1 mg to 1000 mg, such as from about 1 mg to 300 mg, for example 10 mg to 200 mg, according to the particular application. The amount administered will vary depending on the particular $IC_{50}$ value of the at least one chemical entity used and the judgment of the attending clinician taking into consideration factors such as health, weight, and age. In combinational applications in which the at least one polymorph of the compound of Formula I is not the sole active ingredient, it may be possible to administer lesser amounts of the at least one polymorph and still have therapeutic or prophylactic effect.

In some embodiments, the pharmaceutical preparation is in unit dosage form. In such form, the preparation is subdivided into unit doses containing appropriate quantities of the at least one polymorph of the compound of Formula I e.g., an effective amount to achieve the desired purpose.

The actual dosage employed may be varied depending upon the requirements of the subject and the severity of the condition being treated. Determination of the proper dosage for a particular situation is within the skill of the art. Generally, treatment is initiated with smaller dosages which are less than the optimum dose of the at least one polymorph of the compound of Formula I. Thereafter, the dosage is increased by small amounts until the optimum effect under the circumstances is reached. For convenience, the total daily dosage may be divided and administered in portions during the day if desired.

The amount and frequency of administration of the at least one polymorph of the compound of Formula I and if applicable other chemotherapeutic agents and/or radiation therapy, will be regulated according to the judgment of the attending clinician (physician) considering such factors as age, condition and size of the subject as well as severity of the disease being treated.

The chemotherapeutic agent and/or radiation therapy can be administered according to therapeutic protocols well known in the art. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the subject, and in view of the observed responses of the disease to the administered therapeutic agents.

Also, in general, the at least one polymorph of the compound of Formula I need not be administered in the same pharmaceutical composition as a chemotherapeutic agent, and may, because of different physical and chemical characteristics, be administered by a different route. For example, the polymorph/compositions may be administered orally to generate and maintain good blood levels thereof, while the chemotherapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of polymorph (and where appropriate, chemotherapeutic agent and/or radiation) will depend upon the diagnosis of the attending physicians and their judgment of the condition of the subject and the appropriate treatment protocol.

The one or more polymorphs of the compound of Formula I (and where appropriate chemotherapeutic agent and/or radiation) may be administered concurrently (e.g., simultaneously, essentially simultaneously or within the same treatment protocol) or sequentially, depending upon the nature of the proliferative disease, the condition of the subject, and the actual choice of chemotherapeutic agent and/or radiation to be administered in conjunction (i.e., within a single treatment protocol) with the one or more polymorphs/composition.

In combinational applications and uses, the one or more polymorphs of Formula I and the chemotherapeutic agent and/or radiation need not be administered simultaneously or essentially simultaneously, and the initial order of administration of the one or more polymorphs of Formula I and the chemotherapeutic agent and/or radiation, may not be important. Thus, the at least one polymorph of Formula I may be administered first followed by the administration of the chemotherapeutic agent and/or radiation; or the chemotherapeutic agent and/or radiation may be administered first followed by the administration of the at least one polymorph of Formula I. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the subject. For example, the chemotherapeutic agent and/or radiation may be administered first, and then the treatment continued with the administration of the at least one polymorph of Formula I followed, where determined advantageous, by the administration of the chemotherapeutic agent and/or radiation, and so on until the treatment protocol is complete.

Thus, in accordance with experience and knowledge, the practicing physician can modify each protocol for the administration of a chemical entity/composition for treatment according to the individual subject's needs, as the treatment proceeds.

The attending clinician, in judging whether treatment is effective at the dosage administered, will consider the general well-being of the subject as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

EXAMPLES

The following examples serve to more fully describe the manner of using the invention. These examples are presented for illustrative purposes and should not serve to limit the true scope of the invention.

In carrying out the procedures of the methods described herein, it is of course to be understood that references to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

General Procedures

Example 1: Preparation of the Compound of Formula I (N-(3-(2-((2,3-difluoro-4-(4-(2-hydroxyethyl)piperazin-1-yl)phenyl)amino)quinazolin-8-yl)phenyl)acrylamide)

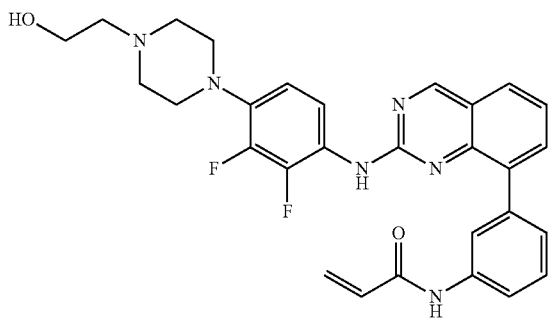

N-(3-(2-((2,3-difluoro-4-(4-(2-hydroxyethyl)piperazin-1-yl)phenyl)amino)quinazolin-8-yl)phenyl)acrylamide

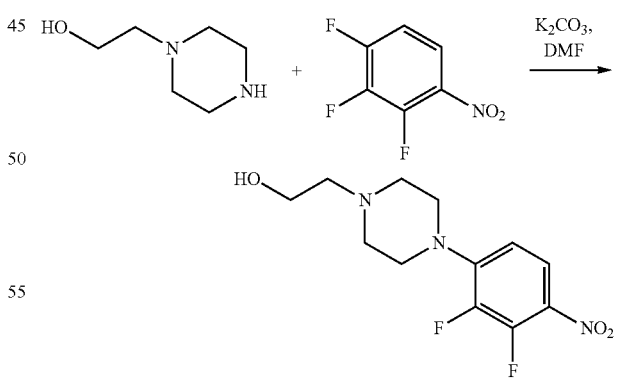

To a solution of 1,2,3-trifluoro-4-nitrobenzene (2.5 g, 14 mmol, 1.0 eq.) in DMF (20 mL) was added $K_2CO_3$ (3.8 g, 28 mmol, 2.0 eq.) followed by 2-(piperazin-1-yl)ethanol (1.8 g, 14 mmol, 1.0 eq.) at 0° C. and the mixture was stirred at r.t. overnight. The mixture was poured into ice-water (200 mL), filtered and dried in vacuo to afford 2-(4-(2,3-difluoro-4-nitrophenyl)piperazin-1-yl)ethanol (2.7 g, 67.5%).

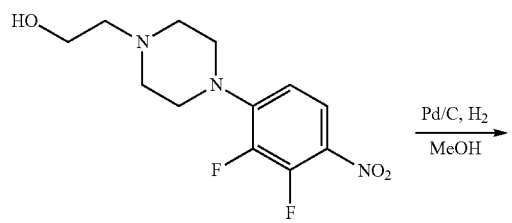

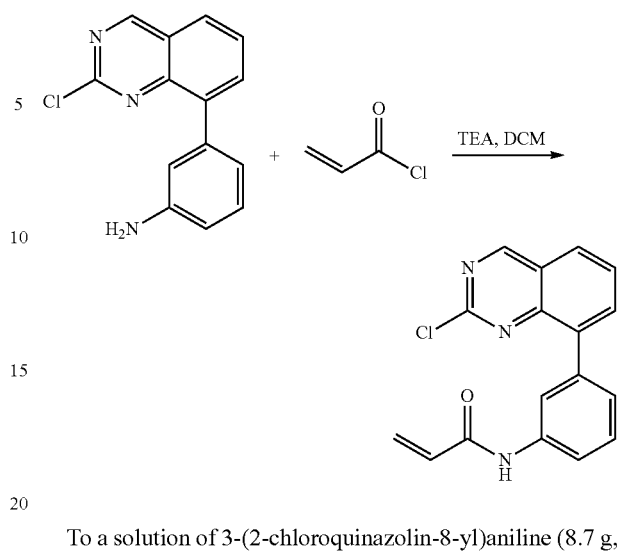

To a solution of 2-(4-(2,3-difluoro-4-nitrophenyl)piperazin-1-yl)ethanol (2.7 g, 9.0 mmol) in MeOH (30 mL) was added Pd/C (270 mg) and the resulting mixture was stirred at r.t. overnight. The Pd/C was removed by filtration and the filtrate was concentrated to afford 2-(4-(4-amino-2,3-difluorophenyl)piperazin-1-yl)ethanol (2.39 g, 99% yield) as off-white solid.

To a solution of 3-(2-chloroquinazolin-8-yl)aniline (8.7 g, 34 mmol, 1 eq.) in DCM (200 mL) cooled in ice-bath was added TEA (9.5 mL, 68 mmol, 2 eq.), followed by acryloyl chloride (4.1 mL, 51 mmol, 1.5 eq.) dropwise. The resulting mixture was stirred at r.t. for 1 h, then washed with brine, dried over anhydrous $N_2SO_4$, concentrated and the residue was purified via column chromatography (PE/EA=1:1, v:v) to afford N-(3-(2-chloroquinazolin-8-yl)phenyl)acrylamide as yellow solid(6.6 g, 65% yield).

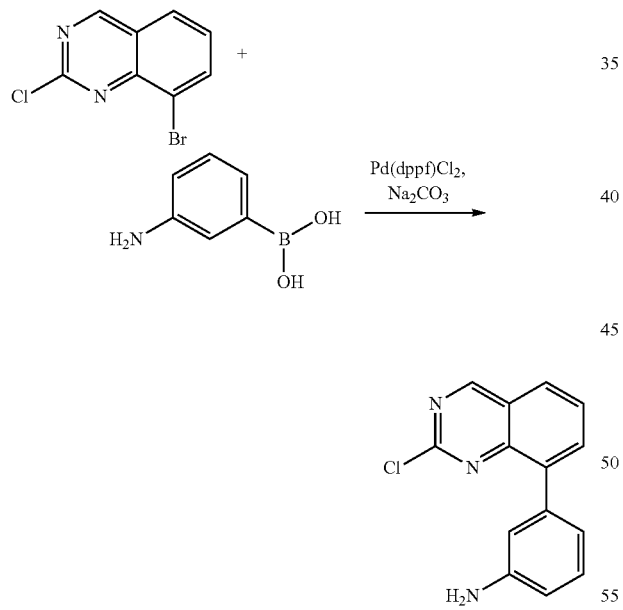

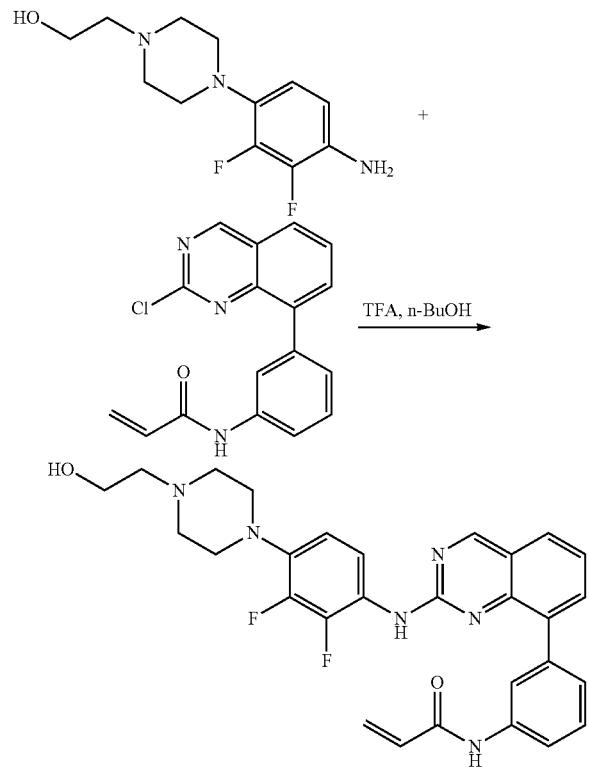

To a solution of 8-bromo-2-chloroquinazoline (15.4 g, 63.6 mmol, 1 eq.) and (3-aminophenyl)boronic acid (8.7 g, 63.6 mmol, 1 eq.) in dioxane/$H_2O$ (200 mL/20 mL) was added $Na_2CO_3$ (13.5 g, 127.2 mmol, 2 eq.), followed by Pd(dppf)$Cl_2$ (2.6 g, 3.2 mmol, 0.05 eq.) under $N_2$, then the mixture was stirred at 80° C. for 12 h. Then the solution was cooled to r.t., concentrated and the residue was purified via column chromatography (PE/EA=3:2, v/v) to afford 3-(2-chloroquinazolin-8-yl)aniline as yellow solid (8.7 g, 53.7% yield).

To a suspension of 2-(4-(4-amino-2,3-difluorophenyl)piperazin-1-yl)ethanol (83 mg, 0.32 mmol, 1 eq.) and N-(3-(2-chloroquinazolin-8-yl)phenyl)acrylamide (100 mg, 0.32 mmol, 1 eq.) in n-BuOH (5 mL) was added TFA (68 mg, 0.64 mmol, 2 eq.) and the resulting mixture was stirred at 90° C. overnight. The mixture was concentrated, diluted with DCM (20 mL), washed with Na$_2$CO$_3$ solution (20 mL), dried over anhydrous Na$_2$SO$_4$, concentrated and the residue was purified via column chromatography (MeOH/DCM=1/30, v:v) to afford N-(3-(2-((2,3-difluoro-4-(4-(2-hydroxyethyl)piperazin-1-yl)phenyl)amino)quinazolin-8-yl)phenyl)acrylamide as a yellow solid(16.3 mg, 9.5% yield). LRMS (M+H$^+$) m/z calculated 531.2, found 531.2. $^1$H NMR (CD$_3$OD, 400 MHz) δ 9.21 (s, 1H), 7.19-8.01 (m, 10H), 8.90 (s, 1H), 6.41-6.49 (m, 3H), 5.86 (m, 1H), 3.98-4.01 (m, 3H), 3.70-3.76 (m, 3H), 3.40-3.49 (m, 2H), 3.37-3.39 (m, 4H), 3.18 (m, 2H).

Example 2. Preparation of Form I of the Compound of Formula I

Crude compound of Formula I (~30 g, 75% of weight based assay) was dissolved in ethyl acetate (3 L) at 55-65° C. under nitrogen. The resulting solution was filtered via silica gel pad and washed with ethyl acetate (3 L×2) at 55-65° C. The filtrate was concentrated via vacuum at 30-40° C. to ~2.4 L. The mixture was heated up to 75-85° C. and maintained about 1 hour. Then cooled down to 50-60° C. and maintained about 2 hours. The heat-cooling operation was repeated again and the mixture was then cooled down to 20-30° C. and stirred for 3 hours. The resulting mixture was filtered and washed with ethyl acetate (60 mL×2). The wet cake was dried via vacuum at 30-40° C. to get (about 16 g) of the purified Form I of the compound of Formula I.

Example 3. Preparation of Form III of the Compound of Formula I

The compound of Formula I (2 g) was dissolved in EtOH (40 mL) at 75-85° C. under nitrogen. n-Heptane (40 mL) was added dropwise into reaction at 75-85° C. The mixture was stirred at 75-85° C. for 1 hour. Then cooled down to 50-60° C. and maintained about 2 hours. The heat-cooling operation was repeated again and continued to cool the mixture down to 20-30° C. and stirred for 3 hours. The resulting mixture was filtered and washed with EtOH/n-Heptane (1/1, 5 mL×2). The wet cake was dried via vacuum at 30-40° C. to get the purified Form III of the compound of Formula I (1.7 g).

Example 4. Preparation of Form IV of the Compound of Formula I

The crude compound of Formula I (15 g) was dissolved in ethyl acetate (600 mL) at 75-85° C. under nitrogen and treated with anhydrous Na$_2$SO$_4$, activated carbon, silica metal scavenger for 1 hour. The resulting mixture was filtered via neutral Al$_2$O$_3$ and washed with ethyl acetate (300 mL×2) at 75-85° C. The filtrate was concentrated under vacuum at 30-40° C. and swapped with DCM (150 mL). n-Heptane (75 mL) was added into this DCM solution at 35-45° C., and then the mixture was cooled down to 20-30° C. slowly. The resulting mixture was filtered and washed with DCM/n-Heptane (2/1, 10 mL×3). The wet cake was dried via vacuum at 35-40° C. to get the purified Form IV of the compound of Formula I (9.6 g).

Example 5. Preparation of Form V of the Compound of Formula I

Polymorph Form III of the compound of Formula I was dried in oven at 80° C. for 2 days to obtain the polymorph Form V.

Example 6. Preparation of Form VI of the Compound of Formula I

The compound of Formula I (1 g) was dissolved in IPA (20 mL) at 75-85° C. under nitrogen. n-Heptane (20 mL) was added dropwise into reaction at 75-85° C. The mixture was stirred at 45-55° C. for 16 hours. Then heated up to 75-85° C. and maintained about 0.5 hour. Then cooled down to 45-55° C. for 0.5 hour and continued to cool the mixture down to 20-30° C. and stirred for 3 hours. Filtered and washed with IPA/n-Heptane (1/1, 3 mL×2). The wet cake was dried via vacuum at 75-80° C. for 2 hours to get the purified Form VI of the compound of Formula I.

Example 7. Preparation of Form VIII of the Compound of Formula I

The polymorph Form VI of the compound of Formula I was dried in oven at 80° C. for 2 days to obtain the polymorph Form VIII.

Example 8. X-Ray Powder Diffraction (XRD)

X-ray powder diffraction (XRD) patterns were obtained on a Bruker D8 Advance. A CuK source (=1.54056 angstrom) operating minimally at 40 kV and 40 mA scans each sample between 4 and 40 degrees 2-theta. The step size is 0.05° C. and scan speed is 0.5 second per step.

Example 9. Thermogravimetric Analyses (TGA)

Thermogravimetric analyses were carried out on a TA Instrument TGA unit (Model TGA 500). Samples were heated in platinum pans from ambient to 300° C. at 10° C./min with a nitrogen purge of 60 mL/min (sample purge) and 40 mL/min (balance purge). The TGA temperature was calibrated with nickel standard, MP=354.4° C. The weight calibration was performed with manufacturer-supplied standards and verified against sodium citrate dihydrate desolvation.

Example 10. Differential Scanning Calorimetry (DSC)

Differential scanning calorimetry analyses were carried out on a TA Instrument DSC unit (Model DSC 1000 or 2000). Samples were heated in non-hermetic aluminum pans from ambient to 300° C. at 10° C./min with a nitrogen purge of 50 mL/min. The DSC temperature was calibrated with indium standard, onset of 156-158° C., enthalpy of 25-29 J/g.

Example 11. Hygroscopicity (DVS)

The moisture sorption profile was generated at 25° C. using a DVS Moisture Balance Flow System (Model Advantage) with the following conditions: sample size approximately 5 to 10 mg, drying 25° C. for 60 minutes, adsorption range 0% to 95% RH, desorption range 95% to 0% RH, and step interval 5%. The equilibrium criterion was <0.01% weight change in 5 minutes for a maximum of 120 minutes.

Example 12: Microscopy

Microscopy was performed using a Leica DMLP polarized light microscope equipped with 2.5×, 10× and 20× objectives and a digital camera to capture images showing particle shape, size, and crystallinity. Crossed polars were used to show birefringence and crystal habit for the samples dispersed in immersion oil.

Example 13: HPLC

HPLCs were preformed using the following instrument and/or conditions.

| | |
|---|---|
| Instrument | Agilent 1200 HPLC System |
| Column | Agilent Zora SB-C8, 4.6*75 mm, 3.5 μm |
| Mobile phase A | 0.1% TFA in Water |
| Mobile phase B | 0.1% TFA in Acetontrile |
| Diluent | EtOH/Water(1:1) |
| Flow rate | 1.0 ml/min |
| Column temp. | 30° C. |
| Wavelength | 268 nm |
| Injection volume | 10 μl |
| Acquisition time | 22 min |
| Post time | 5 min |

| | Time (min) | Flow rate (mL/min) | A (%) | B (%) |
|---|---|---|---|---|
| Gradient | 0 | 1.0 | 90 | 10 |
| | 3 | 1.0 | 65 | 35 |
| | 10 | 1.0 | 60 | 40 |
| | 13 | 1.0 | 40 | 60 |
| | 17 | 1.0 | 15 | 85 |
| | 20 | 1.0 | 15 | 85 |
| | 22 | 1.0 | 90 | 10 |

Example 14: Competitive Test of Form I and Form VI of the Compound of Formula I Two polymorphic forms of the compound of Formula I, Form I and Form VI, were suspended at the ratio of 1:1 in various solvents and equilibrated at room temperature for a period of time. The forms of the residual solid were checked at 7 days. If still a mixed form, continued to equilibrate at room temperature or 40° C. The solvents were EtOAc, iPoAc, Acetone, MEK, EtOH, IPA, IPE, MTBE, Hexane and Heptane. The sample preparation is summarized in Table 1.

TABLE 1

Competitive test between polymorph Form I and Form VI of the compound of Formula I

| No. | Solvent | Form I | Form VI |
|---|---|---|---|
| 1 | Ethyl acetate (EtOAc) | 29.2 mg | 28.0 mg |
| 2 | Isopropyl acetate (iPoAc) | 25.3 mg | 27.4 mg |
| 3 | Acetone | 25.8 mg | 26.1 mg |
| 4 | MEK | 26.3 mg | 27.0 mg |
| 5 | EtOH | 24.7 mg | 26.2 mg |
| 6 | IPA | 24.6 mg | 25.1 mg |
| 7 | Isopropyl ether (IPE) | 26.9 mg | 26.6 mg |
| 8 | MTBE | 27.2 mg | 27.3 mg |
| 9 | Hexane | 24.9 mg | 25.7 mg |
| 10 | Heptane | 29.3 mg | 27.6 mg |

XRPD profiles were acquired at the beginning and end of the experiment and compared to XRPD patterns of the known forms. As per the XRPD results, Form I was observed in Acetone, MEK by suspension equilibration for 7 days, EA, iPoAc by suspension equilibration for 14 days and MTBE by suspension equilibration for 21 days. Form VI was observed in IPA by suspension equilibration for 7 days. A mixed crystal of Form III and Form VI was observed in EtOH by suspension equilibration for 7 days. No form conversion was observed in IPE, Hexane and Heptane after equilibration for 21 days, and the samples were still a mix of Form I and Form VI. The detail information is listed in Table 2.

TABLE 2

Results of polymorph Form I and Form VI competitive test

| No. | Solvent | Check result at 7 days | Check result at 14 days | Check result at 21 days |
|---|---|---|---|---|
| 1 | Ethyl acetate (EtOAc) | Mixed, continue to equilibrate at 40° C. | Form I | NA |
| 2 | Isopropyl acetate (iPoAc) | Mixed, continue to equilibrate at 40° C. | Form I | NA |
| 3 | Acetone | Form I | NA | NA |
| 4 | MEK | Form I | NA | NA |
| 5 | EtOH | Form III and Form VI | NA | NA |
| 6 | IPA | Form VI | NA | NA |
| 7 | Isopropyl ether (IPE) | Continue to equilibrate at RT | Mixed, continue to equilibrate at 40° C. | Mixed |
| 8 | MTBE | Continue to equilibrate at RT | Mixed, continue to equilibrate at 40° C. | Form I |
| 9 | Hexane | Continue to equilibrate at RT | Mixed, continue to equilibrate at 40° C. | Mixed |
| 10 | Heptane | Continue to equilibrate at RT | Mixed, continue to equilibrate at 40° C. | Mixed |

NA = Not done

Example 15: Stability Tests of Form VI

Form VI of the compound of Formula I was used for the preliminary accelerated stability test. The samples were exposed to different stressed condition (40° C./75% RH and 60° C.) for 2 weeks. Standard controls were placed at −20° C. Samples and corresponding standard controls were pulled out for XRPD, DSC and HPLC analysis at 0 day, $1^{st}$ week and $2^{nd}$ week, respectively. The sample preparation information is listed in Table 3. The samples placed under condition without humidity were closed tightly with cap. The samples placed under humidity condition were just covered with aluminum foil with pinholes. HPLC steps were performed as described in Example 14.

TABLE 3

Accelerated stability sample preparation for Form VI

| Sample | Condition | Sample No. | 7 days-weight (mg) | 14 days-weight (mg) |
|---|---|---|---|---|
| Form VI | −20° C. | 1 | — | 3.028 |
|  |  | 2 | — | 3.117 |
|  |  | 3 | — | 3.082 |
|  |  | 4 | — | 3.374 |
|  | 40° C./75% RH | 1 | 3.333 | 3.074 |
|  |  | 2 | 3.316 | 3.360 |
|  |  | 3 (XRD, DSC) | 38.5 | 36.1 |
|  | 60° C. | 1 | 2.847 | 3.297 |
|  |  | 2 | 2.919 | 2.801 |
|  |  | 3 (XRD, DSC) | 42.7 | 35.7 |

Results of the stability tested by HPLC, XRPD and DSC are shown in Table 4. No significant degradation and crystal conversion were detected, Form VI of compound of Formula I seemed to be stable during the storage period.

Example 16: Stability Tests of Form I of the Compound of Formula I

Form I (both non-micronized and micronized) was used for the preliminary accelerated stability test. The samples were exposed to different stressed condition (40° C./75% RH and 60° C.) for 2 weeks. Standard controls were placed at −20° C. Samples and corresponding standard controls were pulled out for XRPD, DSC and HPLC analysis at 0 day, 1st week and 2nd week, respectively. The sample preparation information is listed in Table 5. The samples placed under condition without humidity were closed tightly with cap. The samples placed under humidity condition were just covered with aluminum foil with pinholes. HPLC steps were performed as described in Example 14.

TABLE 5

Accelerated stability sample preparation for Form I of the compound of Formula I

| Sample | Condition | Sample No. | 7 days (mg) | 14 days (mg) |
|---|---|---|---|---|
| non-micronized Form I | RT | 1 | 2.992 | — |
|  |  | 2 | 2.914 | — |
|  | 40° C./75% RH | 1 | 2.649 | 2.848 |
|  |  | 2 | 2.707 | 3.065 |
|  |  | 3 (XRD) | ~25 | ~25 |
|  | 60° C. | 1 | 3.035 | 2.698 |
|  |  | 2 | 2.728 | 2.798 |
|  |  | 3 (XRD) | ~25 | ~25 |
| micronized Form I | RT | 1 | 3.181 | — |
|  |  | 2 | 2.841 | — |
|  | 40° C./75% RH | 1 | 3.163 | 3.186 |
|  |  | 2 | 2.908 | 2.928 |
|  |  | 3 (XRD) | ~25 | ~25 |
|  | 60° C. | 1 | 2.861 | 3.220 |
|  |  | 2 | 3.146 | 3.22 |
|  |  | 3 (XRD) | ~25 | ~25 |

Results of the stability tested by HPLC, XRPD and DSC are shown in Table 6 and Table 7. No significant degradation and crystal conversion were detected, Form I of the compound of Formula I (non-micronized and micronized) seemed to be stable during the storage period.

TABLE 4

Solid stability data of Form VI of compound of Formula I.

| Sample type | Peak area | Peak area % | Assay % | Average assay (%) | Total impurity [b] (%) |
|---|---|---|---|---|---|
| Standard | 5003 | 99.2 | N/A | N/A | 0.85 |
|  | 5610 | 99.2 | N/A | N/A | 0.80 |
| −20° C. | 4980 | 99.0 | 92.15 | 92.21 | 0.95 |
|  | 5460 | 99.0 | 92.28 |  | 0.98 |
| 40° C.-75RH-7 days | 5369 | 99.1 | 91.85 | 91.67 | 0.95 |
|  | 5321 | 99.0 | 91.50 |  | 0.98 |
| 40° C.-75RH-14 days | 4966 | 99.0 | 92.13 | 91.79 | 0.99 |
|  | 5389 | 99.0 | 91.45 |  | 0.96 |
| 60° C.-7 days | 4574 | 98.9 | 91.61 | 92.68 | 1.10 |
|  | 4800 | 99.0 | 93.76 |  | 1.04 |
| 60° C.-14 days | 5309 | 99.0 | 91.82 | 91.80 | 1.01 |
|  | 4508 | 99.1 | 91.77 |  | 0.94 |

[b] Total impurity was calculated based on peak area normalized method.

TABLE 6

Solid stability data of non-micronized Form I of the compound of Formula I

| Sample type | Peak area | Peak area % | RRT 1.09 | Assay % | Average assay (%) | Total impurity (%) [b] | Average Total impurity (%) |
|---|---|---|---|---|---|---|---|
| Standard | 10435 | 99.16 | 0.162 | 100 | 100 | 0.84 | |
| RT | 9087 | 99.18 | 0.027 | 98.98 | 99.08 | 0.82 | 0.84 |
| | 8868 | 99.14 | 0.027 | 99.18 | | 0.86 | |
| 40° C.-75RH-7 d | 7988 | 99.12 | 0.027 | 98.28 | 98.44 | 0.88 | 0.88 |
| | 8189 | 99.12 | 0.032 | 98.59 | | 0.88 | |
| 40° C.-75RH-14 d | 8584 | 99.14 | 0.026 | 98.24 | 97.88 | 0.86 | 0.86 |
| | 9172 | 99.14 | 0.027 | 97.53 | | 0.86 | |
| 60° C.-7 d | 8939 | 99.15 | 0.030 | 95.99 | 97.38 | 0.85 | 0.85 |
| | 8268 | 99.15 | 0.028 | 98.78 | | 0.85 | |
| 60° C.-14 d | 8144 | 99.17 | 0.028 | 98.38 | 98.81 | 0.83 | 0.85 |
| | 8520 | 99.14 | 0.028 | 99.25 | | 0.86 | |

TABLE 7

Solid stability data of micronized Form I of the compound of Formula I

| Sample type | Peak area | Peak area % | RRT 1.09 | Assay % | Average assay (%) | Total impurity (%) [b] | Average Total impurity (%) |
|---|---|---|---|---|---|---|---|
| Standard | 10435 | 99.16 | 0.162 | 100 | 100 | 0.84 | |
| RT | 9637 | 99.14 | 0.029 | 98.74 | 98.55 | 0.86 | 0.84 |
| | 8574 | 99.18 | 0.024 | 98.36 | | 0.82 | |
| 40° C.-75RH-7 d- | 9478 | 99.14 | 0.029 | 97.67 | 97.48 | 0.86 | 0.86 |
| | 8681 | 99.14 | 0.024 | 97.30 | | 0.86 | |
| 40° C.-75RH-14 d | 9404 | 99.11 | 0.028 | 96.20 | 97.10 | 0.89 | 0.88 |
| | 8804 | 99.12 | 0.028 | 98.00 | | 0.88 | |
| 60° C.-7 d | 8643 | 99.15 | 0.022 | 98.46 | 97.90 | 0.85 | 0.85 |
| | 9397 | 99.15 | 0.028 | 97.35 | | 0.85 | |
| 60° C.-14 d | 9733 | 99.12 | 0.027 | 98.52 | 98.37 | 0.88 | 0.87 |
| | 9704 | 99.13 | 0.028 | 98.23 | | 0.87 | |

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims.

What is claimed is:

1. A crystalline form of a compound of Formula I:

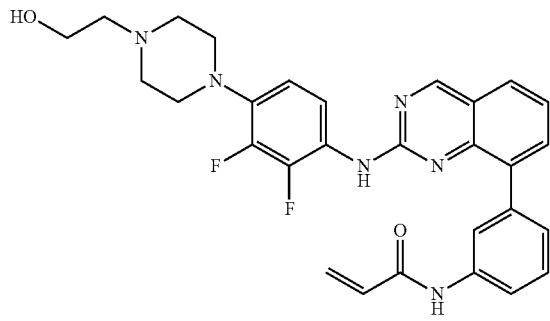

Formula I wherein the crystalline form is a polymorph Form I of the compound of Formula I.

2. The crystalline form of claim 1, wherein the polymorph Form I of the compound of Formula I is characterized by an X-ray powder diffraction pattern comprising peaks at 21.4±0.2 degrees, 18.3±0.2 degrees and 22.7±0.2 degrees two theta.

3. The crystalline form of claim 2, wherein the polymorph Form I is further characterized by:
  a differential scanning calorimetry (DSC) thermogram comprising an endotherm in the range of about 160-180° C.;
  a melting point of about 173° C.;
  rod like crystals;
  rod and column crystals;
  or a combination thereof.

4. A crystalline form of a compound of Formula I:

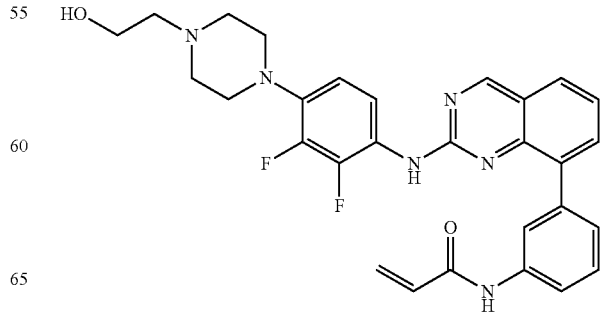

Formula I wherein the crystalline form is a polymorph Form II of the compound of Formula I.

5. The crystalline form of claim 4, wherein the polymorph Form II is characterized by:
an X-ray powder diffraction pattern comprising peaks at 7.5±0.2 degrees, 19.5±0.2 degrees, and 23.5±0.2 degrees two theta.

6. A crystalline form of a compound of Formula I:

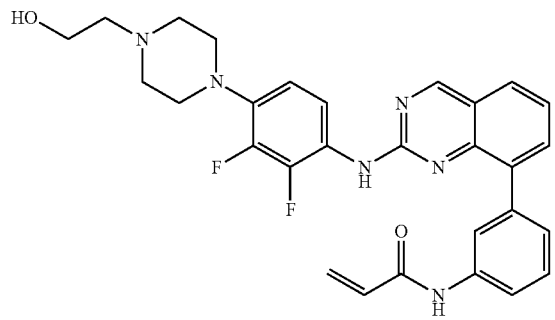

Formula I wherein the crystalline form is a polymorph Form III of the compound of Formula I.

7. The crystalline form of claim 6, wherein the polymorph Form III is characterized by:
an X-ray powder diffraction pattern comprising a peak at 6.5±0.2 degrees, 13.0±0.2 degrees, 19.6±0.2 degrees, 20.3±0.2 degrees, and 22.4±0.2 degrees two theta.

8. A crystalline form of a compound of Formula I:

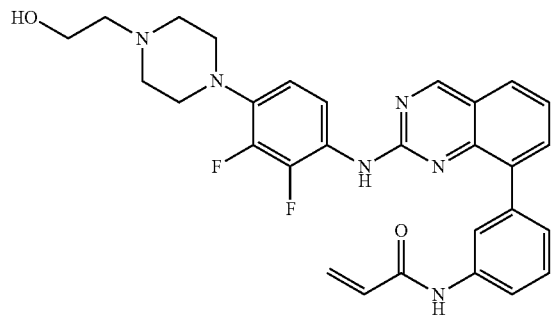

Formula I wherein the crystalline form is a polymorph Form IV of the compound of Formula I.

9. The crystalline form of claim 8, wherein the polymorph Form IV is characterized by:
an X-ray powder diffraction pattern comprising peaks at 24.5±0.2 degrees 20.7±0.2, 19.6±0.2 degrees, 18.0±0.2 degrees, 23.2±0.2 degrees, 7.4±0.2 degrees, and 8.0±0.2 degrees two theta.

10. A crystalline form of a compound of Formula I:

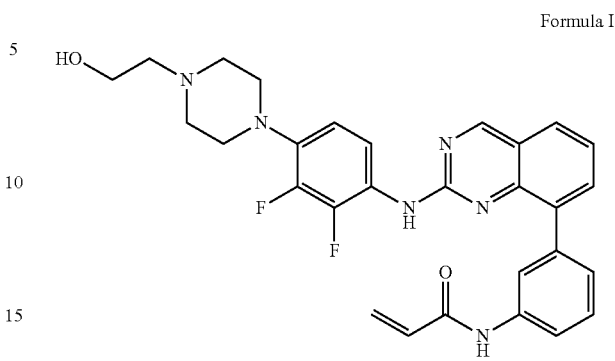

Formula I wherein the crystalline form is a polymorph Form V of the compound of Formula I.

11. The crystalline form of claim 10, wherein the polymorph Form V is characterized by:
an X-ray powder diffraction pattern comprising peaks at 5.7±0.2 degrees, 21.6±0.2 degrees, and 14.6±0.2 degrees two theta.

12. A crystalline form of a compound of Formula I:

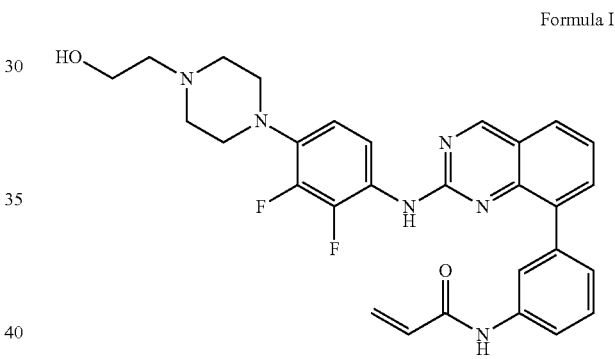

Formula I wherein the crystalline form is a polymorph Form VI of the compound of Formula I.

13. The crystalline form of claim 12, wherein the polymorph Form VI is characterized by:
an X-ray powder diffraction pattern comprising a peak at 6.6±0.2 degrees, 14.1±0.2 degrees, 20.5±0.2 degrees, and 22.6±0.2 degrees two theta.

14. A crystalline form of a compound of Formula I:

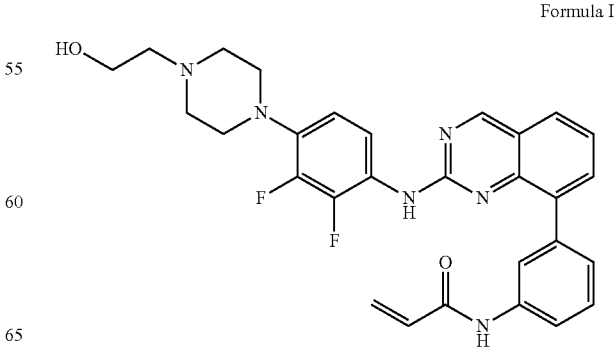

Formula I wherein the crystalline form is a polymorph Form VIII of the compound of Formula I.

15. The crystalline form of claim 14, wherein the polymorph Form VIII is characterized by:
an X-ray powder diffraction pattern comprising a peak at 6.7±0.2 degrees, 7.4±0.2 degrees, 14.1±0.2 degrees, 20.7±0.2 degrees, and 22.7±0.2 degrees two theta.

16. A composition comprising one or more crystalline forms of a compound of Formula I:

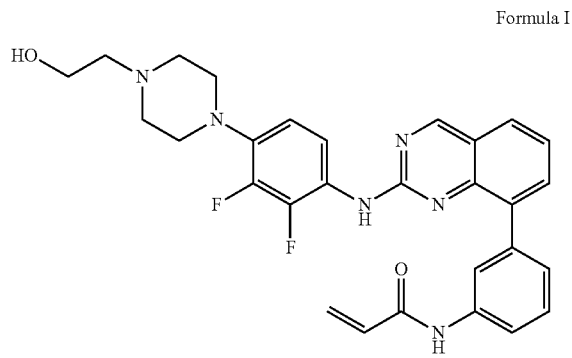 [SMILES: C=CC(=O)Nc1cccc(-c2cccc3cnc(Nc4ccc(N5CCN(CCO)CC5)c(F)c4F)nc23)c1]

Formula I wherein the one or more crystalline forms are selected from the group consisting of:
(i) a crystalline form characterized by an X-ray powder diffraction pattern comprising peaks at 21.4±0.2 degrees, 18.3±0.2 degrees and 22.7±0.2 degrees two theta;
(ii) a crystalline form characterized by an X-ray powder diffraction pattern comprising peaks at 7.5±0.2 degrees, 19.5±0.2 degrees and 23.5±0.2 degrees two theta;
(iii) a crystalline form characterized by an X-ray powder diffraction pattern comprising peaks at 6.5±0.2 degrees, 19.6±0.2 degrees, 22.4±0.2 degrees, 13.0±0.2 degrees and 20.3±0.2 degrees two theta;
(iv) a crystalline form characterized by an X-ray powder diffraction pattern comprising peaks at 24.5±0.2 degrees, 20.7±0.2 degrees, 19.6±0.2 degrees, 18.0±0.2 degrees, 23.2±0.2 degrees, 7.4±0.2 degrees, and 8.0±0.2 degrees two theta;
(v) a crystalline form characterized by an X-ray powder diffraction pattern comprising peaks at 5.7±0.2 degrees, 21.6±0.2 degrees, 14.6±0.2 degrees two theta;
(vi) a crystalline form characterized by an X-ray powder diffraction pattern comprising peaks at 6.6±0.2 degrees, 20.5±0.2 degrees, 22.6±0.2 degrees, and 14.1±0.2 degrees two theta; and
(vii) a crystalline form characterized by an X-ray powder diffraction pattern comprising peaks at 20.7±0.2 degrees, 22.7±0.2 degrees, 6.7±0.2 degrees, 7.4±0.2 degrees, and 14.1±0.2 degrees two theta.

17. A pharmaceutical composition comprising a pharmaceutically acceptable carrier and the crystalline form of claim 1.

18. A method of treating a cancer in a subject in need thereof, comprising administering to the subject a therapeutically effective amount of the crystalline form of claim 1, wherein the cancer is colon carcinoma, pancreatic cancer, breast cancer, ovarian cancer, prostate cancer, thyroid cancer, fibrosarcoma, myxosarcoma, liposarcoma, chondrosarcoma, osteogenic sarcoma, chondroma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, non-small cell lung cancer, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, or heavy chain disease.

19. A method of preparing a crystalline form of a compound of Formula I:

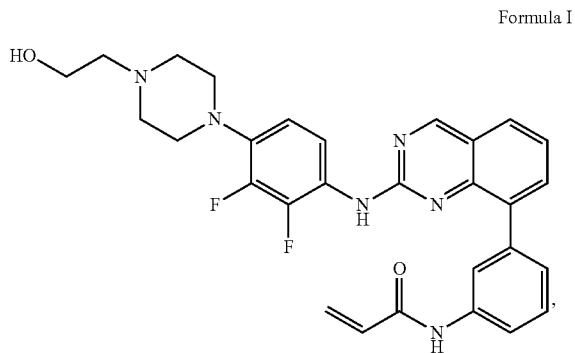 [SMILES: C=CC(=O)Nc1cccc(-c2cccc3cnc(Nc4ccc(N5CCN(CCO)CC5)c(F)c4F)nc23)c1]

Formula I wherein the method comprises:
(i) dissolving the compound of Formula I in a first solvent to obtain a mixture; and
(ii) crystalizing the mixture to obtain the crystalline form of the compound of Formula I.

20. A method of making a second crystalline form of a compound of Formula I:

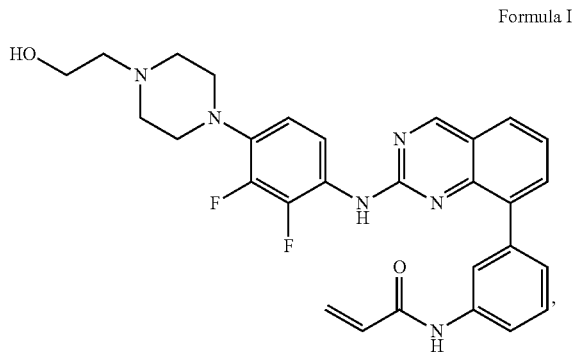 [SMILES: C=CC(=O)Nc1cccc(-c2cccc3cnc(Nc4ccc(N5CCN(CCO)CC5)c(F)c4F)nc23)c1]

Formula I wherein the method comprises drying a first crystalline form of the compound of Formula I at a temperature of about 70-90° C.

21. The crystalline form of claim 2, wherein X-ray powder diffraction pattern further comprises at least one peak selected from 25.8±0.2 degrees and 23.6±0.2 degrees two theta.

22. The crystalline form of claim 2, wherein the X-ray powder diffraction pattern comprises peaks at 5.0±0.2 degrees, 13.5±0.2 degrees, 17.2±0.2 degrees, 18.3±0.2 degrees, 21.4±0.2 degrees, 22.7±0.2 degrees, 23.6±0.2 degrees, and 25.8±0.2 degrees two theta.

23. The crystalline form of claim 4, wherein the polymorph Form II is further characterized by:
- a DSC thermogram comprising endotherms in the range of about 120-150° C. and about 175-200° C.;
- a DSC thermogram comprising endotherms at about 124° C. and about 183° C.;
- or a combination thereof.

24. The crystalline form of claim 6, wherein the polymorph Form III is further characterized by:
- a DSC thermogram comprising endotherms in the range of about 116-136° C. and about 184-194° C.;
- a DSC thermogram comprising endotherms at about 120° C. and about 188° C.;
- a melting point of about 188° C.;
- or a combination thereof.

25. The crystalline form of claim 8, wherein the polymorph Form IV is further characterized by:
- a DSC thermogram comprising endotherms in the range of about 115-135° C., about 168-178° C. and about 184-194° C., and an exotherm at about 137-147° C.;
- a DSC thermogram comprising endotherms at about 119° C., about 170° C. and about 187° C., and an exotherm at about 140° C.;
- or a combination thereof.

26. The crystalline form of claim 10, wherein the polymorph Form V is further characterized by:
- a DSC thermogram comprising endotherms in the range of about 152-162° C. and about 183-193° C.;
- a DSC thermogram comprising endotherms at about 156° C. and about 187° C., and an exotherm at about 159° C.;
- or a combination thereof.

27. The crystalline form of claim 12, wherein the polymorph Form VI is further characterized by:
- a DSC thermogram comprising endotherms in the range of about 120-140° C. and about 185-195° C.;
- a DSC thermogram comprising endotherms at about 123° C. and at about 188° C.;
- a melting point of about 188° C.;
- or a combination thereof.

28. The crystalline form of claim 14, wherein the polymorph Form VIII is further characterized by:
- a DSC thermogram comprising endotherm in the range of about 182-192° C. and at about 110-135° C.;
- a DSC thermogram comprising endotherm at about 187° C., and at about 114° C.;
- or a combination thereof.

29. A pharmaceutical composition comprising a pharmaceutically acceptable carrier and the composition of claim 16.

30. A method of treating a cancer in a subject in need thereof, comprising administering to the subject a therapeutically effective amount of the composition of claim 16, wherein the cancer is colon carcinoma, pancreatic cancer, breast cancer, ovarian cancer, prostate cancer, thyroid cancer, fibrosarcoma, myxosarcoma, liposarcoma, chondrosarcoma, osteogenic sarcoma, chondroma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, non-small cell lung cancer, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, or heavy chain disease.

* * * * *